United States Patent
Haslam et al.

(10) Patent No.: US 6,998,094 B2
(45) Date of Patent: *Feb. 14, 2006

(54) APPARATUS FOR AND METHODS OF HANDLING BIOLOGICAL SAMPLE CONTAINERS

(75) Inventors: James Keith Haslam, Dorset (GB); Paul Noble, Hampshire (GB); Keith Melvin Ebel, Dorset (GB)

(73) Assignee: Genetix Limited, New Milton (GB)

(*) Notice: Subject to any disclaimer, the term of this patent is extended or adjusted under 35 U.S.C. 154(b) by 598 days.

This patent is subject to a terminal disclaimer.

(21) Appl. No.: 10/133,904

(22) Filed: Apr. 29, 2002

(65) Prior Publication Data

US 2003/0044991 A1    Mar. 6, 2003

Related U.S. Application Data

(63) Continuation-in-part of application No. 09/946,958, filed on Sep. 6, 2001, now Pat. No. 6,843,962.

(51) Int. Cl.
*G01N 35/04* (2006.01)
*C12M 1/26* (2006.01)

(52) U.S. Cl. .......................... 422/65; 422/67; 422/104; 53/249; 53/270; 53/281; 53/284.5; 53/381.4; 53/468; 141/129; 141/130; 198/346.1; 198/347.2; 198/348; 414/277; 414/281; 435/286.3; 435/286.2

(58) Field of Classification Search .............. 53/50, 53/109, 167–169, 249, 270, 283, 284.5–284.6, 53/287, 324–325, 281, 381.4, 468, 471, 485, 53/505; 422/65–67, 100, 104; 435/286.2–286.4, 435/287.3; 141/129–130; 198/347.2, 348, 198/346.1; 414/277, 281

See application file for complete search history.

(56) References Cited

U.S. PATENT DOCUMENTS

2,675,953 A * 4/1954 Van Poolen ............ 53/381.4

(Continued)

FOREIGN PATENT DOCUMENTS

EP    1 074 488 A1    2/2001

(Continued)

OTHER PUBLICATIONS

Beggs et al., "Stacker Modules Used in a High-Capacity Robotics System for High throughput Screening Compound Replication", *Journal of Biomolecular Screening*, Larchmont, NY, US, vol. 4, No. 6, (Dec. 1999), pp. 373-379, XP009020148, ISSN: 1087-0571.

(Continued)

*Primary Examiner*—A Soderquist
(74) *Attorney, Agent, or Firm*—Foley & Lardner LLP

(57) ABSTRACT

Apparatus for handling biological sample containers comprises a conveyor assembly for conveying containers and a lid handling assembly operable to remove lids from and replace lids onto containers while the containers are in motion on the conveyor assembly. The lid handling assembly comprises a pair of ramps onto which a lid is lifted by a lifting mechanism configured to handle overhanging lids or non-overhanging lids as required. The lid handling assembly may be configured to handle lids of containers of various sizes by altering the ramp spacing. A conveyor assembly comprises a pair of converging rails which carry a pair of jaws operable to carry a container. The convergence of the rails makes the jaws clamp the container so that it is held tightly in position for micro-arraying to be carried out. The conveyor assembly may be adapted to handle different sizes of container by the provision of holders to hold various container types.

33 Claims, 38 Drawing Sheets

U.S. PATENT DOCUMENTS

| | | | |
|---|---|---|---|
| 2,683,560 A * | 7/1954 | Keller | 53/381.4 |
| 2,778,180 A * | 1/1957 | Eyster | 53/381.4 |
| 3,050,915 A * | 8/1962 | Silverstolpe | 53/111 R |
| 3,243,936 A * | 4/1966 | Anderson | 53/381.4 |
| 3,513,621 A * | 5/1970 | Chamberlin | 53/468 |
| 3,540,856 A | 11/1970 | Rochte et al. | |
| 3,556,731 A | 1/1971 | Martin | |
| 3,578,412 A | 5/1971 | Martin | |
| 3,704,568 A * | 12/1972 | Duhring et al. | 53/109 |
| 3,719,023 A * | 3/1973 | Richardson | 53/381.4 |
| 3,832,135 A | 8/1974 | Drozdowski et al. | |
| 3,844,896 A * | 10/1974 | Sharpe | 435/286.4 |
| 4,090,921 A * | 5/1978 | Sawamura et al. | 435/286.2 |
| 4,198,482 A * | 4/1980 | Homer | 435/309.1 |
| 4,468,914 A * | 9/1984 | Pestes | 53/505 |
| 4,495,149 A * | 1/1985 | Iwata et al. | 422/65 |
| 4,572,067 A * | 2/1986 | Fischer | 101/7 |
| 4,601,160 A * | 7/1986 | Heisler | 53/485 |
| 4,643,879 A * | 2/1987 | Hanaway | 422/104 |
| 4,720,463 A * | 1/1988 | Farber et al. | 435/286.5 |
| 4,728,607 A * | 3/1988 | Dorn et al. | 435/34 |
| 5,206,171 A * | 4/1993 | Dillon et al. | 435/286.3 |
| 5,340,540 A * | 8/1994 | Miller | 422/64 |
| 5,345,395 A * | 9/1994 | Griner | 702/32 |
| 5,585,068 A | 12/1996 | Panetz et al. | |
| 5,599,558 A * | 2/1997 | Gordinier et al. | 424/532 |
| 5,783,431 A * | 7/1998 | Peterson et al. | 435/455 |
| 5,985,214 A * | 11/1999 | Stylli et al. | 422/65 |
| 6,129,428 A | 10/2000 | Helwig et al. | |
| 6,148,878 A * | 11/2000 | Ganz et al. | 141/129 |
| 6,193,102 B1 * | 2/2001 | Bevirt et al. | 221/2 |
| 6,271,022 B1 * | 8/2001 | Bochner | 435/287.3 |
| 6,325,114 B1 * | 12/2001 | Bevirt et al. | 141/130 |
| 6,353,774 B1 * | 3/2002 | Goldenberg et al. | 700/245 |
| 6,449,827 B1 * | 9/2002 | Clarke et al. | 29/559 |
| 6,478,524 B1 | 11/2002 | Malin | |
| 6,843,962 B2 * | 1/2005 | Haslam et al. | 422/65 |
| 2002/0108857 A1 * | 8/2002 | Paschetto et al. | 204/457 |

FOREIGN PATENT DOCUMENTS

| | | |
|---|---|---|
| WO | WO 98/05753 A1 | 2/1998 |
| WO | WO 98/52047 A1 | 11/1998 |
| WO | WO 01/30541 A1 | 5/2001 |
| WO | WO 01/57538 A1 | 8/2001 |
| WO | WO 02/49761 A2 | 6/2002 |

OTHER PUBLICATIONS

"SCITEC high throughput screening systems", SCITEC Online Catalog, Online!, (Sep. 22, 1998), XP002269295, retrieved from the Internet: <URL:http://web.archive.org/web/1999022scitec-robotics.com/products/prdHTS.htm>, retrieved on Feb. 5, 2004.

Itoh et al., "Automated Filtration-Based High-Throughput Plasmid Preparation System" Genome Research, Cold Spring Harbor Laboratory Press, US, vol. 9, 1999, pp. 463-470, XP002938618, ISSN: 1088-9051.

"Autostack", SCITEC Online Catalog, Online!, Sep. 22, 1998, XP002269296, Retrieved from the Internet: <URL: http://web.archive.org/web/19990222005230/scitec-robotics.com/Products/prdautostack.htm>, retrieved on Feb. 5, 2004.

Gene Machines, Mantis™, http://web.archive.org/web/2000120...www.genemachines.com, XP-002259873 (1997).

Gene Machines, OmniGrid™, http://web.archive.org/web/2000120...www.genemachines.com, XP002259872 (1997).

Gene Machines, OmniGrid™, http://web.archive.org/web/20000092...www.hines.com, XP002261007, (1997).

GENETIX, Q Bot, http://web.archive.org/web/2000106102400/www.genetix. co.uk, XP002259874, (Oct. 9, 2000).

GENETIX, Q Select, http://www.genetix.co.uk/productpages/instruments/x96, XP002259875, (Nov. 1, 2002).

GENETIX, Q Select, Product Specification Sheet, XP002261008, (Oct. 17, 2002).

GENETIX, Q Bot, Product Specification Sheet, XP002261009,(Oct. 17, 2002).

GENETIX, Q Bot, http://www.genetix.co.uk/productpages/instruments/x80, XP002259485, (Apr. 17, 2003).

Gene Machines, Mantis™, http://genemachines.com/mantis/ind, XP002259878, (Oct. 9, 2003).

Gene Machines, Server Arm™, http://genemachines.com/serv, XP002261010, (Dec. 12, 2002).

Gene Machines, OmniGrid® 100, http://genemachines.com/omnigrid, XP002259877, (Mar. 12, 2003).

GENETIX, Q Fill 2, Product Specification Sheet, XP002261011, (Oct. 17, 2002).

GENETIX, Q Fill 2, http://www.genetix.com/productpages/instruments/x3000, XP002259878, (Feb. 10, 2003).

Clarke et al., "A Simple Automated Solution for Removing and Applying Sealing Microplate Lids," *Journal of Biomolecular Screening* ( 2001) , vol. 6, No. 5, pp. 333-338, XP009020149.

Q-Select, XP002259879, (Oct. 22, 2001).

Grimm et al., "Robotic High-Throughput Assay for Isolating Apoptosis-Inducing Genes," *BioTechniques* ( Mar. 2002), vol. 32, No. 3, pp. 670-677.

\* cited by examiner

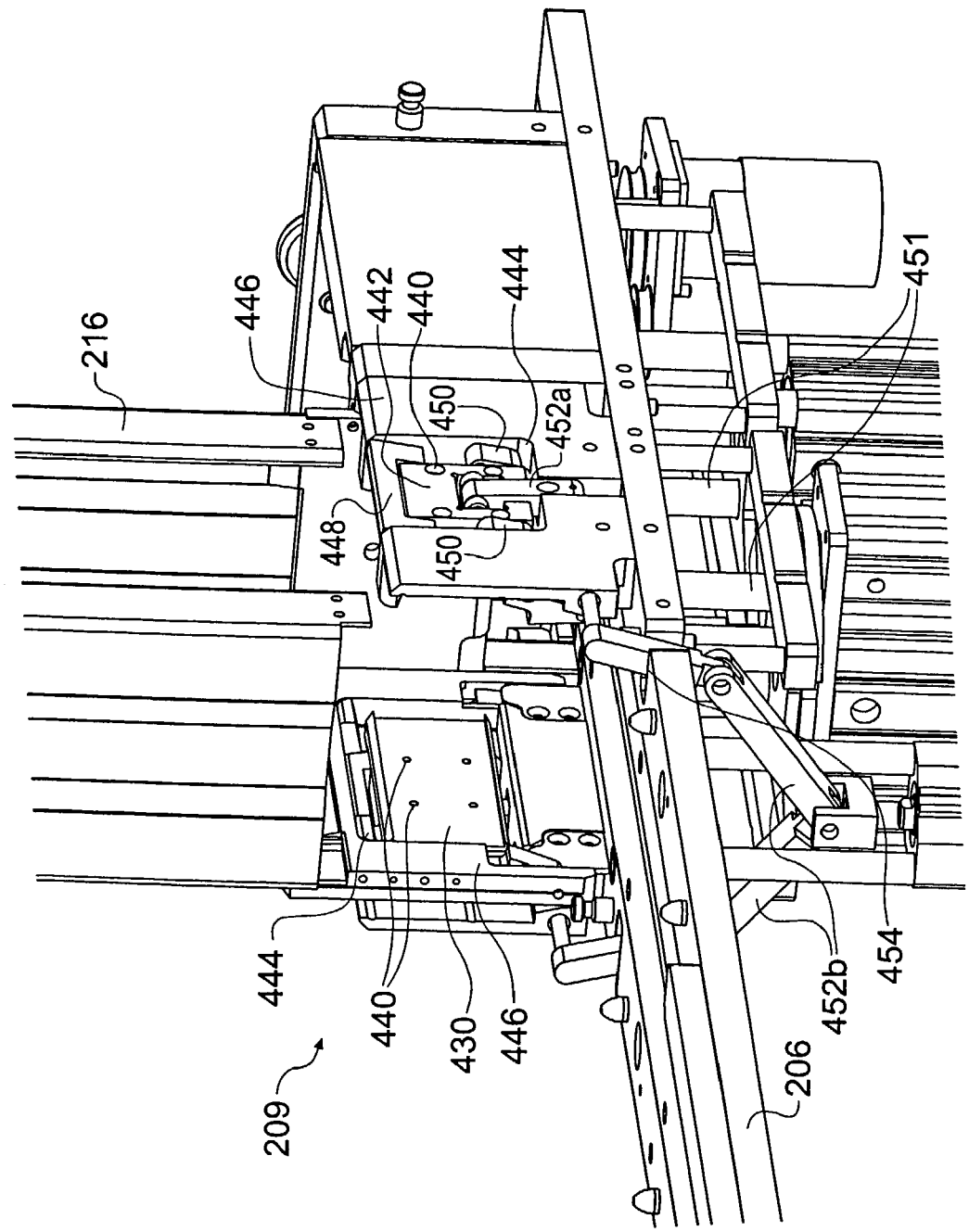

APPARATUS FOR AND METHODS OF HANDLING BIOLOGICAL SAMPLE CONTAINERS

BACKGROUND OF THE INVENTION

The invention relates to apparatus for and methods of handling biological sample containers, including removal and subsequent replacement of lids of the containers while the containers are being conveyed between positions. Especially, but not exclusively, the invention relates to the handling of Q-trays, omni trays, petri dishes and well plates.

The processing of biological and microbiological samples often includes the use of arraying and microarraying methods. These methods use moveable arrays of pins or needles to transfer small amounts of sample from one container to another. For example, a cell culture or colony may be grown in a container of one type, and samples from the colony may be transferred to other containers for subsequent testing.

The pin array is typically moved by computer control over an arraying surface on which the containers are arranged in appropriate positions. It is desirable that the containers are held firmly in place during the arraying, to allow accurate collecting and depositing of samples by the pins. Also, processing may be conducted in large volumes, with many samples requiring to be transferred in a short time. Therefore, it is further desirable that pluralities of containers can be placed on and removed from the arraying surface quickly and accurately.

Several different sizes and shapes of container are typically used, such as large rectangular Q-trays, smaller rectangular well plates (micro-tite plates) and omni trays, and circular petri dishes. The containers generally have lids to keep their contents safe from spillage and contamination. The style of lid differs between container types. Clearly, the lids need to be removed prior to arraying and replaced again afterwards. Automation of the lid removal and replacement facilitates the arraying process, so that a larger volume of containers can be handled in a given time.

A conventional method of delivering containers to the arraying surface uses vacuum suckers to remove and replace the lids. A container with a lid is moved, for example on a conveyor belt, to a lid-removal position at which it is brought to a standstill. A vacuum sucker is lowered down to contact the lid of the container, the vacuum causing the sucker to adhere to the lid. The vacuum sucker is then raised, carrying the lid with it. The container is then moved on to its arraying position. After arraying, the container is moved back to the lid-removal position and brought to a standstill again. The vacuum sucker is moved downward again so that the lid is lowered on the container. Removal of the vacuum releases the lid from the sucker. The container, with its lid, is then moved on from the lid-removal position.

The removal and replacement of lids in this way tends to slow down the operation of delivering and removing containers for arraying. Also, it is necessary to accurately locate a container under the vacuum sucker, which requires precise control of the conveyor. This is particularly important for lid replacement, when a lid and container need to be precisely aligned for lid replacement to be successful. This becomes increasingly difficult to achieve if a quantity of containers are moved together, which it is desirable to be able to do to increase the efficiency of the arraying process.

Hence, there is a requirement for an improved method of, and apparatus for, handling biological sample containers.

SUMMARY OF THE INVENTION

Accordingly, a first aspect of the present invention is directed to apparatus for handling biological sample containers each having a lid, the apparatus comprising:

a conveyor assembly operable to convey containers between a first position and a second position; and a lid handling assembly operable to remove lids from containers being conveyed through the lid handling assembly from the first position to the second position, and to replace the lids onto containers being conveyed through the lid handling assembly from the second position to the first position, lid removal and replacement being effected by mechanical interaction between the lids and the lid handling assembly as the containers are conveyed through the lid handling assembly.

This allows for the automation and speeding up of arraying processes which require containers to be arranged on an arraying surface and removed again afterwards, because there is no requirement for containers to be brought to a halt for lids to be removed or replaced. Also, as the containers are not brought to a halt, there is no requirement for accurate positioning of containers, so that the conveyor assembly does not need any precise control as far as the lid handling is concerned. This reduces the complexity and hence cost of the apparatus. However, the apparatus may be brought to a halt during removal or replacement of the lids with no detrimental effect. The use of a mechanical interaction between the lid and lid handling assembly to remove and replace the lid further reduces complexity, as it is possible to contrive lid handling with few, if any, moving parts.

Advantageously, the lid handling assembly comprises a pair of ramps arranged such that the conveyor assembly conveys a container between the pair of ramps from the first position to the second position and from the second position to the first position, the ramps sloping upward from lower ramp ends facing towards the first position and arranged such that they pass under side walls of the lid of a container being conveyed between the pair of ramps from the first position to the second position.

The use of ramps provides a particularly simple and attractive way of removing and replacing lids, which may be effected with no moving components. Ramps also permit accurate and repeatable lid replacement, with no need for precise location of parts prior to replacement.

The lid handling assembly may further comprise a pair of rotatable rollers, one located in front of each lower ramp end and each roller having an axis of rotation inclined with respect to a perpendicular to a plane in which the containers are conveyed, the rollers operable to engage the lid of a container being conveyed between the pair of ramps from the first position to the second position and to direct the lid over the lower ramp ends. The arrangement permits the simplicity of using ramps to be further exploited with containers which do not have overhanging lids.

In an alternative embodiment, the lid handling assembly comprises a pair of rotatable rollers arranged such that the conveyor assembly conveys a container between the pair of rollers from the first position to the second position and from the second position to the first position, each roller having an axis of rotation inclined with respect to a perpendicular to a plane in which the containers are conveyed, the rollers operable to grip the lid of a container being conveyed between the rollers from the first position to the second position and feed the lid in a forwardly and upwardly direction.

In one embodiment, the conveyor is further operable to convey containers from the first position to a third position after the containers have been conveyed from the second position to the first position. The provision of three container positions gives greater flexibility to the handling arrangements. For example, it offers the possibility for containers to be unloaded automatically from one storage device, and loaded into a different storage device after arraying, so that containers can be kept entirely separate before and after arraying. This is a valuable feature in, for example, testing applications in which it is important that samples do not become muddled.

A second aspect of the present invention is directed to a lid-handling assembly operable to remove lids from biological sample containers as the containers are conveyed through the assembly in a first direction and to replace the lids onto the containers as the containers are conveyed through the assembly in a second direction, lid removal and replacement being effected by mechanical interaction between the lids and the lid handling assembly as the containers are conveyed through the lid handling assembly, and the assembly being removably mountable on a conveyor assembly operable to convey biological sample containers.

A removably mountable lid handling assembly offers the advantage that the assembly can be readily replaced by an alternative assembly configured to handle different sizes or types of lid. Therefore, a container handling apparatus can be adapted to handle any of a range of containers, according to user requirements.

A third aspect of the present invention is directed to a storage cassette for storing a plurality of biological sample containers, comprising:
  an elongate receptacle for receiving a stack of containers, open at least an open end; and
  at least one movable protrusion located towards the open end and operable to retain a stack of containers within the receptacle when in a first position and to let containers pass through the open end when in a second position.

A storage cassette of this type allows containers to be loaded into and unloaded from it very simply, so that this can be readily performed automatically by a suitably configured container handling apparatus. This automation increases the efficiency of arraying processes.

A fourth aspect of the present invention is directed to apparatus for conveying biological sample containers, the apparatus comprising:
  one or more conveying lanes; and
  a conveying device associated with each conveying lane, operable to transport one or more containers along the associated conveying lane between a first position in which the conveying device is unengaged with the one or more containers and a second position in which the conveying device holds the one or more containers.

It is desirable for containers to be held firmly in place during arraying, so that colonies in the containers can be picked accurately. A conveying device of this type automatically holds the containers in the correct position by gripping them, but also is completely unengaged with the containers when they are not in this position so that containers can be easily and quickly placed into and removed from the conveying device before and after arraying.

In a preferred embodiment, each of the one or more conveying lanes comprises a track along which the associated conveying device may move, the track arranged so as to clamp any containers being transported against the conveying device when the conveying device is in the second position. The track may comprise a pair of converging rails which converge towards the second position.

Use of the track to provide the gripping of the containers means that the conveying device can be simple with no moving parts. A track comprising converging rails is a particularly straightforward way of achieving this.

A fifth aspect of the present invention is directed to a holder for holding biological sample containers comprising:
  a plate having shape and dimensions substantially the same as those of a tray; and
  one or more recesses in an upper surface of the plate, the or each recess being shaped to receive a biological sample container smaller than a Q-tray.

Holders of this configuration can be used with a single container handling apparatus to allow the apparatus to handle a range of sizes and shapes of container. Thus the apparatus can be readily modified according to user requirements.

A sixth aspect of the present invention is directed to an apparatus for working with biological material, comprising:
  a work surface;
  a first container handling apparatus, for handling biological sample containers containing biological material, comprising:
    a storage assembly operable to store containers, deliver containers to a first pick-up position, and remove containers from the first pick-up position;
    a first conveyor assembly operable to convey containers between the first pick-up position and a first working position on the work surface; and
    a first lid-handling assembly operable to remove lids from containers as they are conveyed through the first lid handling assembly from the first pick-up position to the first arraying position and to replace the lids onto the containers as they are conveyed through the first lid handling assembly from the first arraying position to the first pick-up position, lid removal and replacement being effected by mechanical interaction between the lids and the first lid handling assembly as the containers are conveyed through the first lid handling assembly;
  a second container handling apparatus, for handling well plates, comprising:
    a well plate release mechanism operable to release well plates from a first storage cassette containing a stack of well plates and to deliver them to a second pick-up position;
    a second conveyor assembly operable to convey well plates from the second pick-up position to a second working position on the work surface and from the second working position to a return position;
    a second lid-handling assembly operable to remove lids from well-plates as they are conveyed through the second lid handling assembly from the second pick-up position to the second working position and to replace the lids onto the well-plates as they are conveyed through the second lid handling assembly from the second working position to the return position, lid removal and replacement being effected by mechanical interaction between the lids and the second lid handling assembly as the containers are conveyed through the second lid handling assembly; and
    a well plate loading mechanism operable to transfer well plates from the return position into a second storage cassette; and a head carrying a plurality of pins or pipettes operable to move over the work surface, pick up material from containers in the first working position and deposit the material in well plates in the second working position.

This apparatus provides total automation of arraying, gridding and other processes in which biological material needs to be transferred between containers, by handling all containers involved quickly and efficiently, including removing and replacing container lids while the containers are moving, and providing a plurality of containers in sequence as they are required. This permits continuous arraying with a large volume of containers.

A seventh aspect of the present invention is directed to a method of handling biological sample containers each having a lid, the method comprising:

conveying a container with a lid from a first position through a lid handling assembly;

arranging a first mechanical interaction between the lid and the lid handling assembly as the container is conveyed through the lid handling assembly which removes the lid from the container;

conveying the container without its lid to a second position;

conveying the container without its lid from the second position through the lid handling assembly;

arranging a second mechanical interaction between the lid and the lid handling assembly as the container is conveyed through the lid handling assembly which replaces the lid onto the container; and conveying the container with its lid back to the first position.

An eighth aspect of the present invention is directed to a method of handling biological sample containers comprising:

placing a container within a conveying device;

moving the conveying device between a first position in which the conveying device is unengaged with the container and a second position in which the conveying device holds the container.

BRIEF DESCRIPTION OF THE DRAWINGS

For a better understanding of the invention and to show how the same may be carried into effect reference is now made by way of example to the accompanying drawings in which:

FIG. 28 shows a perspective view of the well plate release mechanism of FIG. 27;

DETAILED DESCRIPTION

First Embodiment

Figure 1:
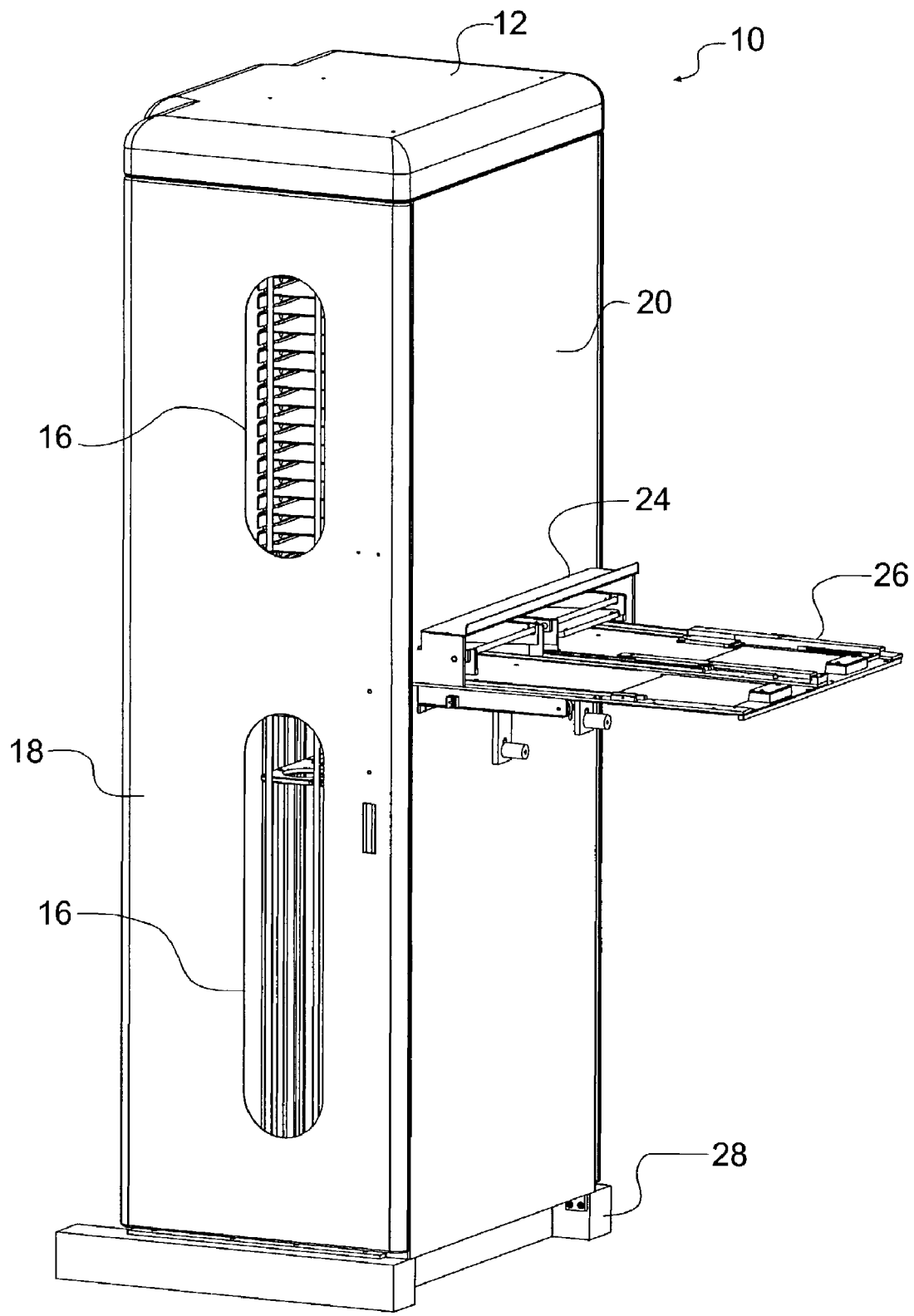
FIG. 1 shows a perspective view of the exterior of an embodiment of a container feeder apparatus according to the invention.

FIG. 1 shows a perspective view of the exterior of a container feeder apparatus 10 which is operable to handle containers so as to deliver and retrieve any of a number of biological sample containers having lids and previously loaded into the apparatus. The apparatus removes the lid of a container on delivery and replaces the lid on retrieval.

The apparatus 10 comprises a storage assembly having a housing 12 with four walls and a top which define a vertical rectangular column which sits on a base 28. The housing 12 contains two elevators 34 which are partly visible through windows 16 in a side wall of the housing 12. This side wall of the housing 12 is an opening panel 18 which is hinged to the housing 12 by hinges (not shown) which allow the panel 18 to open about a vertical axis, giving access to the elevators 34. A button (not shown) is provided at one side of the panel 18 which controls a latch operable to keep the panel 18 in a closed position. The panel 18 can be opened by pushing the button to release the latch. A safety interlock (not shown) is provided to control when the panel 18 can be opened, depending on operation of the feeder apparatus 10.

A horizontal elongate aperture 24 is provided in a front panel 20 of the housing 12, and located approximately half-way up the front panel 20. A conveyor assembly 26 having a substantially horizontal planar configuration protrudes through the aperture 24. An interior portion of the conveyor assembly 26 is located within the housing 12 and engages with the elevators 34, and an exterior portion of the conveyor assembly 26 extends outside the housing 12. The conveyor assembly 26 remains fixed when the panel 18 is opened or closed.

Figure 2:
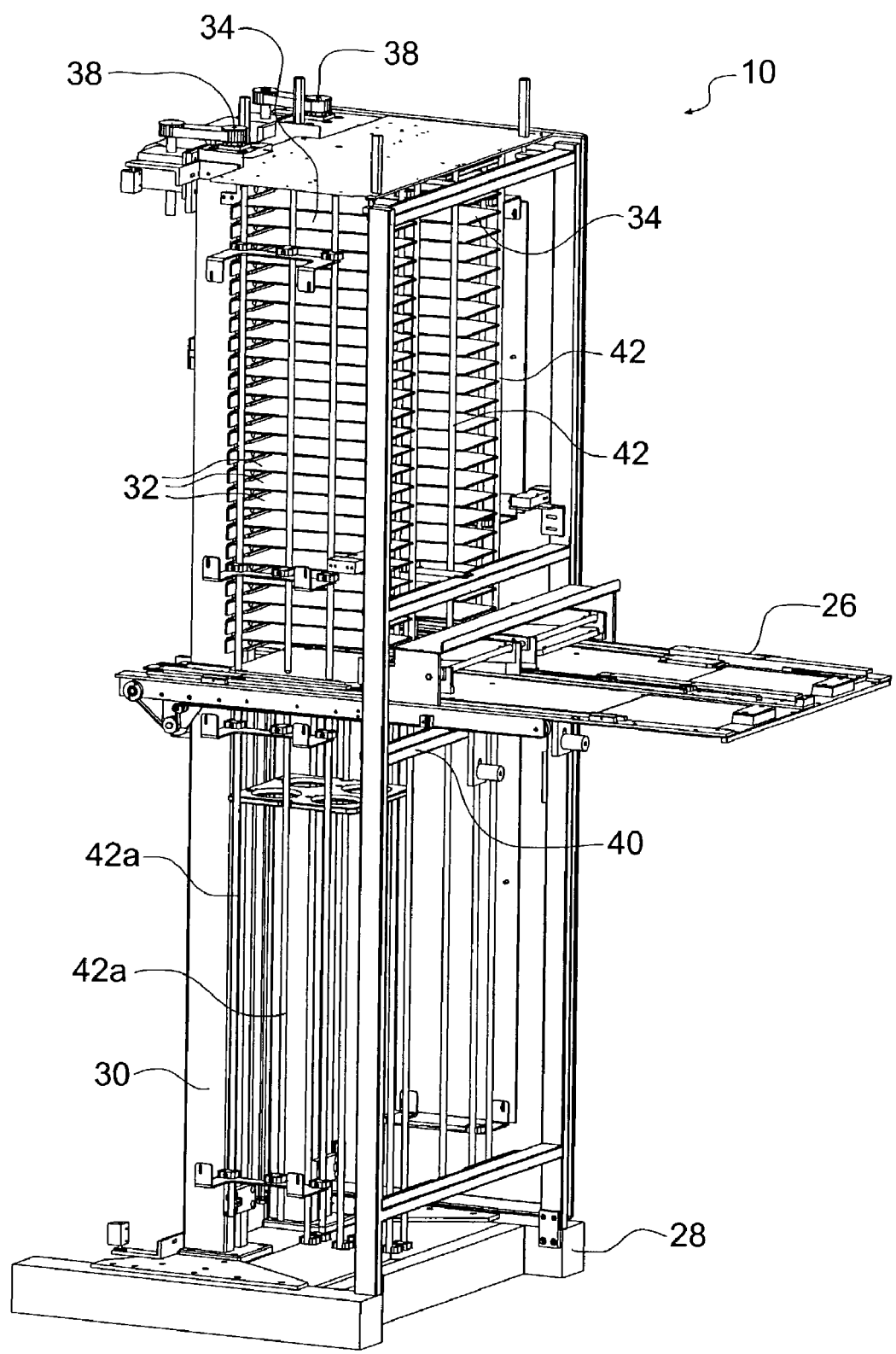
FIG. 2 shows a perspective view of the interior of the container feeder apparatus of FIG. 1.

FIG. 2 shows a perspective view of the feeder apparatus with the housing 12 removed. The base 28 has mounted upon it a frame 30 which supports the elevators 34. The elevators 34 comprise a plurality of vertically spaced shelves 34. A holder for biological sample containers in which each container is arranged on a shelf or other rest is often referred to as a "hotel" arrangement in the art. The illustrated elevators each have twenty-five shelves, giving a total of fifty shelves. The shelves 32 are vertically movable within the frame 30, the movement being driven by an elevator motor 38. The motors 38 can move the shelves 32 of each elevator 34 independently or together. The shelves 32 occupy about half the height of the housing 12 and frame 30. This gives a sufficient degree of vertical movement of the shelves 34 to allow each of the shelves 32 to be brought level with the conveyor assembly 26. Movement of the shelves 32 is defined by a plurality of vertical guide bars 42. The guide bars at the side of the elevators 34, some of which are labelled 42a in the Figure, are coupled to the panel 18 so that the guide bars 42a swing away from the elevators 34 when the panel 18 is opened. This gives clear access to the elevator shelves 32.

Figure 3:
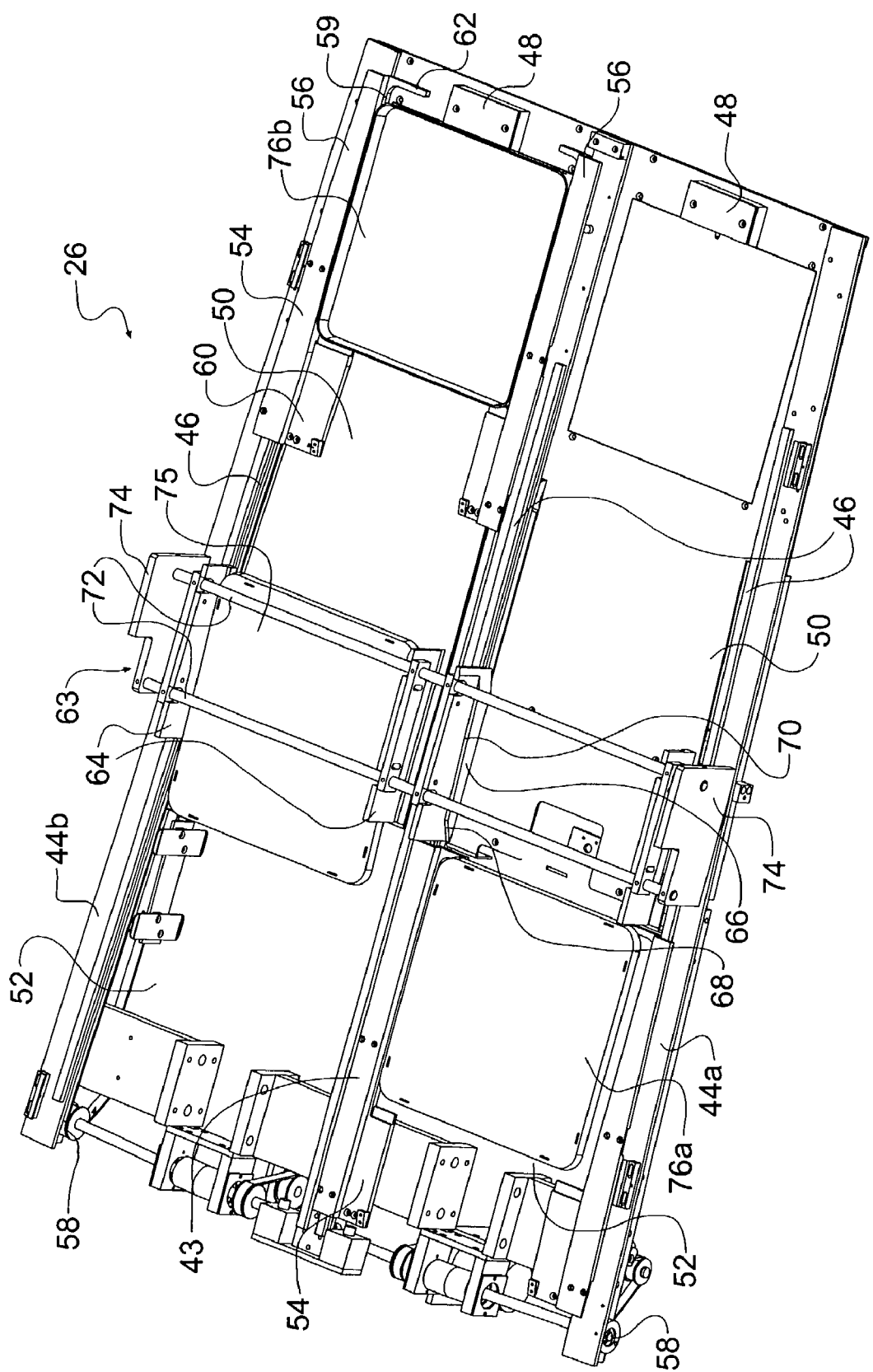
FIG. 3 shows a perspective view of an embodiment of a conveyor assembly of the container feeder apparatus of FIG. 1.

FIG. 3 shows the conveyor assembly 26 in more detail. The conveyor assembly 36 has a planar configuration comprising a framework 43 defining two adjacent conveyors or conveying lanes 44. Each conveyor 44 has two long sides each bounded by rails 46, the rails 46 forming a track, and two ends. The exterior end, on the exterior portion of the conveyor assembly 26, has a buffer 48. The buffer 48 does not extend across the full width of the conveyor 48, and is located centrally with respect to the width of the conveyor 48. The rails 46 of each conveyor 44 are angled with respect to each other in the horizontal plane, and converge towards the exterior end. The exterior portion of the conveyor assembly 26 has a delivery surface 50 which extends across the width of each conveyor 44 just below the height of the rails 46. The interior portion of the conveyor assembly 26 has no such surface, so that an opening 52 is present in each conveyor 44 extending between its rails 46.

The conveyor assembly 26 is located within the housing 12 so that each conveyor 44 is in line with an elevator 34. The conveyor assembly 26 is fastened to the frame 30 and supported underneath by a horizontal bar 40 extending across the frame 30. Each elevator shelf 32 is free to move vertically through the opening 52 in its respective conveyor 44. The elevator motors 38 can move the elevator shelves 32 and position them so that an elevator shelf 32 from each elevator 34 is at the same height as the delivery surface 50.

Each conveyor 34 is equipped with a conveying device 54. Each conveying device comprises a pair of sliding jaws 56. The jaws 56 are mounted on the rails 46, one on each side of the conveyor 44. Each jaw 56 can be slid along its rail 46 by a motor-driven belt drive 58 which is operable to move the jaw 56 to and from a first position at the interior end of the conveyor assembly 26 and a second position at the exterior end of the conveyor assembly 26. Each jaw 56 is driven separately, and the jaws 56 are not connected together in their pairs, but the belt drives 58 operate so as to move each pair of jaws 56 together to maintain the integrity of the conveying devices 54. Owing to the converging arrangement of the rails 46, the jaws are closer together in the second position than the first position.

Each jaw 56 is elongate along its direction of travel, and has a shaped flange 59 projecting from its inner surface towards the centre line of the conveyor 44. The end of the flange 59 closest to the interior end of the assembly 26 is shaped to form a large dog 60, which protrudes beyond the flange 59. Similarly, the end of the flange 59 closest to the exterior end of the assembly 26 is provided with a small dog 62 which also protrudes towards the centre line of the conveyor 44. The flange 59 and both dogs 60, 62 have a vertical thickness which is less than the vertical thickness of the jaw 56. The corners defined by the dogs 60, 62 meeting the flange 59 and which face each other are rounded, so that the sides of the dogs 60, 62 and the side of the flange 59 define a shallow 'U' shape. The 'U' shape is lined with rubber.

The extent of travel of the jaws 56 is such that the small dogs 62 can travel past the first edge of the buffer 48.

Each conveyor also comprises a lid-handling assembly 63, operable to remove and replace the lids of containers travelling on the conveyors. Each side of each conveyor 44 is provided with a low vertical wall 64 positioned about half-way along the conveyor 44. The inner surface of each wall 64 (i.e. the surface facing towards the opposite wall) has an integral ramp 66 extending from it over the conveyor, and sloping generally upwards from lower ramps ends at the end of the wall 64 nearest the interior end of the assembly 26. Each wall 64 is spaced apart from the rail 46 along the side of the conveyor 44 so that the jaw 54 can pass along the rail 46 without hitting the wall 64. The lower edge of each wall 64 and ramp 66 is positioned at a height which allows the flange 59 and dogs 60, 62 of the jaw 56 to pass under the wall 64 and ramp 66.

Each ramp has two portions, each with a different gradient. The initial, lower ramp portion 68 has a slope of approximately 30° with the horizontal, and the upper ramp portion 70 has a much shallower slope, of approximately 5° to the horizontal.

The walls 64 and their ramps 66 are connected together by a pair of horizontal rods 72 which pass through holes 74 in the walls 64 and extend across the width of the conveyor assembly 26 above the conveyors 44. The ends of the rods 72 are held in brackets 74, with one bracket 74 on each side of the assembly 26. The brackets 74 are removably fastened to the outer sides of the framework 43 of the assembly 26, for example with nuts and bolts. By unfastening the nuts and bolts, the ramps 66, walls 64, rods 72 and brackets 74 can be removed from the conveyor assembly 26 as a single piece comprising the lid-handling assembly 63.

Figure 4:
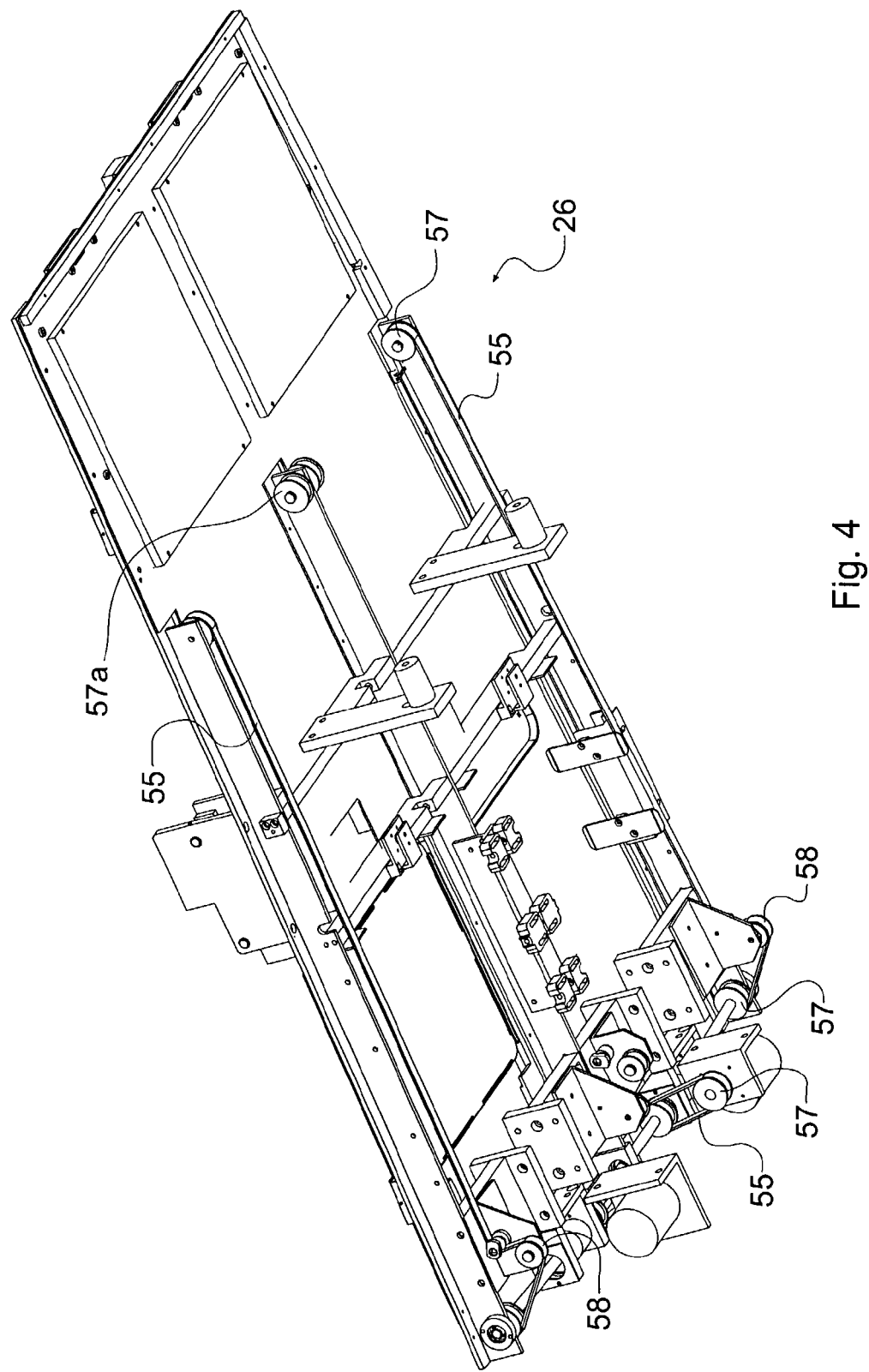
FIG. 4 shows a further perspective view of the conveyor assembly of FIG. 3.

FIG. 4 shows a perspective view of the underside of the conveyor assembly 26. The belt drives 58 used to move each jaw 56 are visible. They comprise, in the conventional manner, a belt 55 passing around a series of rollers 57. The belts of the two central drives have not been included, to show the rollers 57a more clearly.

Preferably, a controller such as computer is provided to control operation of the feeder apparatus 10, by operating the elevator 14 via the elevator motors 38 and the conveying devices 54 via the belt drives 58. The computer may be preprogrammed with a sequence of commands.

Some of the dimensions of the feeder apparatus 10 are determined in accordance with the type of container to be handled. The embodiment illustrated in FIGS. 1, 2, 3 and 4 is configured to handle containers known as Q-trays. These are large flat generally square plastic trays measuring 235 mm by 235 mm by 16 mm or more deep, which have rounded corners and a low wall. The trays have lids which also have rounded corners and which fit loosely over the trays so that the edge walls of the lid overhang the tray. The walls of the lid are shorter than the walls of the tray so that there is a gap between the lower edge of the lid wall and any surface on which the tray rests.

In accordance with this, the elevator shelves 32 are each large enough to accommodate one Q-tray. The shelf area is approximately the same as the area of a Q-tray. The spacing between vertically adjacent shelves 32 must be sufficient to accommodate the height of a Q-tray with a lid. The openings 52 must be large enough to let the elevator shelves 32, with the Q-trays on, pass vertically through them when the jaws 56 are positioned at the extreme interior end of the conveyor assembly 26. A certain amount of clearance is preferably provided, so that rails 46 are spaced so that the distance between the jaws 56 (base of 'U' shape to base of 'U' shape) at this position is the width of a Q-tray plus about 25 mm. Similarly, the length of the jaws 56 is defined so that the distance across each 'U' shape is the length of a Q-tray plus about 25 mm.

When the jaws 56 are in the second position, at the exterior end of conveyor apparatus 26, they are designed to hold a Q-tray firmly, as will be described in more detail later. Therefore, the rail spacing at this end is arranged to that the distance between the jaws 56 is the width of a Q-tray. At all points along the rails 56, the distance from one large dog 60 to the opposite large dog 60, and the distance from one small dog 62 to the opposite small dog 62 is less than the width of a Q-tray. In this way, a Q-tray is encompassed by the jaws on all sides at any position along the rails 56.

Regarding the ramps 66, these protrude over the conveyors 44 to an extent such that the spacing between them is just sufficient to let a Q-tray pass between them, but the spacing is less than the width of the overhanging lid of the Q-tray. These dimensions will need to be altered accordingly if the apparatus is to handle containers of other sizes.

The operation of the feeder apparatus 10 will now be described.

Initially, the conveying devices 54 are positioned in the first position, at the interior end of the conveyor assembly 26.

The panel 18 of the housing 12 is opened by using the button. Q-trays with lids on are placed in the elevators 34, one per elevator shelf 32, using as many shelves 32 as are required. The Q-trays contain cultured colonies of biological samples. The panel 18 is then closed, and the apparatus 10 is activated by the controller.

The elevator motors 38 move the elevators 34 vertically until an elevator shelf 32 containing a Q-tray 76 in each elevator 34 is level with the delivery surface 50 of the conveyor assembly 26. The Q-trays 76 on the shelves 32 are therefore encompassed by the jaws 56 of the conveying devices 54.

Figure 5A:
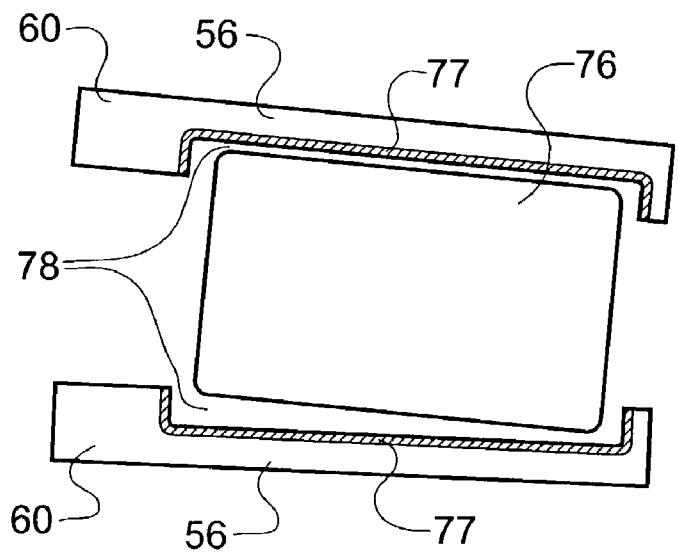
FIGS. 5(a), 5(b) and 5(c) show schematic plan views of part of the conveyor assembly of FIG. 3 in operation.

FIG. 5(a) shows a schematic plan view of a Q-tray 76 in this position. The Q-tray 56 is located within the jaws 56, which have rubber linings 77, but spaced apart from the jaws 56 by the clearance gap 78 required to permit easy vertical travel of the elevator 14.

Once the Q-trays 76 are in this position, the elevators 34 stop, and the controller activates the belt drives 52 to move the jaws 56. Considering just one conveyor 44, the jaws 56 move forwards along their rails 46 until the large dogs 60 abut the rear wall of the Q-tray 76, at which point the jaws 56 start to push the Q-tray 76 forwards. The Q-tray 76 is pushed off the elevator shelf 32 and onto the delivery surface 50. The jaws 56 carry the Q-tray 76 through the lid-handling assembly 63, the operation of which is described in detail below, and the Q-tray 76 emerges from the lid-handling assembly without its lid 75. The jaws 56 continue to push the now lidless Q-tray 76 forwards until the front wall of the tray abuts the buffer 48. In this position (the second position), the Q-tray 76 is tightly held between the jaws 56. This is because the convergence of the rails 46 brings the jaws 56 closer together as they move forwards so that the clearance gap 78 is closed and the rubber lining 77 comes into contact with walls of the Q-tray 76. The rubber lining 77 gives a high friction contact between the jaws 56 and the Q-tray 76.

Figure 5B:
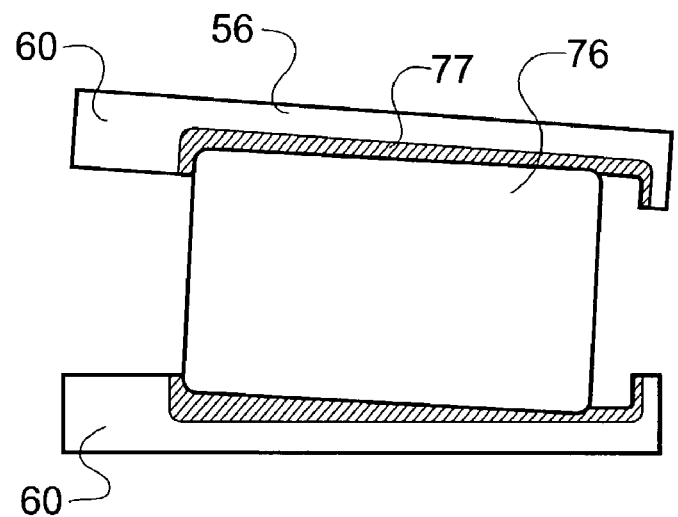

FIG. 5(b) is a schematic plan view of the Q-tray 76 and jaws 56 in this position, showing how the Q-tray 76 is held between the jaws 56 and held in place by the rubber lining 77. The large dogs 60 are in contact with the rear wall of the tray 76, having pushed the tray 76 into position. Also, in FIG. 3, the Q-tray 76b on conveyor 44b is shown in the held position.

When the Q-tray 76 reaches the second position, it is ready for colony picking as part of an arraying process to be performed. This is typically achieved by using a camera to photograph the contents of the tray. The photograph is processed by computer to obtain co-ordinates of colonies in the tray. The computer then uses the co-ordinates to enable it to control an array of pins or needles which are moved and dipped into the colonies to obtain samples which can then be transferred elsewhere, such as to another tray. Therefore it is important to be able to accurately maintain the position of the Q-tray, so that the colonies remain at their measured co-ordinates. However, it is possible that the pins may impact on the bottom of the tray, which could cause the tray to slip out of position. Hence the feeder apparatus 10 features jaws 60 that are provided with a rubber lining 77, so that trays are tightly held and inhibited from being knocked out of position.

After colony picking, the drive belts 58 are driven in reverse so that the jaws 56 travel along the rails 46 towards the elevator 14, taking the Q-tray 76 with them. The diverging rails 46 cause the jaws 56 to open, so that the Q-tray 76 is held less tightly, and eventually released. When this happens, the jaws 56 move past the Q-tray 76 until the small dogs 62 come into contact with the front wall of the Q-tray 76.

Figure 5C:
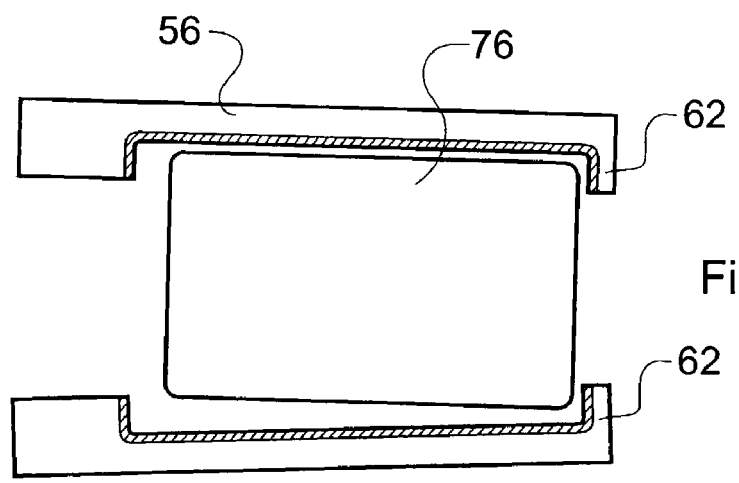

FIG. 5(c) shows a schematic plan view of the Q-tray 76 and jaws 56 just before the tray 76 is picked up by the small dogs 62. When this has happened, the moving jaws 56 pull the Q-tray along, through the lid-handling assembly 63 which replaces the lid 75, and back to the first position, on the elevator shelf 32. The elevators 34 then move vertically to present further Q-trays to the first position to be delivered by the conveyor assembly 26 for colony picking.

FIGS. 6(a) to 6(d) show a series of simplified cross-sectional side views of a Q-tray 76 and a ramp 70 to illustrate the operation of the lid-handling apparatus 63.

Figure 6A:
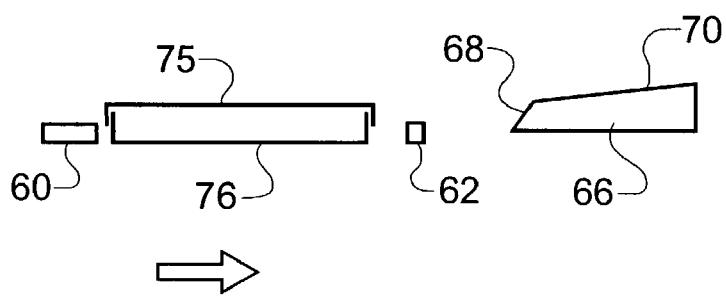
FIGS. 6(a), 6(b), 6(c) and 6(d) show schematic cross-sectional views of an embodiment of a lid-handling assembly forming part of the conveyor apparatus of FIG. 3.

In FIG. 6(a), the Q-tray 76 has its lid 75 on, and is being carried towards the ramps 66 by the jaws which each have a large dog 60 and a small dog 62. The large dog 60 pushes against the rear wall of the Q-tray 76.

Figure 6B:
Figure 6C:
Figure 6D:

The lower edges of the ramps 66 are below the height of the lower edge of the lid 75. As the Q-tray 76 reaches the start of the ramps 66, the overhanging lid 75 hits the front of the ramps 66, which are able to pass under the edges of the lid 75. The Q-tray 76 can move past the ramps 66, as it is narrower than the spacing between them, and the dogs 60, 62 are small enough to pass under the ramps 66. Therefore, as the Q-tray 76 is pushed forwards, the lid 75 begins to climb the ramps 66, as shown in FIG. 6(b). Hence the lower, front ends of the ramps act as a lifting mechanism to lift a lid onto the ramps. The large dogs 60 are in contact with the rear of the Q-tray 76 and the lid 75, so that the lid 75 is pushed up the ramps 66 as the Q-tray 76 continues to be pushed forwards. Eventually, the lid 75 is lifted by the ramps to a height sufficient to let the large dogs 60 pass under the lower edge of the lid 75, and push the Q-tray 76 forwards without the lid 75, as shown in FIG. 6(c). The lid 75 remains on the ramps 66 as the Q-tray is pushed towards its final position for colony picking. FIG. 6(d) shows this arrangement. The walls 64 extending above the ramps 66 have a space between them just sufficient to accommodate the width of the lid 75 so that the lid 75 is maintained in the correct lateral position.

The ramps 66 have two sloped sections, the initial, lower ramp portion or section 68 being much steeper than the secondary, upper ramp portion or section 70. The steep initial sections 68 lift the front of the lid 75 quickly to remove it from the path of the advancing Q-tray 76. The shallow secondary sections 70 lift the lid at a slower rate, but permit it to rest at a shallow incline so that it does not slip down the ramps under gravity once the large dogs 60 have passed under it.

After colony picking, the lid 75 is replaced on the Q-tray 76 by a process that is substantially the reverse of the lid removal process. The small dogs 62 pull the Q-tray 76 back towards the ramps 66. The relative heights of the dogs 60, 62 and the Q-tray wall mean that the lid removal process leaves the lid 75 at a height at which its lower edge is below the upper edge of the Q-tray wall, but above the large dogs 60. Hence, the large dogs 60 pass under the lid 75 on the ramps 66, but the rear wall of the Q-tray 76 hits the rear wall of the lid 75 and begins to pull the lid 75 down the ramps 66 as the Q-tray 76 proceeds. Eventually the lid 75 is pulled right off the ramps 66 and falls onto the Q-tray 76 in the correct orientation so that the Q-tray 76 is properly covered by the lid 75.

Hence, the lid removal and lid replacement for the Q-trays is performed whilst the Q-trays are in motion; indeed, the motion contributes to the process. No moving components additional to those already provided to move the Q-trays are required to remove and replace the lids. The Q-trays can be delivered for picking much more quickly than is possibly with conventional lid removal methods using vacuum suction, as there is no need to bring the Q-trays to a halt for lid removal. Also, the lids are conveniently replaced on the move as well, in such a way as to avoid any requirement for precise alignment between lid and tray.

The feeder apparatus 10 may be readily adapted for the lid removal, delivery and lid replacement of other types of biological sample container. This flexibility arises from the fact that the feeder apparatus 10 is configured to handle Q-trays, which in general have the largest area, or footprint, of all relevant types of container.

Figure 7A:
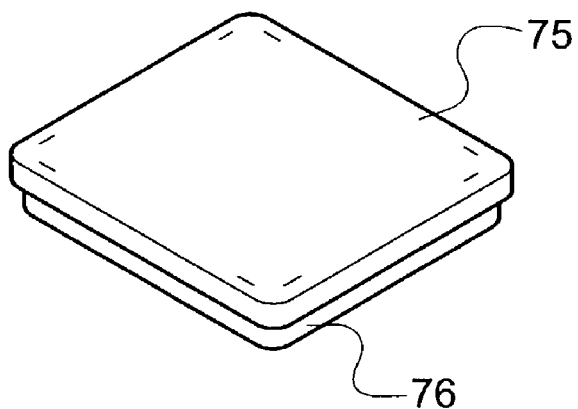
FIGS. 7(a), 7(b), 7(c) and 7(d) show perspective and cross-sectional views of biological sample containers.
Figure 7B:
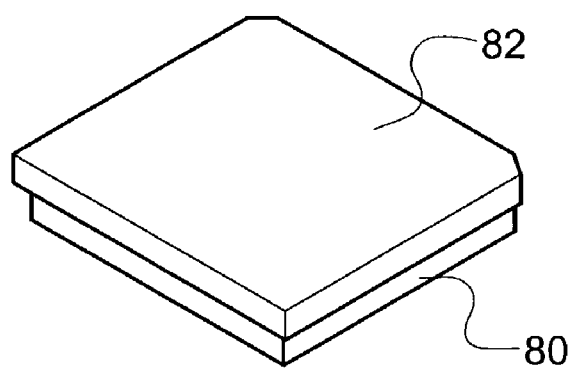
Figure 7C:
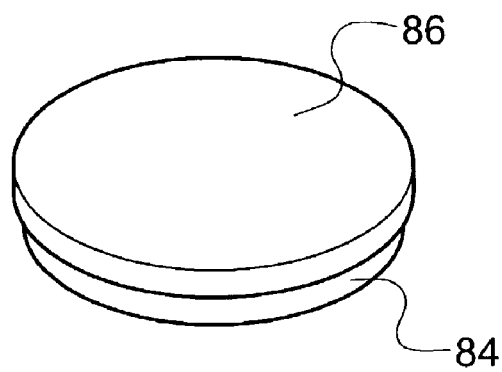

FIG. 7(a) shows a perspective view of a Q-tray 76 with its lid 75 on, illustrating that it is a large flat rectangular tray with rounded corners and an overhanging lid as described above. FIG. 7(b) is a perspective view of a container type known as an omni-tray. This is also a flat rectangular tray 80 with a lid 82, but it has a footprint less than half that of a Q-tray 76, as it measures 128 mm by 86 mm. It has two adjacent square corners, with the remaining corners being truncated. FIG. 7(c) is a perspective view of a petri dish 88, which is a round container with a lid 90 and a diameter of 88 mm. Therefore, it has a footprint of a size such that four petri dishes can fit within the area of a Q-tray.

Figure 7D:
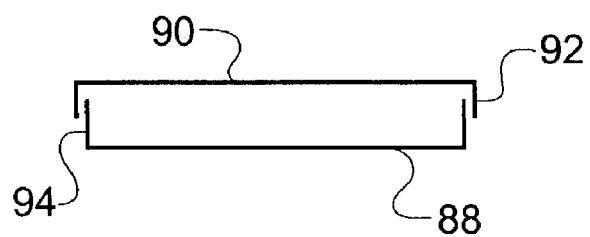

Both the omni-tray and the petri dish have overhanging lids of the same type as the Q-tray. FIG. 7(d) shows a simple cross-section of a container 88 having such a lid 90. The lid 90 fits over the container 88 so that its side walls 92 overhang the container 88 but do not reach all the way down the side 94 of the container 88. This lid design means that a ramp arrangement similar to that used in the feeder apparatus 10 to remove lids from Q-trays can also be used to remove lids from omni-trays and petri dishes. The ramp arrangements operate on the same principle as that used with Q-trays, but are more closely spaced to handle smaller containers.

The Q-tray feeder apparatus 10 can handle other containers if a holder to hold the containers is provided. The holder is a flat plate the same size and shape as a Q-tray, and having shallow depressions or recesses in its upper surface of a shape corresponding to the shape of the containers.

Figure 8A:
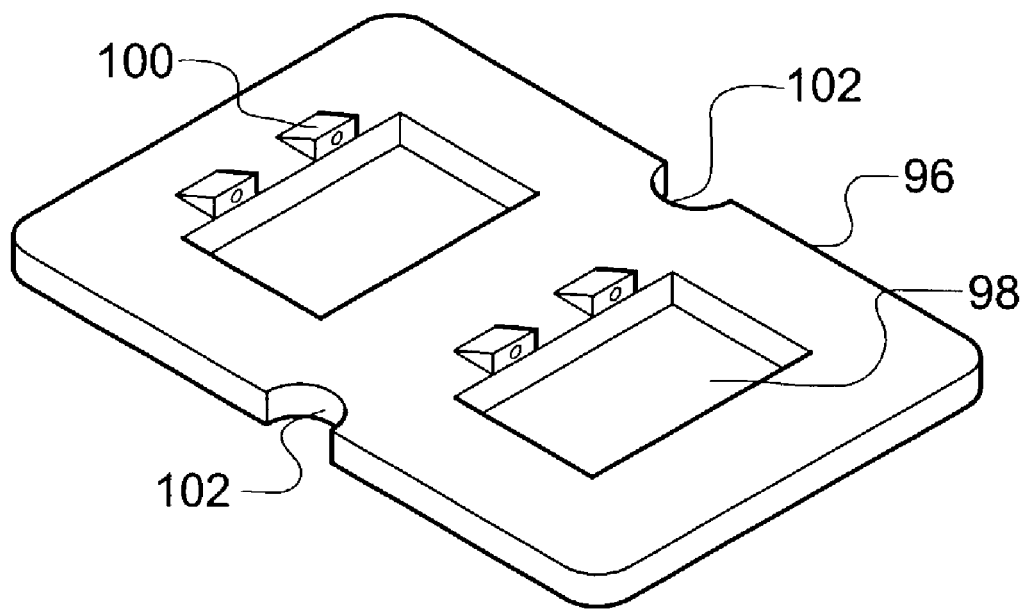
FIGS. 8(a) and 8(b) show perspective views of an embodiment of a holder for holding biological sample containers according to the invention.

FIG. 8(a) shows a perspective view of a holder 96 for handling omni-trays. The holder 96 is made from plastics material and has two shallow rectangular recesses 98 for receiving two omni trays. Along one edge of each recess 98 there are two supplementary dogs 100 having the form of abutments which abut the rear surface of omni-trays and their lids when placed in the depressions. The supplementary dogs 100 are spring-loaded so that they are urged forwards against the omni-tray lid when that is in place, and then move forwards further to abut the wall of the omni-tray after the lid is removed. The supplementary dogs 100 therefore hold the omni-tray firmly in position so that it does not move during colony picking. The holder 96 has a finger slot 102 in each side to facilitate picking up of the holder 96.

Figure 8B:
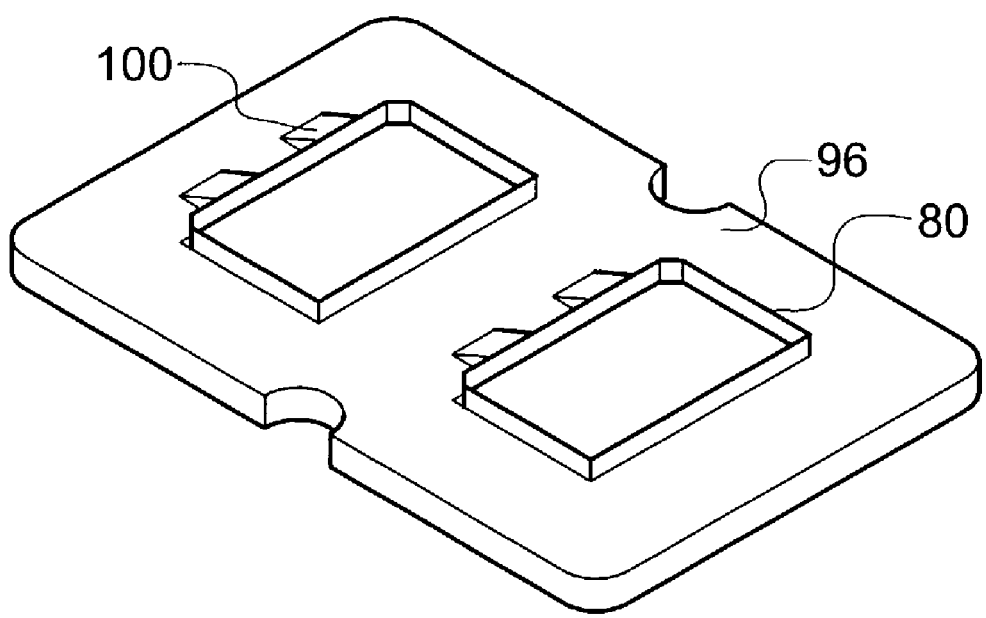

FIG. 8(b) shows a perspective view of the holder 96 containing two omni-trays 80 without lids. The omni-trays are located one behind the other with respect the direction in which they are carried through the lid-handling apparatus. Therefore, the lid-handling apparatus needs to be able to accommodate two lids, and remove and replace the lids one at a time as the respective omni trays pass between the conveyors.

Figure 9:
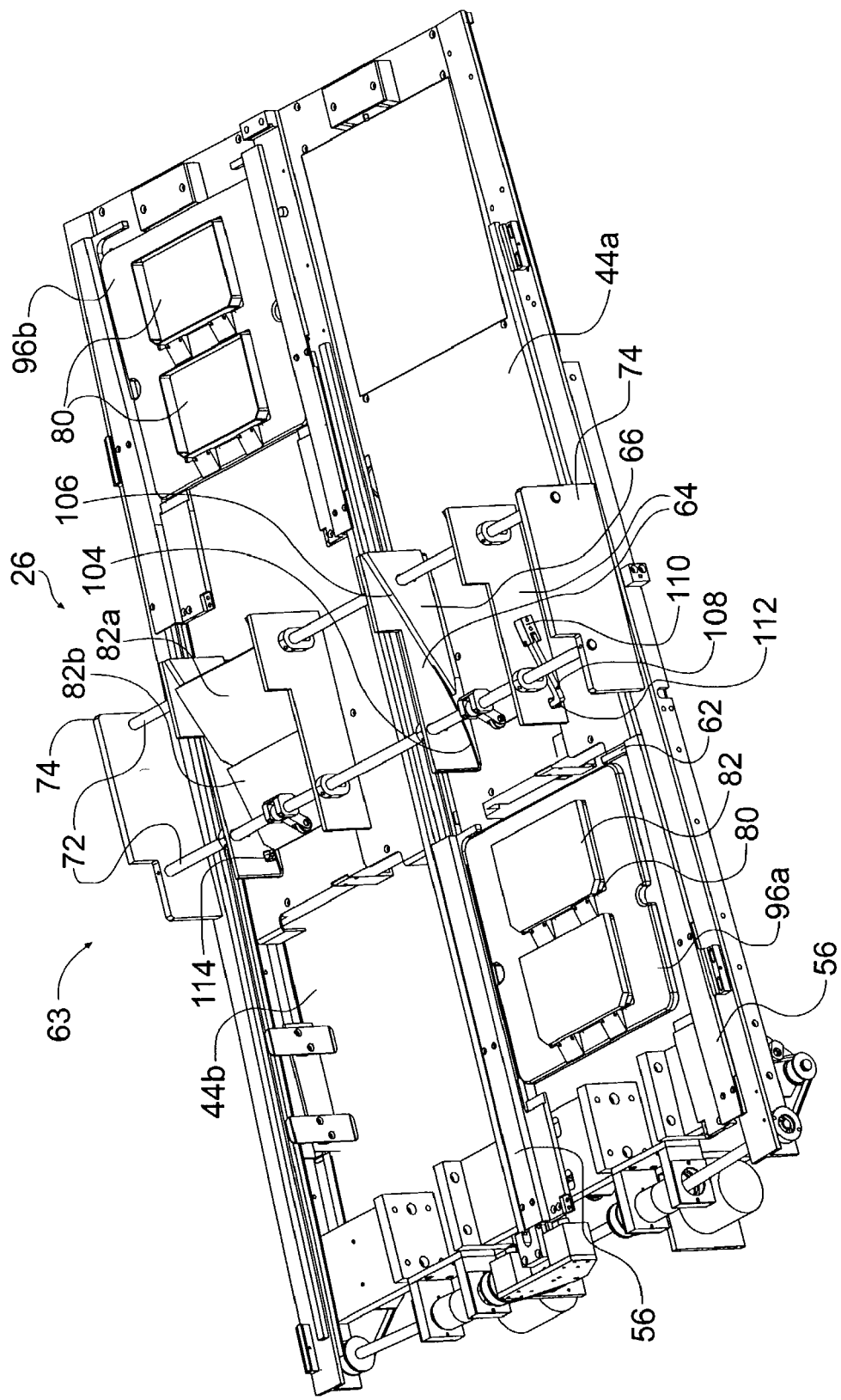
FIG. 9 shows a perspective view of a further embodiment of a conveyor assembly.

FIG. 9 is a perspective view of a conveyor apparatus 26 adapted to handle omni-trays. As the omni-trays are held in holders which are the same size and shape as Q-trays, the elevators 34 and conveyors 44 can handle the omni-trays with no modifications. The only adaptation necessary is to the lid-handling assembly 63, to provide ramps and walls which are suitably spaced. Therefore, the conveyor assembly shown in FIG. 9 is the same as that shown in FIG. 3 and previously described, with the exception of the lid-handling assembly 63. The conveyor assembly 26 is shown with one conveyor 44a with a holder 96a containing two omni-trays 80 with lids 82 which has just been returned to the elevator shelf 32 by the jaws 56 (the holder 96a is abutting the small dogs 62 which have just pulled it along). The other conveyor 44b shown has a holder with two omni-trays delivered to the colony picking position which have had their lids 82 removed by the lid-handling assembly 63. The conveyor assembly 26 and lid-handling assembly 63 operate in substantially the same manner as described for the Q-tray handling.

As mentioned previously, the Q-tray lid-handling assembly 63 is removably mounted on the conveyor assembly 26. Therefore, it is straightforward to replace it with a lid-handling assembly 63 configured to handle omni-trays. As before, the lid-handling assembly 63 comprises a pair of walls 64 with integral ramps 66 per conveyor 44, but they are mounted so that each of ramps 66 is spaced apart with sufficient clearance for an omni-tray to pass between them but to pick up the lid of the omni-tray. The spacing between the walls is just sufficient to accommodate the lid. Also, the height of the ramps 66 and walls 64 is such as to let the holder 96 pass underneath, but allow the ends of the ramps 66 to engage with the edges of a lid to lift it. The length of the ramps is sufficient for two omni tray lids to sit on the ramps, one behind the other. As before, the walls 64 and ramps 66 are mounted on horizontal bars 72 held in end brackets 74 which are mounted onto the conveyor assembly 26.

Again as before, the ramps 66 have two sections or portions of differing gradient. However, the omni-tray ramps 66 have an initial lower ramp portion 104 followed by a longer steeper upper ramp portion 106. The purpose of this is to give better handling of the two lids 82 which are handled by a single pair of ramps 66. During lid removal, the lid 82a of the front omni-tray is lifted and removed by the ramps 66 and sits at the bottom of the slope. As the rear omni-tray arrives, the ramps lift its lid 82b, which pushes the front lid 82a further up the ramps 66 until both lids 82 are on the ramps 66. When the lids are replaced, the steep section 104 allows the front lid 82a to slide down the ramps 66 under gravity as the rear lid 82b is removed by the returning rear omni-tray. The front lid 82a reaches the bottom of the ramp as the rear lid 82b falls onto the rear omni-tray, and is in the correct position to be picked up by the returning front omni-tray.

The lid-handling assembly 63 also comprises a retainer in the form of a spring-loaded arm 108 on each wall 64. The arm 108 is pivotally mounted at a first end on the outer side of the wall 64 in a mount 110. A second end of the arm 108 turns at an angle to the length of the arm to form a hook 112, the end of which passes through a hole 114 in the wall 64 to protrude over the ramp 66. The spring-loading lightly biases the hook 112 to protrude through the hole 114.

The arms 108 are provided to keep the lids 82 in place on the ramps 66. The front lid 82a is liable to slide under gravity down the steep section 106 and push the rear lid 82b off the ramps, which will interfere with the ability of the rear omni-tray to pick up the rear lid 82b. The arms 108 stop the lids 82 from sliding.

As the front lid 82a is lifted by the ramps 66, it abuts the hooks 112 and pushes the arms 108 outwards and away from the ramps 66, and moves up the ramps 66. The rear lid 82b then arrives and pushes the front lid 82a further up the ramps 66. When both lids 82 have moved up the ramps far enough for the rear lid 82b to have passed the hooks 112, the arms 108 spring inwards so that the hook 112 protrude over the ramps 66 again. The hooks 112 stop the lids 82 from sliding under gravity. When the lids 82 are picked up by the returning omni-trays, the pulling action of the trays on the lids 82 is sufficient to force the arms outwards again so that the lids 82 are released. Therefore, the hooks 112 on the spring-loaded arms 108 are abutments which abut the lids and keep them on the ramp, but are also movable so as to move out of the way when the lids are required to move off the ramps.

Figure 10:
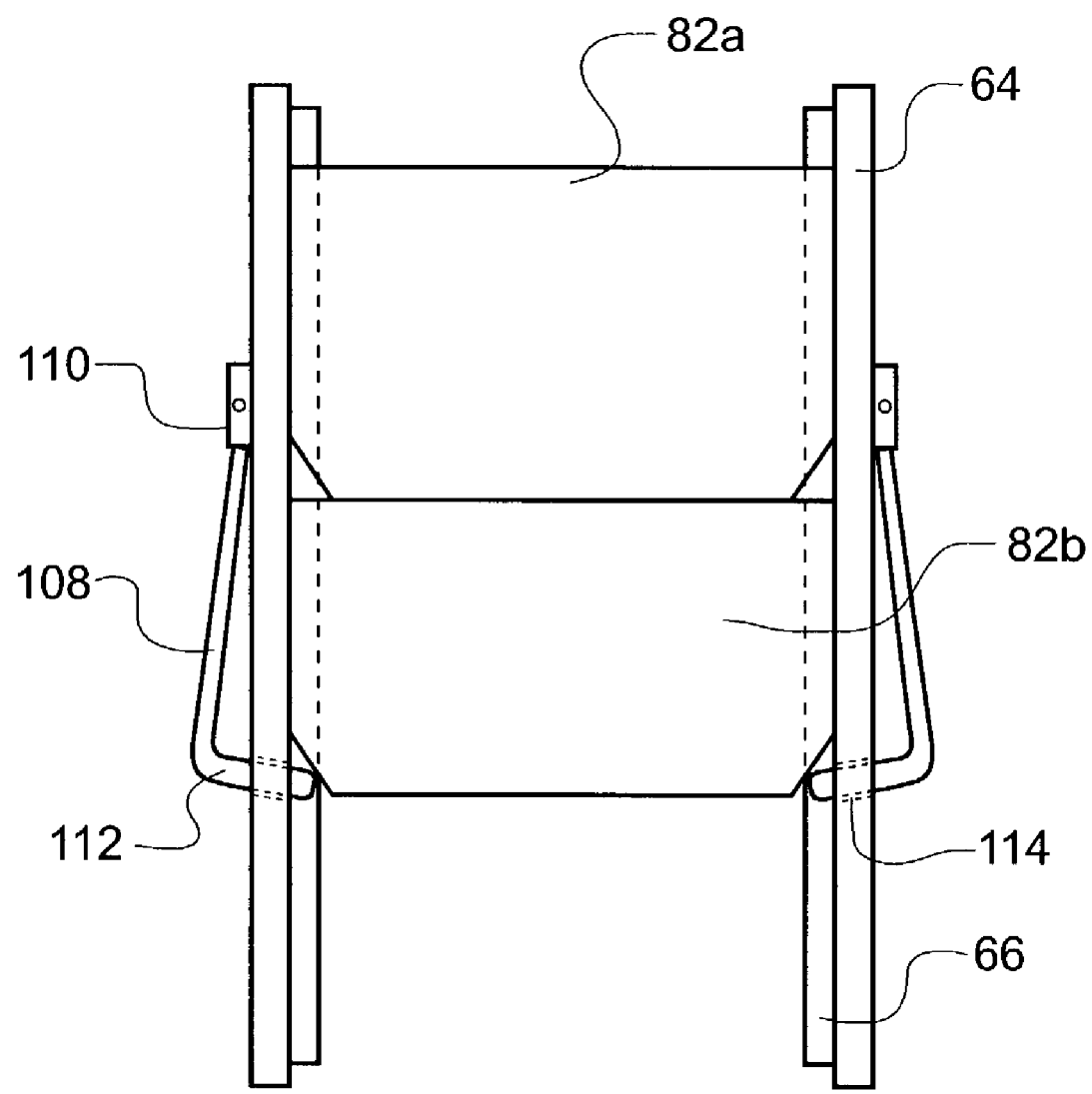
FIG. 10 shows a schematic plan view of part of the conveyor assembly of FIG. 9.

FIG. 10 is a plan view of the lids 82 held on the ramps 66 by the spring-loaded arms 112. This shows how the hooks 112 pass through the holes 114 to protrude over the ramps 66.

This arrangement allows the lids of two omni-trays held on a single holder to be removed with a single pair of ramps. The holder 96 is of a sufficient size to accommodate two omni-trays, so that four omni trays can be delivered at one time, and the elevators having twenty-five shelves each can together handle one hundred omni-trays. However, if desired, holders adapted to hold one omni-tray per holder could be provided.

Figure 11:
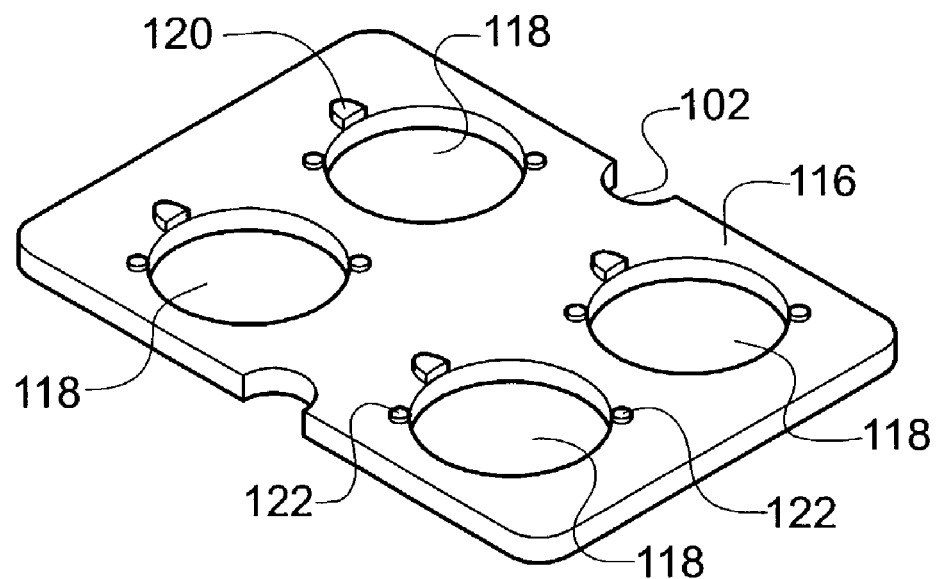
FIGS. 11(a) and 11(b) show perspective views of a further embodiment of a holder.
Figure 11:
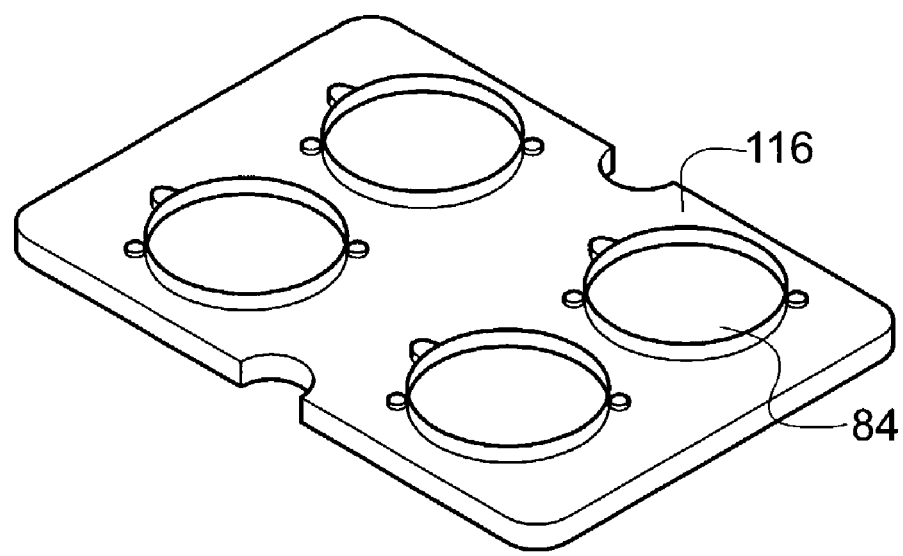

FIG. 11(a) shows a perspective view of a holder 116 for handling petri dishes. The holder 116 is made of plastic and has four shallow circular depressions or recesses 118 for receiving four petri dishes arranged in a rectangular formation. Hence two rows of two petri dishes can be accommodated. The holder 116 has a finger slot 102 in each side to facilitate picking up of the holder 116. The back edge of each recess 118 has a supplementary dog 120 in the form of an abutment which abuts the rear surface of a petri dish and its lid when the dish is placed in the recess, and acts to urge the lid up the ramps during lid removal. Each recess also has two grips comprising barbed spikes 122 positioned at its edge approximately 180° apart and protruding slightly over the recess 118. The spikes 122 hold the petri dishes firmly in position during colony picking so that they do not move within the recesses 118. The spacing of the spikes by 180° facilitates loading of the petri dishes into the holders 116, as the dishes can be slipped in from the side.

FIG. 11(b) shows a petri dish holder 116 with a petri dish 84, without a lid, held in each depression 118.

Figure 12:
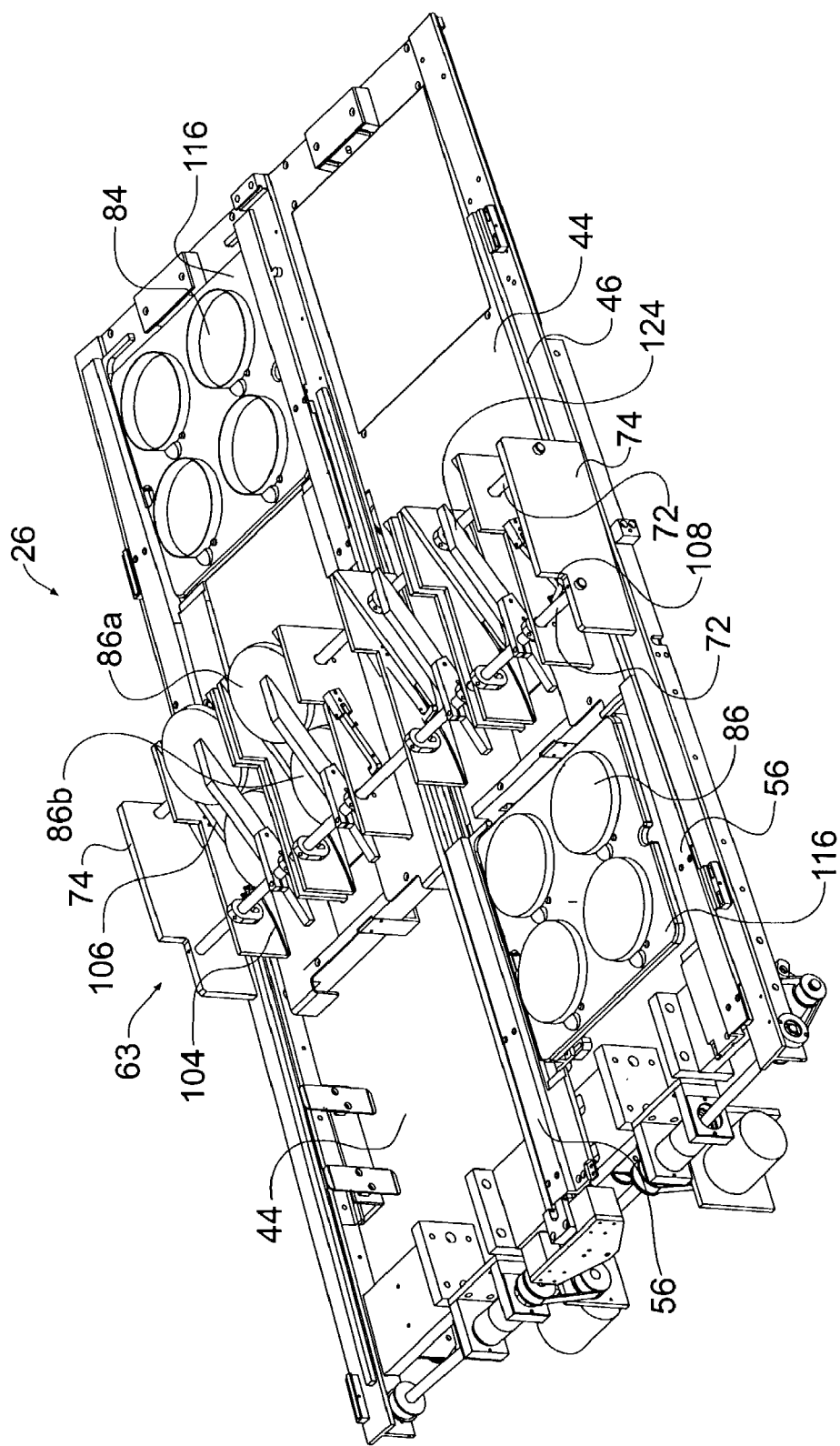
FIG. 12 shows a perspective view of a further embodiment of a conveyor assembly.

FIG. 12 shows a perspective view of the conveyor assembly 26 adapted to handle petri dishes. The holders 116 are handled in the same way as Q-trays, so that the only modification required to the assembly is the provision of a lid-handling assembly appropriate for petri-dishes.

As there are two rows of petri dishes 84 across the width of the holder 116, the lid-handling assembly 63 comprises two pairs of ramps 66 across the width of each conveyor 44, with each ramp of a sufficient size to accommodate two petri dish lids 86. As before, each ramp 66 is integral with a wall 64. Each pair of ramps 66 is positioned and spaced to engage with the lids 86 from one row of petri dishes 84, with the corresponding walls 64 spaced to accommodate the lids 86. The walls 64 and ramps 66 are at a height to allow the holders 116 to pass underneath them, and are spaced apart from the rails 46 to allow the jaws 56 to slide freely. The walls 64 and ramps 66 are held on horizontal bars 72 with end brackets 74 mounted on the conveyor assembly 26 as before.

The walls are provided with retainers in the form of spring-loaded arms 108 having hooks 112 protruding through holes 114 in the walls. These arms 108 operate in the same way as the arms described for the omni-tray lid-handling assembly, and act to keep the lids 86 up on the ramps 66. As before, the ramps 66 have an initial lower ramp portion or section 104 with a shallow gradient and a secondary upper ramp portion or section 106 with a steeper gradient. The steep slope allows the lid 86a which is held highest up the ramp 66 to slide down under gravity once the lower lid 86b is removed, but the arm is needed to prevent both lids from sliding down the ramps 66 while the lids 86 are held during the colony picking.

In addition to the lid handling features already described for the Q-tray and omni-tray lid handling, the petri dish lid handling assembly has a fixed guide arm 124 positioned above each pair of ramps 66. Each guide arm 124 is held on one or both of the horizontal bars 72 midway between the corresponding pair of ramps 66. The underside of each guide arm 124 is shaped to approximately follow the slope of the ramps 66, but the guide arm 124 is positioned so the its underside is in a plane which is spaced apart from the plane of the ramp slope by a distance slightly greater than the height of a petri dish lid. Therefore, when the lids 86 are on the ramps 66, a guide arm 124 is positioned slightly above the top surface of the lids. The guide arms 124 act to keep the lids 86 sitting flat on the ramps 66. As the lids 86 are round, there is only a small part of the edge of a lid 86 in contact with each ramp, these parts being on opposite sides of the diameter of the lid 86. Hence, the lids 86 can pivot or rock on the ramps 66, and possibly ride up over one another, which would interfere with lid removal and replacement. The guide arms 124 are provided to prevent this, by confining the lids so that they are not able to pivot enough to cause any problems of this type.

Figure 13:
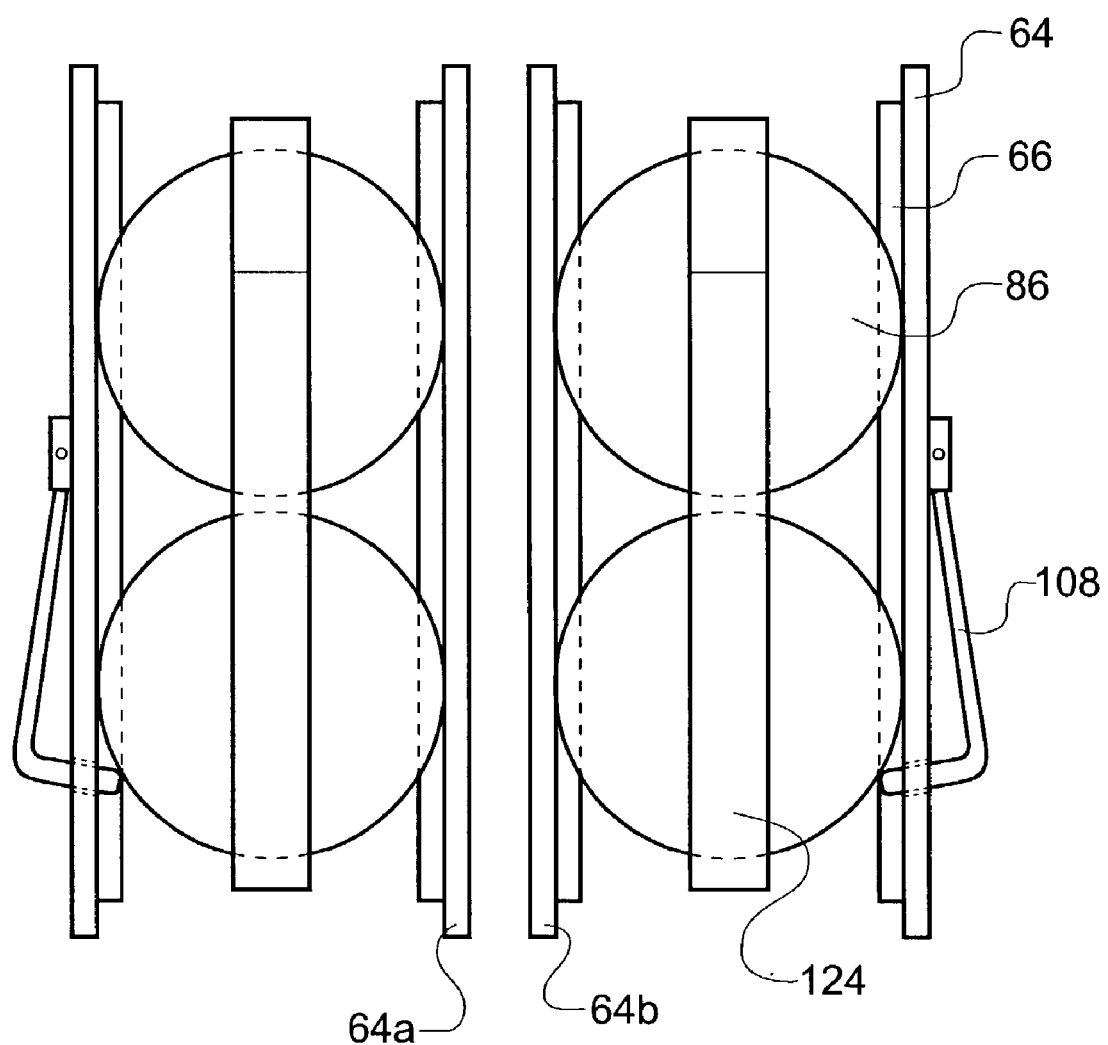
FIG. 13 shows a schematic plan view of part of the conveyor assembly of FIG. 12.

FIG. 13 is a simplified plan view of four petri dish lids 86 which have been removed from their dishes, the dishes being held in a single holder, and which are held on ramps 66 of the lid handling assembly. The spring-loaded arms 108 stop the lids 86 from sliding down the ramps 66. There is only one spring-loaded arm 108 per pair of ramps 66; this is because there is insufficient space between the two central walls 64a, 64b to accommodate arms of this type. However, a similarly-operating but more compact spring-loaded catch device could be used if it was found that the lids needed to be held on both sides.

This embodiment of the feeder apparatus is thus capable of delivering up to eight petri dishes for colony picking at one time, and removing and replacing their lids quickly on the move. The two elevators with twenty-five shelves each can hold up to two hundred petri dishes in the relevant holders.

The ease with which the container feeder apparatus can be adapted to handle different container types means that the apparatus can be supplied with just one lid handling assembly so that the apparatus is suitable for use with a particular container type, or with a plurality of lid handling assemblies so that a user may configure the apparatus to his particular requirements as any time.

The feeder apparatus 10 can be modified to handle a greater or lesser number of containers. For example, a greater number of elevator shelves can be provided per elevator. Also, the apparatus could be provided with more than two conveyors and two elevators, which would increase the number of containers which could be delivered at one time. On the other hand, a more compact apparatus with one conveyor and one elevator would be suitable for lower volume container handling. To provide further flexibility, the control of the apparatus can be configured to allow the conveying devices to be driven independently, so that any selected conveyor or conveyors can be used at a given time.

A further alternative is that the apparatus could be configured to accommodate larger holders, rather than holders of the same shape and size a Q-tray. For example, holders large enough to hold six petri dishes, or three omni trays could be provided. Holders having recesses to hold Q-trays would be required to allow an apparatus configured in this way to handle Q-trays. The use of larger holders permits a larger volume of containers to be handled. It is necessary to provide ramps having sufficient length to accommodate the number of lids which are to be conveyed through the lid handling assembly at one time.

Holders having recesses of other shapes and sizes can be provided to allow the apparatus to handle other types of container. Lid handling assemblies similar to that described are suitable for any container having an overhanging lid of the type illustrated in FIG. 7(d).

However, there are biological sample containers which do not have overhanging lids, but which are commonly used for arraying. Well plates or micro-tite plates are examples of such containers. The lid handling assemblies described so far are not suitable for these containers, as there is no overhang on the lid for the front, lower end of the ramps to engage under to lift the lid. Therefore, a different arrangement is required to provide for lifting a non-overhanging lid onto the ramps. However, once on the ramps, lid removal can proceed as described for overhanging lids, and lid replacement can be achieved in the same way as for overhanging lids.

Second Embodiment

Figure 14:
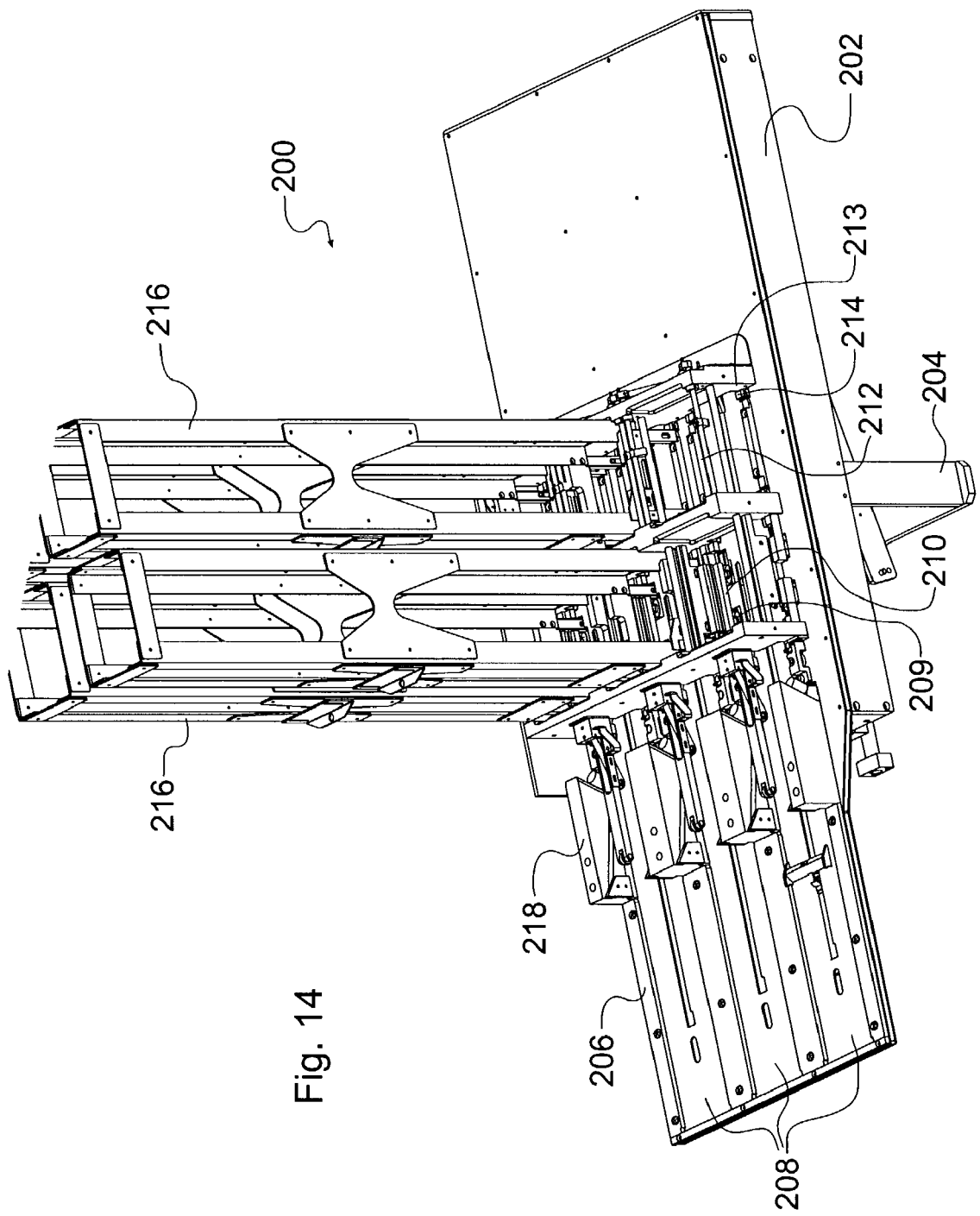
FIG. 14 shows a perspective view of an embodiment of a well plate stacker apparatus according to the invention.

FIG. 14 shows a perspective view of a well plate stacker apparatus which is operable handle containers in the form of well plates so as to sequentially deliver a quantity of stacked well plates and retrieve and restack the plates in sequence. The apparatus removes the lids of the well plates on delivery and replaces the lids on retrieval.

The well plate stacker apparatus 200 comprises a flat bed 202 which is provided on its lower surface with a bracket 204 by which the apparatus may be bolted to further apparatus (not shown). One end of the flat bed 202 is provided with a delivery, or conveyor, bed 206. The delivery bed 206 has three parallel delivery, or conveyor, lanes 208 which extend longitudinally along the delivery bed. Each of the delivery lanes 208 is provided with a lid handling assembly 218. Each lid handling assembly is located adjacent to the respective feed port 209 of each delivery lane 208, with the delivery lanes 208 extending beyond the lid handling assembly 218.

Towards the centre of the flat bed 202 at one end of the delivery lanes 208 there are arranged three feed ports 209, one for each of the delivery lanes 208. Each feed port 209 comprises a framework adapted to receive the lower end of an upright cassette 216. Each feed port 209 is provided with a release mechanism in the form of two escapement mechanisms 210. Behind each feed port 209 there is located a stacking port 212, each stacking port 212 being in line with one of the delivery lanes 208. Each stacking port 212 also comprises a framework adapted to receive the lower end of a cassette 216. Each stacking port 212 is provided with a plurality of lifting members 214, which are vertical rods of square cross-section.

Each of the cassettes 216 is identical. However, the feed ports 209 and stacking ports 212 are configured such that cassettes inserted into the feed ports sit at a lower height than cassettes in the stacking ports 212. In FIG. 14, two of the feed ports 209 are shown with a cassette 216 inserted therein, as are two of the stacking ports 212.

Figure 15:
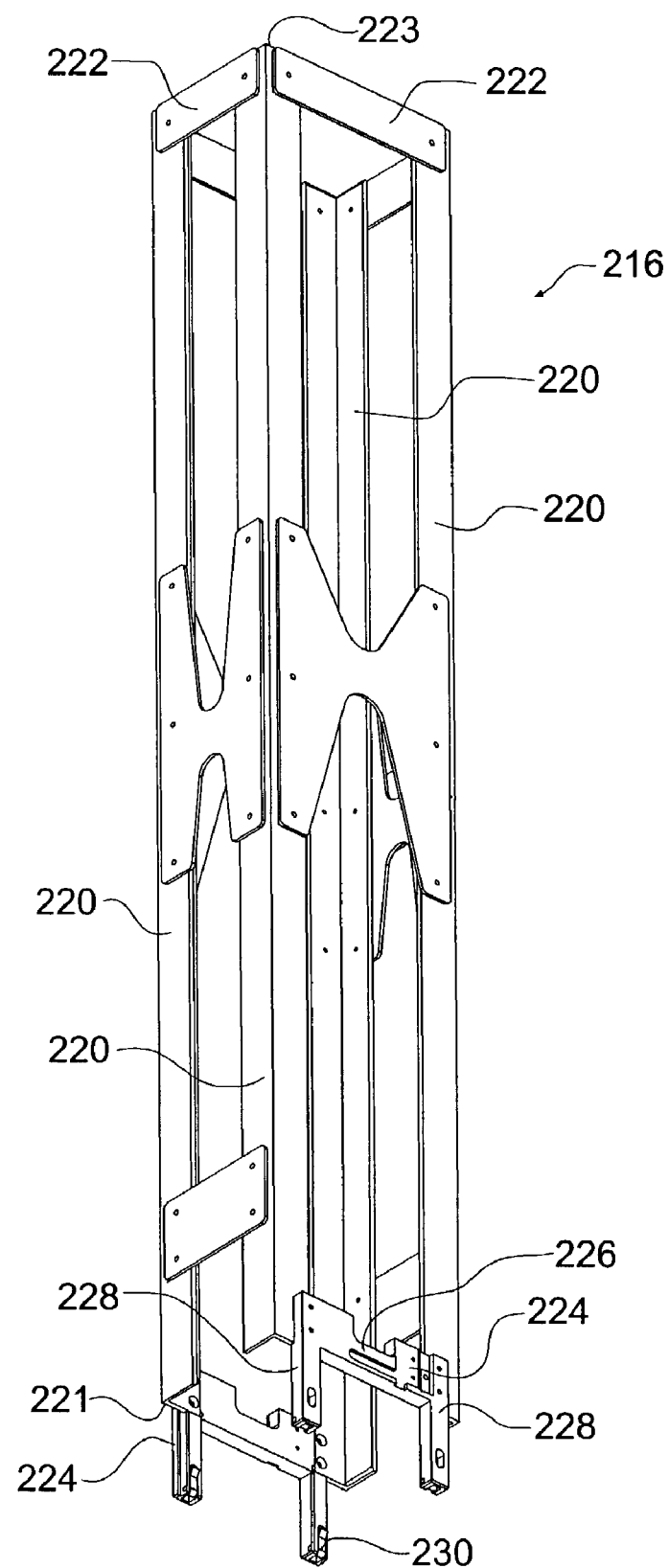
FIG. 15 shows a perspective view of a cassette for holding well plates for use with the apparatus of FIG. 12 according to the invention.

FIG. 15 shows a cassette 216 in more detail. The cassette 216 is elongate and has the general shape of a rectangular prism. The cassette 216 comprises an external framework which has four elongate upright members 220 which define the edges of the cassette. The upper ends 223 of the upright members 220 are joined together by cross-pieces 222. The lower ends 221 of the upright members 220 define a supporting portion on which the cassette 16 can sit. The lower ends 221 are provided with leg portions 224. There are two leg portions 224, each having a cross-bar 226 connecting two adjacent upright members 220. Each cross-bar 226 has a leg 228 extending downwardly from each of its ends, such that there is one leg 228 provided for each of the upright members 220. The upright members 220, the cross-pieces 222, and the leg portions 224 define a receptacle which is adapted to receive a quantity of well plates stacked on upon the other. The cassette 216 shown is configured to hold fifty well plates, but cassettes of a size to hold a greater or lesser number of well plates may be provided if desired. The well plates may be inserted into the cassette through its upper end defined by the cross-pieces 222, or from underneath, or through the sides. To retain the stack of well plates within the cassette, each of the legs 228 has on its inside surface a spring-loaded latch 230.

Figure 16:
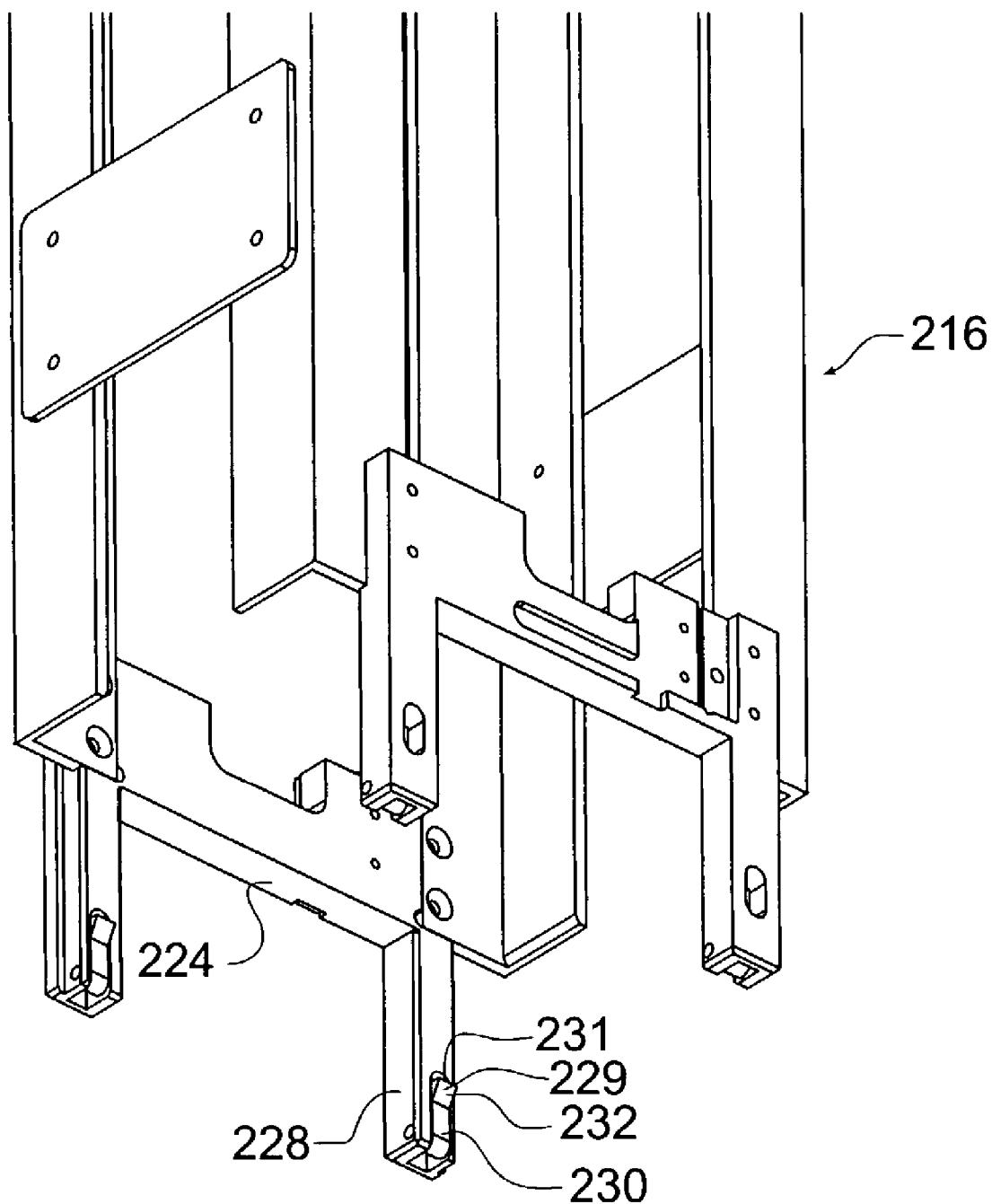
FIG. 16 shows an enlarged perspective view of part of the cassette of FIG. 15.

FIG. 16 shows a perspective view of the lower end of the cassette 116, including the leg portions 224 and the latches 230, in more detail. The latches 230 each have a small movable protrusion 232 which protrudes into the inner volume of the cassette 216. The latches 230 are spring-loaded such that the protrusions 232 are biased in this protruding position. Each protrusion 232 has a support surface 231 and a second surface 229. The support surface 231 faces upwards and is in contact with the lower surface of the bottom-most well plate of a stack held within the cassette 116. Therefore, the support surfaces 231 support the stack of well plates within the cassette 216. The second surface 229 forms an obtuse angle to the support surface 231 and faces generally inwards and downwards. The spring-loading of the latch 230 is configured such that pressure on the second surface 229 causing the protrusion 232 to move backwards and into its respective leg 228 so that it no longer protrudes into the cassette volume. Hence the latches 230 may be released, allowing well plates within the cassette 216 to fall out from the bottom of the cassette 216. The cassette 116 of FIG. 16 has four latches, but a greater or smaller number may be provided as appropriate, depending on the weight of the stack of well plates which are to be supported within the cassette.

Figure 17:
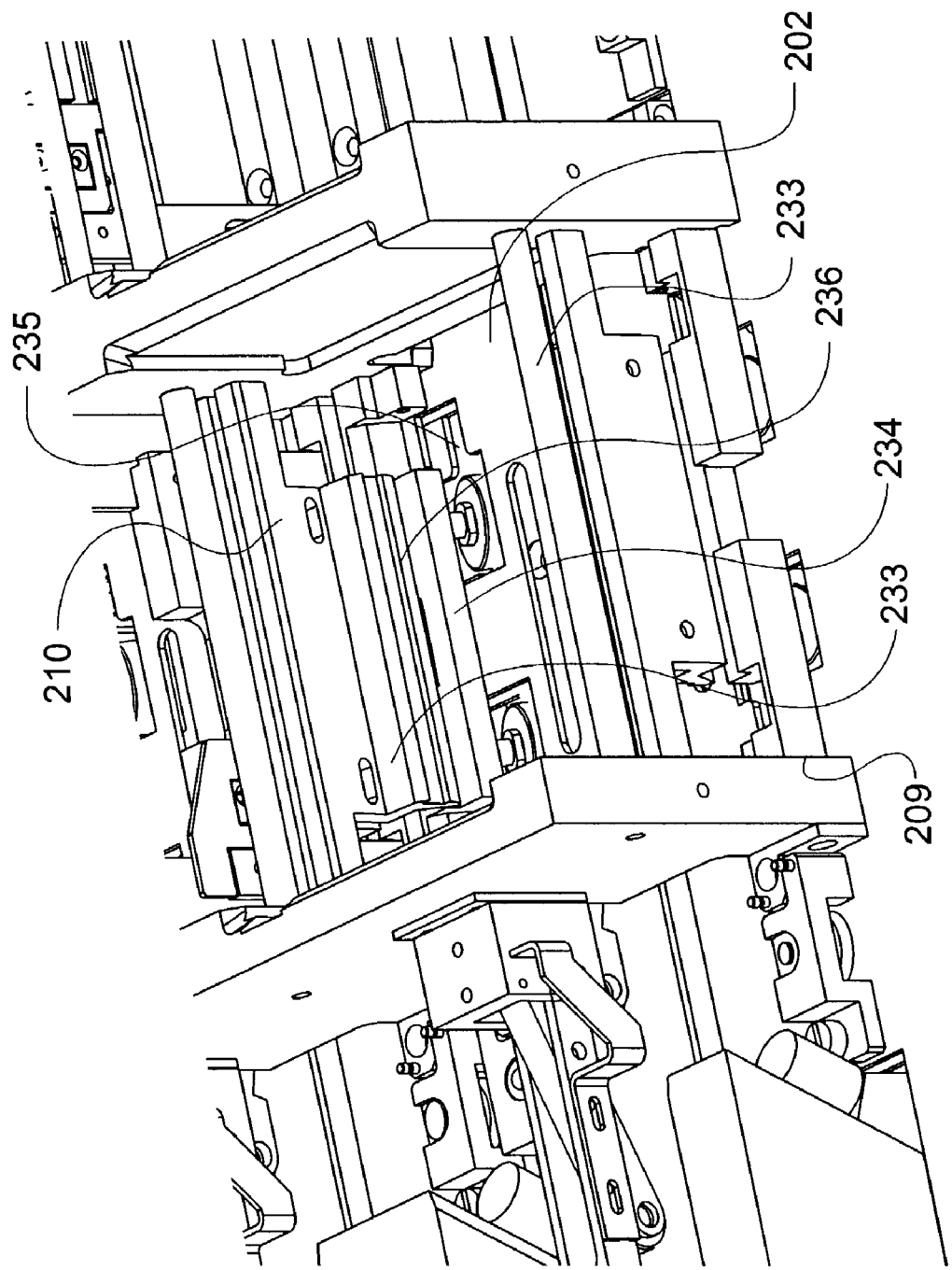
FIG. 17 shows an enlarged perspective view of part of the well plate stacker apparatus of FIG. 14.

FIG. 17 shows a feed port 209 in more detail. The flat bed 202 forms the bottom surface of the feed port 209. The feed port 209 is substantially rectangular and there are four apertures 235 in the flat bed 202 located one towards each of its corners. The apertures 235 are placed such that a cassette 216 placed into the feed port 209 will sit with its lower end 221 located against the flat bed 202 and its legs 228 protruding through the apertures 235.

The two sides of the feed port 209 which are parallel to the direction of the delivery lane 208 are provided each with an escapement mechanism 210. Each escapement mechanism 210 comprises an elongate hinged member 233 which is moveably fastened within the feed port 209 such that it is hinged about an axis parallel to the delivery lane 208. The lower end of the hinged member 233 has a supporting flange 234 which protrudes a little way into the feed port 209. The separation of the flanges 234 on each escapement mechanism 210 is less than the width of a well plate. Each hinged member 233 is further provided with a elongate gripping portion 236 which runs along the length of the hinged member and is located above the supporting flange 234 and spaced therefrom by a height substantially equal to the height of one and a half well plates. The gripping portion 236 has a rubber surface. The separation between the gripping portion on one escapement mechanism 210 and gripping portion 236 on the opposite escapement mechanism 210 is slightly more than the width of a well plate.

When a cassette 216 containing well plates is inserted into the feed port 209 the legs 228 of the cassette pass through the apertures 235 so that the latches 230 are underneath the flat beds 202. The supporting flanges 234 catch on the bottom-most well plate of the stack of well plates held within the cassette 216, and support the stack within the cassette 216. Hence when a cassette 216 is in this position, the well plates held therein are not supported on the latches 230, but instead on the flanges 234 of escapement mechanisms 210.

Figure 18:
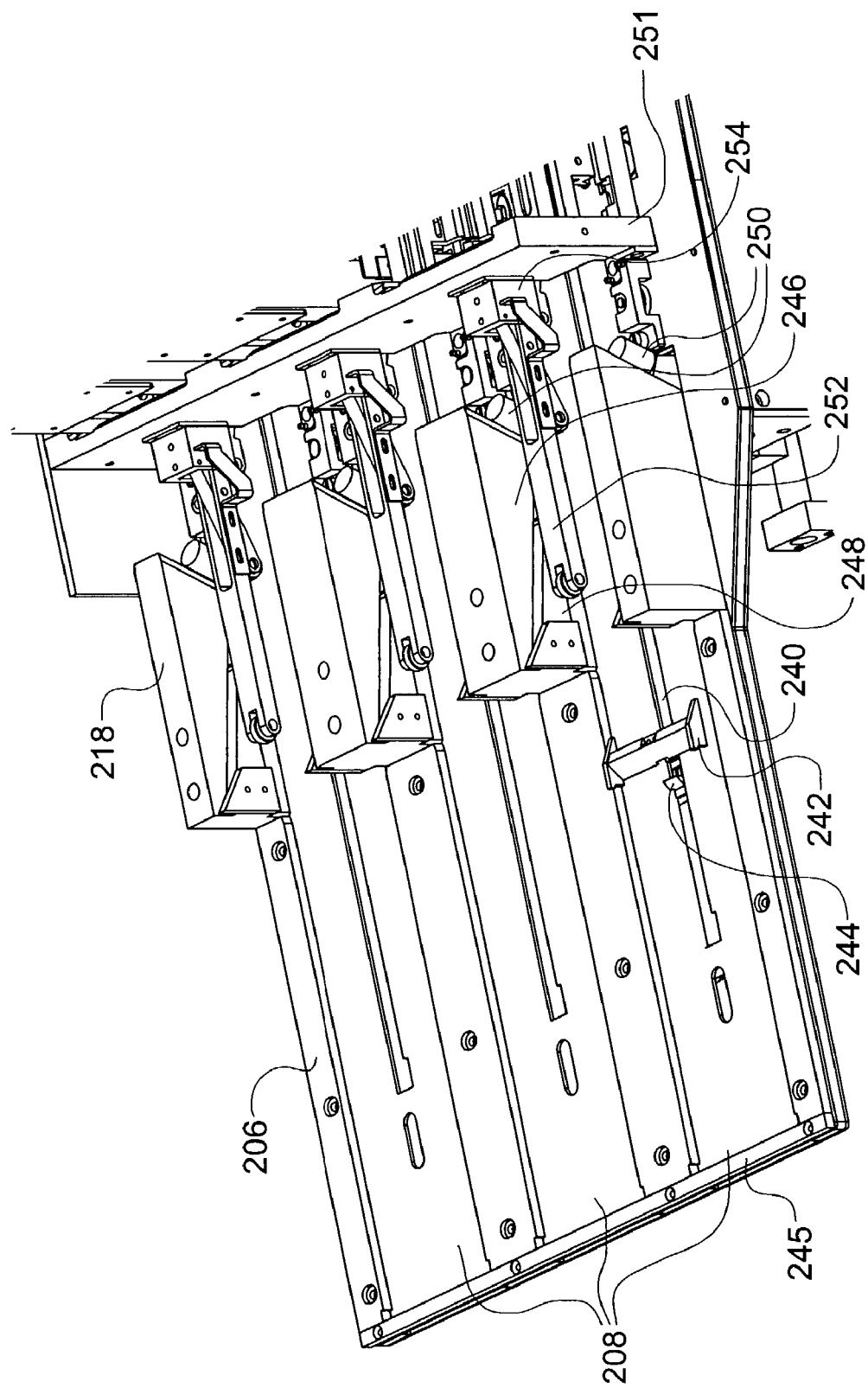
FIG. 18 shows an enlarged perspective view of an embodiment of a conveyor assembly of the apparatus of FIG. 14.

FIG. 18 shows a perspective view of the delivery bed 206 in more detail. Each of the three delivery lanes 208 of the delivery bed 206 are substantially identical. Each delivery lane 208 has a longitudinal slot 240 running along its centre and terminating before the ends of the delivery lane 208. Each delivery lane 208 has a stop-bar 245 running across its end. Each delivery lane 208 also has a movable pushing dog 242 and a pick-up catch 244. The pushing dog 242 and the pick-up catch 244 are operable to move along the length of the slot 240, and are driven by means of a sliding plate located on the underside of the delivery beds 206. The pushing dog 242 and the pick-up catch 244 are connected through the slot 240 to the sliding plate. The sliding plate is driven by a motor (not shown) via a worm drive. A belt drive could also be used. The pick-up catch 244 has two positions, one being a picking up position, which is shown in FIG. 18, in which it protrudes above the slot 240, and the other position being an inoperable position in which it lies below the plane of the delivery bed 206 and does not protrude through the slot 240. The pushing dog 242 and pick-up catch 244 can be moved from a home position indicated by reference numeral 213 on FIG. 14 to the end of the slots 240, at which point the pushing dog 242 is spaced from the stop bar 245 by approximately the length of a well plate. The pushing dog 242 is spring-biased against the sliding plate such that it is urged in a direction towards the stop-bar 245.

Each delivery lane 208 also has a pair of walls 246 located one on each side of the delivery lane 208, and facing one another. The inner surface of each wall 246 has a ramp 248 which extends upwards from a lower ramp end closest to the feed ports 209 towards the stop-bar 245.

A roller 250 is located at the lower end of each ramp 248. Each roller 250 is mounted on an axle such that the roller is freely rotatable thereon, and is mounted at an angle such that its axis of rotation is substantially perpendicular to the slope of the ramp and parallel to the sides of the walls 246. The angle may typically between 1° and 10° or between 1° and 5°, for example, 4°. Each roller 250 comprises a plurality of ball races stacked one upon the other, and surrounded by a tubular sleeve of a rubber material having a high coefficient of friction, such as santoprene. The axles of the rollers 250 extend through the delivery bed 206 and are mounted on spring-loaded mounts such that the rollers 250 are biased towards the slot in their respective delivery lane 208, but can move under light pressure on the axle in a direction substantially perpendicular to the slot 240 and away from the slot 240. When in the biased position each roller 250 is spaced from the roller 250 on the opposite ramp 248 by a distance which is a few millimetres less than the width of a well plate. The spring-loaded nature of the mounts allows the rollers 250 to be pushed apart to a separation of more than the width of a well plate lid. The rollers provide a lifting mechanism which acts to lift a lid onto the ramps, as will be described later.

An overhead bar 251 extends across the width of the delivery bed 206 and is situated between the feed ports 209 and the ramps 248 and rollers 250. The overhead bar 251 forms a wall of the feed ports 209. The overhead bar 251 is spaced above the delivery bed 206 at a height to give sufficient clearance for a well plate to pass underneath. On the overhead bar 251 there are fastened a plurality of mounts 254, one above each delivery lane 208. Protruding from each mount 254 is an overhead arm 252 which extends along the axial direction of the delivery lane 208. Each overhead arm 252 is hingedly mounted in its mount 254 such that it is hinged about an axis parallel to the plane of the delivery bed 206 and perpendicular to the length of the delivery lanes 208. Each overhead arm 252 is spring-loaded within its mount 254 such that it is biased to a position in which the free end of the arm is located at a height substantially the same as the height of the ramps 248 at the ends of the arms 252. Under light pressure, however, each arm 252 is able to move on its hinge such that its free end moves upwards.

Figure 19:
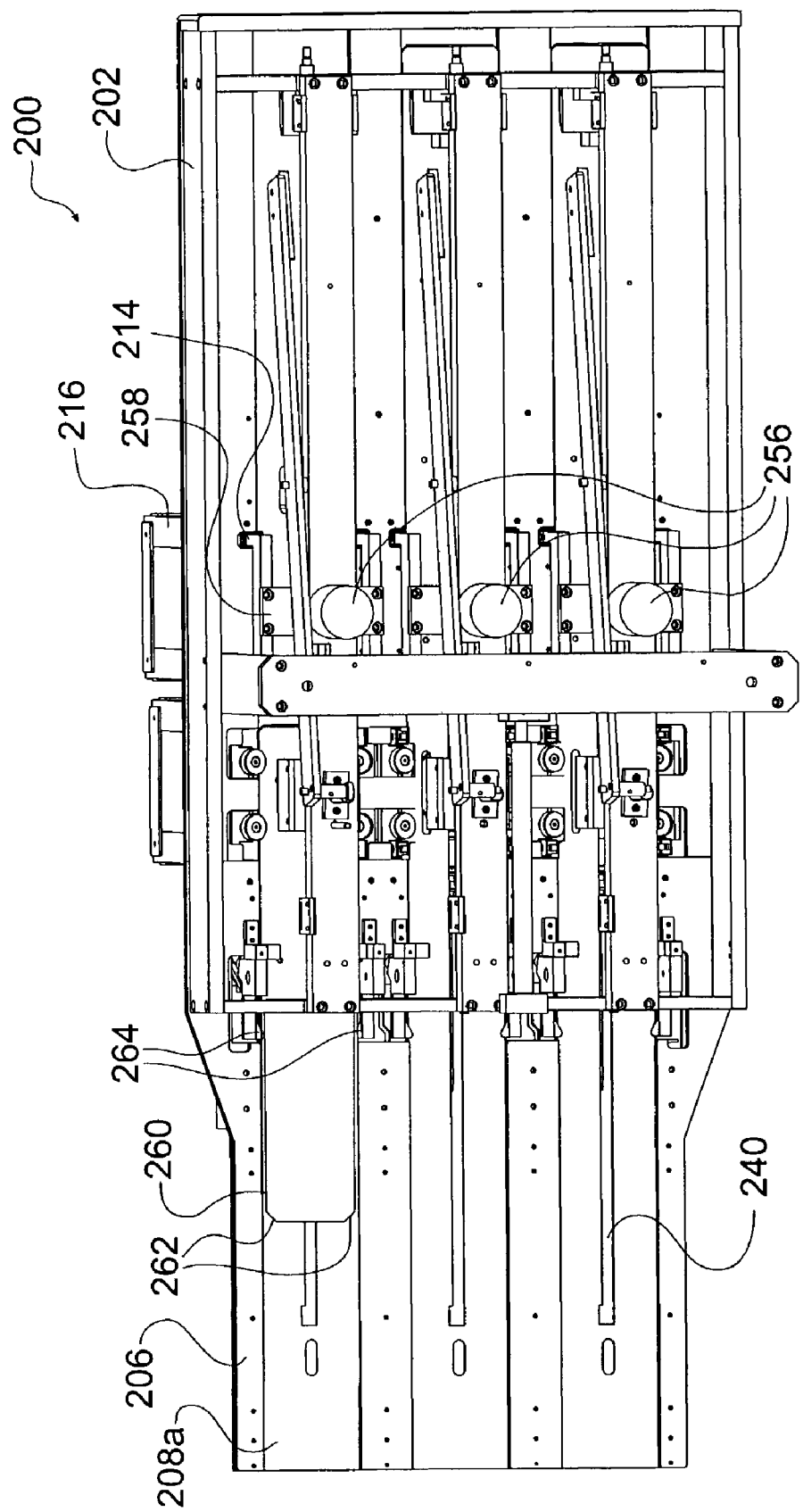
FIG. 19 shows a further perspective view of the well plate stacker apparatus of FIG. 14.

FIG. 19 shows a perspective view of the underside of the well plate stacker apparatus 200. The cassettes 216 may be seen protruding above the apparatus 200. Beneath each stacking port 212 is located a pneumatic piston 256 which is movable in a vertical direction. Each piston 256 has a connecting plate 258 attached to its upper end; the connecting plate 258 connects the piston 256 to the four lifting members 214 of that particular stacking port 212. Operation of the pistons 256 therefore moves the lifting members 214 up and down. The piston 256 and lifting members 214 comprise a lifting device or transfer mechanism.

Also shown in the Figure are the spring loaded arm mounts 264 of the rollers 250.

Also shown is the sliding plate 260 of one of the delivery lanes 208(*a*). The sliding plate 260 is a flat elongate plate having tapered corners 262 on its end facing towards the stop bar 245. The width of the sliding plate 260 at this end, between the tapered corners 262, is less than the spacing of the roller mounts 264 when in their biased position. The full width of the plate behind these front corners, however, is wider than the spacing of the roller mounts 264, so that when the sliding plate passes between the roller mounts 264 the mounts 264 and hence the rollers 250 mounted thereon are pushed apart so that the spacing between them is increased. The length of the sliding plates 260 is such that the roller mounts 264 and rollers 250 are maintained in this pushed apart position even when the sliding plate 260 has moved the pushing dog 242 mounted thereon to its extreme position.

The well plate stacker apparatus 200 is configured to handle well plates. These plates are containers for holding biological samples, and have within them a quantity of small wells or depressions arranged in a regular matrix pattern. Well plates typically have the same dimensions as the omni-trays discussed earlier, so have a footprint of 128 mm by 86 mm.

Figure 20:
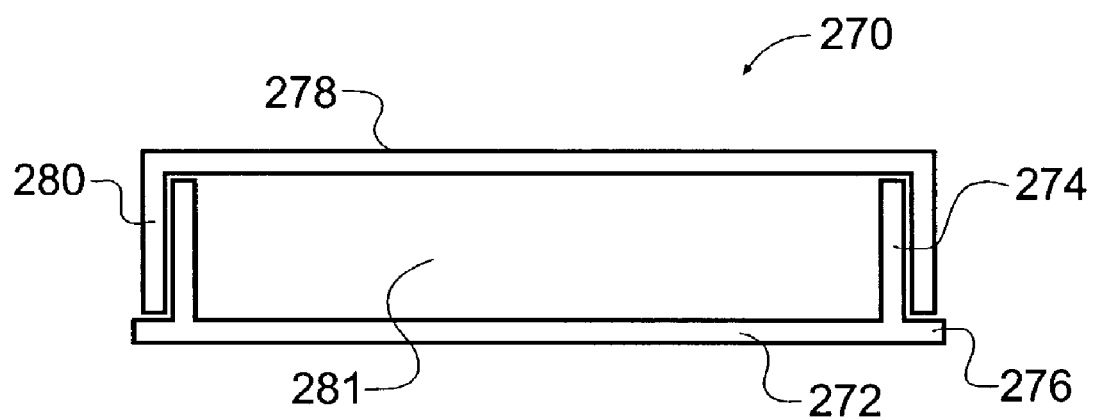
FIG. 20 shows a cross-sectional view of a well plate.

FIG. 20 shows a cross-sectional view of a well plate 270. The well plate comprises a base 272 from which a side wall 274 extends upwards. A flange 276 extends outwardly from the bottom of the side wall all the way around the well plate 270. The well plate 270 has a lid 278 which has the form of a flat surface with a side wall 280 extending downwardly around its edge. The lid 278 fits over the well plate 270 such that the side wall 280 of the lid 278 encompasses the side wall 274 of the well plate 270, and extends downwardly to meet the flange 276. Therefore, there is no overhang to the lid of the well plate 270. The interior 281 of the well plate 270 contains a quantity of wells as described above. The well plate has a rectangular footprint. Well plates are also known in the art as micro-tite plates.

The well plate stacker apparatus 200 is controlled by a computer controller (not shown), which operates the motors which drive the sliding plates 260. The apparatus 200 is provided with two microswitches per delivery lane 208. One of the microswitches controls the escapement mechanism 210, and the other microswitch controls the piston 256. The microswitches are activated by movement of the pushing dogs 242 on their sliding plates 260, as will be described in more detail later.

Operation of the well plate stacker apparatus 200 will now be described.

One, two or three cassettes 216 are filled with well plates. Each cassette 216 holds up to fifty well plates, although cassettes holding a larger quantity of plates may be provided if desired. Each of the filled cassettes 216 is inserted into a feed port 209 of the apparatus 200. As previously described, the legs 228 of the inserted cassette 216 protrude through the apertures 235 in the feed ports 209, so that the bottom-most well plate in the stack rests on the supporting flanges 234 of the escapement mechanism 210, rather than on the latches 230 of the cassette 216.

An empty cassette 216 is inserted into each stacking port 212 which is behind a feed port 209 having a filled cassette 216. The stacking ports 212 do not have apertures 235 like those in the feed ports 209; therefore the cassettes 216 inserted into the stacking ports 212 sit with the ends of their legs 228 on the flat bed 202 of the apparatus 200.

The computer controller sends a command to initiate operation of the apparatus 200. One, two or all three of the delivery lanes 208 are selected for use as desired. For each selected lane, the command activates the motor controlling the sliding plate 260, so that the pushing dog 242 begin to move from its home position 213 behind the empty cassette 216 in the stacking port 212, towards the full cassette 216 in the feed port 209. The pushing dog 242 then passes and activates the microswitch which controls the escapement mechanisms 210.

Figure 21:
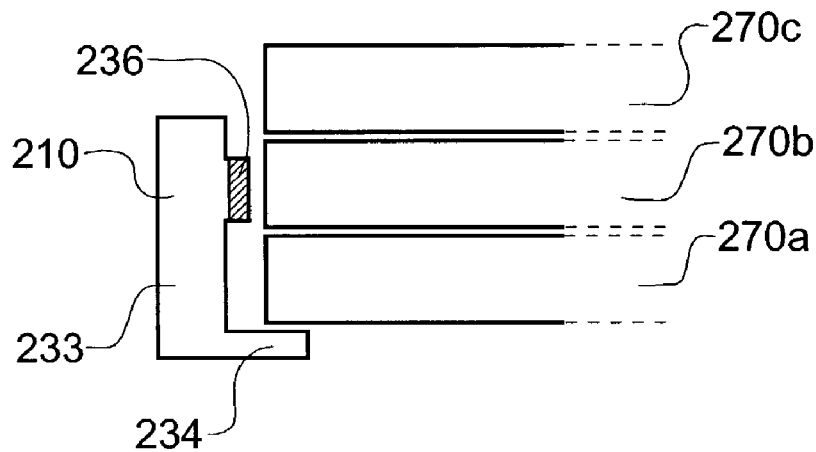
FIGS. 21(a), 21(b) and 21(c) show schematic cross-sectional views of part of the apparatus of FIG. 14 in operation.
Figure 21:
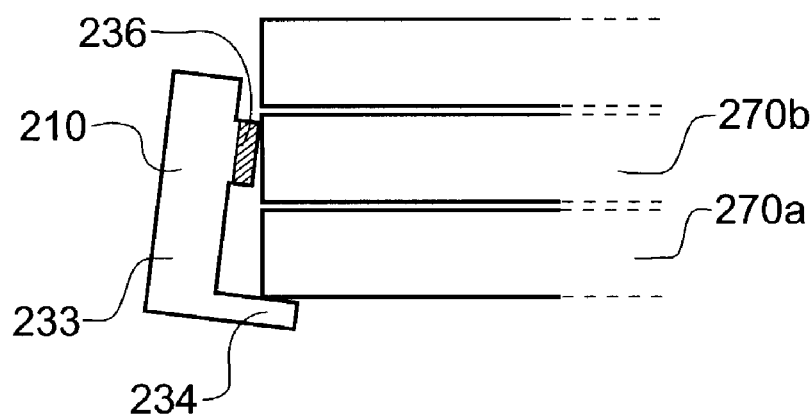
Figure 21:
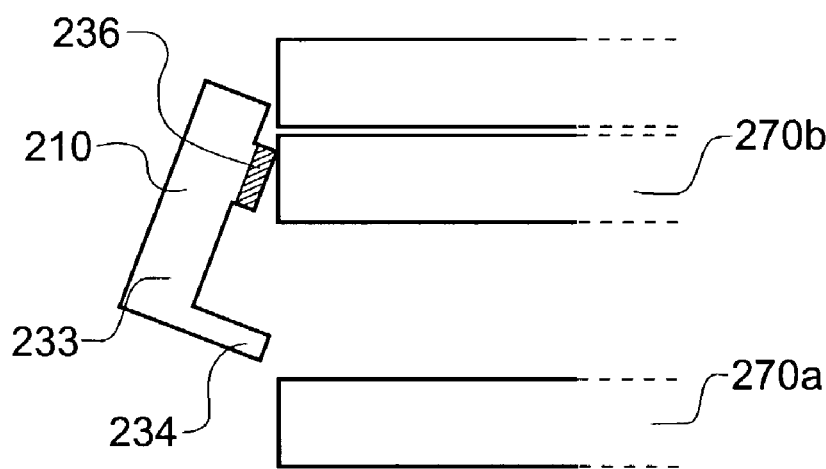

FIGS. 21(*a*), 21(*b*) and 21(*c*) are simplified cross-sectional diagrams illustrating the operation of the escapement mechanism of the feed port 209. As shown in FIG. 21(*a*), a stack of (in this example) three well plates 270 are supported on the supporting flange 234 of an escapement mechanism 210. The lowest well plate 270(*a*) rests directly on the supporting flange 234. Activation of the escapement mechanism 210 causes the hinged member 233 to pivot about its hinge such that the supporting flange 234 begins to move outwards away from the well plates 270, and the gripping portion 236 begins to move inwards towards the well plates 270. The relative sizes of the gripping portion 236 and the supporting flange 234 are such that the gripping portion 236 comes into contact with the side of the second-from-bottom well plate 270(*b*) before the supporting flange 234 has moved completely away from under the bottom-most well plate 270(*a*). Hence the second-to-bottom well plate 270(*b*) is gripped between the gripping portions 236 of the escapement mechanisms 210 on each side of it. This situation is depicted in FIG. 21(*b*). The hinged member 233 continues to pivot until the supporting flange 234 moves completely out from beneath the bottom-most well plate 270(*a*), so that this well plate falls past the supporting flange and on to the flat bed 202 at the bottom of the feed port 209 (a first position). The gripping portion 236 continues to grip the second-from-bottom well plate 270(*b*), so that the stack of well plates above this well plate is supported thereon.

While the well plate 270(*a*) is being released, the pushing dog 242 continues to move along the delivery lane 208. At this time the pick-up catch 244 is in its inoperable position and hence does not protrude above the delivery bed 206. The pushing dog 242 moves forward until it contacts the rear wall of the well plate 270 in the feed port 209 and begins to push the well plate 270 forward so that it passes underneath the overhead bar 251.

The well plate 270 then enters the lid handling assembly 218. The inclined rollers 250, on each side of the delivery lane 208, make contact with the lid 278 of the well plate 270. As the rollers 250 are spaced by slightly less than the width of the well plate lid 278, they are pushed outwards slightly by the pressure of the advancing well plate 270 and its lid 278 as allowed for by their arm mounts 264. However, the spring-biasing of the rollers 250 maintains contact between the rollers 250 and the well plate lid 278, and the rubber surface of the rollers 250 provides for high friction contact.

Figure 22:
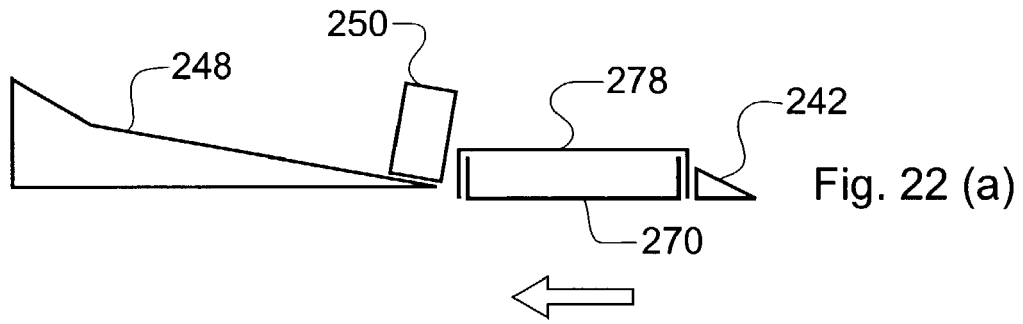
FIGS. 22(a), 22(b), 22(c) and 22(d) show schematic cross-sectional views of a lid-handling assembly forming part of the conveyor apparatus of FIG. 3.
Figure 22:
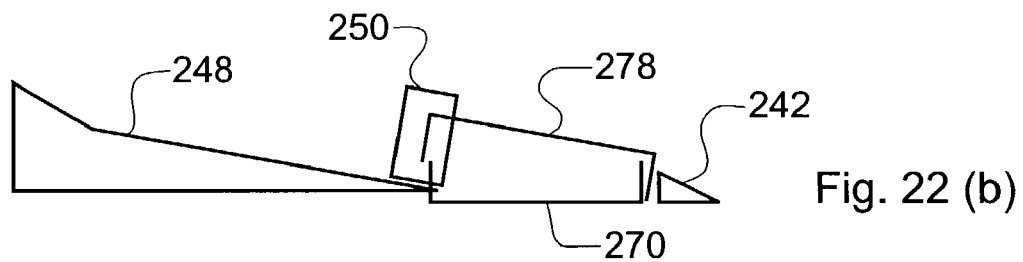
Figure 22:
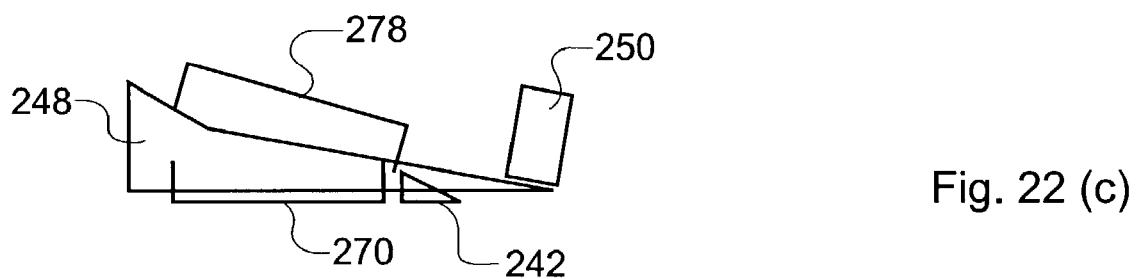
Figure 22:
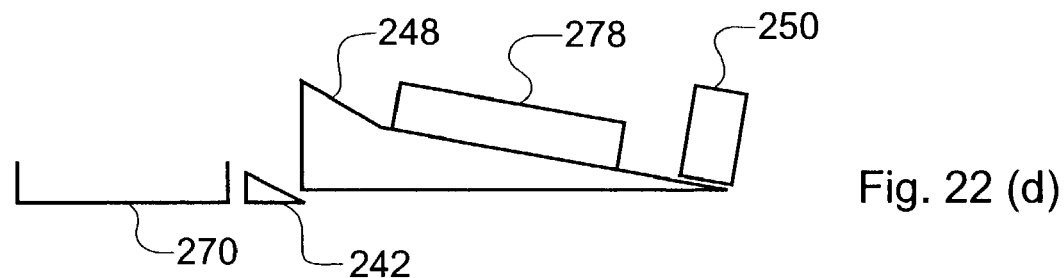

FIGS. 22(*a*), 22(*b*), 22(*c*) and 22(*d*) show simplified cross-sectional diagrams of the removal of a well plate lid 278 by the inclined rollers 250 and ramp 248. FIG. 22(*a*) shows the well plate 272 with its lid 278 being pushed by the pushing dog 242 towards the rollers 250. FIG. 22(*b*) shows a point at which the rollers 250 have begun to lift the lid 278 from the well plate 270. When the rollers 250 contact the lid 278, they begin to rotate freely about their axles, allowing the lid 278, which is being pushed by the pushing dog 242, to pass between them, and at the same time lifting the lid owing to the grip of the rollers 250 upon the lid, and the inclined axis of rotation of the rollers 250. The pushing dog 242 continues to push the lid 278 and well plate 270 forward through the rollers. The rollers continue to lift the lid and feed it out above the ramp 248.

The sliding plate 260, at this point, passes between the spring-loaded roller mounts 264 and pushes them apart. Hence the rollers 250 also move apart and release their grip upon the lid 278. The lid 278 is therefore dropped onto the ramps 248. The pushing dog 242 continues to push the well plate 270 and its lid 278 forwards, with the lid 278 proceeding up the ramp 248. Eventually the lid 278 is lifted so far up the ramp 248 that the bottom edge of its side wall is lifted above the height of the pushing dog 242, so that the pushing dog 242 ceases to push the lid 278 any further forward and merely pushes the well plate 270 forward on its own. The pushing dog 242 continues to push the well plate 270 through the lid handling assembly, so that the lid 278 remains behind sitting on the ramps 248. FIG. 22(*d*) shows this.

As the lid 278 climbs the ramps it pushes the spring-loaded overhead arm 252 upwards. However, the biasing of the overhead arm 252 keeps the free end of the arm 252 pressing down upon the lid 278, so that when the lid 278 is fully lifted onto the ramps 248 the downward pressure of the overhead arm 252 maintains the lid 278 in its lifted position on the ramps 248. Hence the overhead arm 252 acts as a retainer, to retain the lid 278 in position.

The pushing dog 242 continues to push the well plate 270 along to the end of the delivery lane 208, until the well plate 270 touches the stop-bar 245 (a second position). The spring-loaded nature of the pushing dog 242 means that the well plate 270 is maintained in tight contact with the stop-bar 245 so that the well plate 270 is securely held in position. When the second position the well plate 270 is ready to receive samples. The samples are typically delivered by a micro-arraying process, in which a movable overhead array of pins or needles pick up samples from colonies in other containers such as Q-trays, and deposit the samples in the wells of the well plate 270. This process is typically computer controlled.

Once samples have been deposited in the well plate 270, the well plate 270 is ready to be delivered back to a cassette 216. Therefore the computer controller sends a command to the motor once again, and the motor direction is reversed so that the sliding plate moves in a direction towards the feed port 209 and the stacking port 212. The reversal of the motor also activates the pick-up catch 244 so that it moves into its picking up position, protruding above the surface of the delivery bed 206. Conventional well plates have in their bottom surface a recess, into which the pick-up catch enters. Hence the pick-up catch 244 pulls the well plate 270 along the delivery lane 208. The pushing dog 242 passes under the lid 278 held on the ramps 248. However, the ramps are arranged so that rear edge of the side wall of the lid 278 is held at a height lower than the height of the side wall of the well plate 270. Therefore, the rearwardly moving well plate 270 engages with the rear wall of the lid 278 and begins to pull the lid down the ramp 248. The rollers 250 are still held in their spaced apart position owing to the sliding plates 260 forcing the spring-loaded roller mounts 264 apart, so that the well plate 270 is able to pull its lid 278 freely through the rollers 250 so that the lid 278 slides off the end of the ramp 248 and drops back onto its well plates 272. Hence the lid 278 is replaced correctly on the well plate 270.

The pick-up catch 244 continues to pull the well plate 270 so that it passes right underneath the stack of well plates held in the cassette 216 located in the feed port 209 (and hence passes through the first position). These well plates are still supported by the gripping portions 236 of the escapement mechanisms 210, so that there is ample space for the well plate 270 to pass beneath. The pick-up catch 244 continues to drag the well plate 270 until it is located underneath the empty cassette 216 positioned in the stacking port 212 (a third position). At this point, the pushing dog 242 has returned to its home position 213. The pick-up catch then returns to its inoperable position, under the flat bed 202. As the pushing dog 242 returns to the home position 213 it activates the second microswitch, which operates the piston 256. The piston 256 moves upwards so that the lifting members 214 pass through the apertures 238 in the flat bed 202 and come into contact with the lower surface of the well plate 270. The lifting members 214 continue to move upwards carrying the well plate 270 with them. The well plate lid 278 makes contact with the second surfaces 229 of the latches 230 so that the protrusions 232 on the latches 230 are pushed inside the legs 228 of the cassette 216. Hence the well plate 270 can pass beyond the latches 230, the protrusions 232 of which spring back into the protruding position once the well plate 270 has passed. The lifting members 214 are then lowered by reversal of the direction of movement of the piston 256, and the well plate 270 comes to rest on the protrusions 232 of the latches 230.

The escapement mechanisms 210 in the feed port 209 now move so that the hinged member 233 rotates back to its original position. Hence the supporting flanges 234 extend below the stack of well plates within the cassette 216 and the gripping portions 236 release the original second-from-bottom well plate 270(b) so that it falls onto the supporting flanges 234 and becomes the new bottom-most well plate in the stack. Hence the well plate stacker apparatus 200 is returned to its original configuration, with one well plate 270 per selected delivery lane 208 provided with samples and transferred to an empty cassette 216.

The computer controller is now able to send further commands to the apparatus 200 to repeat the process described above, in which the well plates 270 now at the bottom of the stacks in the cassettes 216 in the feed ports 209 are carried along the delivery lanes 208, supplied with samples, and transferred to the cassettes 216 in the stacking ports 212. Hence in this way each of the well plates is sequentially removed from its cassette 216 via the feed ports 209 supplied with samples, and transferred to a cassette 216 in one of the stacking ports 212. At the end of the process, when all of the well plates 270 have been transferred from one cassette 216 to the other, the well plates 270 are stacked in the stacking port cassette 216 in reverse order to that in which they were stacked within the feed port cassette 216. This is because each new well plate 270 is transferred to the stacking port cassette 216 by being pushed upwards by the lifting members 214 so that each successive well plate 270 passes the latches 230 and becomes the bottom-most well plate in the stack contained within the stacking port cassette 216, supported on the protrusions 232. (In fact, this is a convenient way to manually fill a storage cassette with blank well plates, e.g. by lowering the cassette over a stack of well plates arranged on a bench.)

Figure 23:
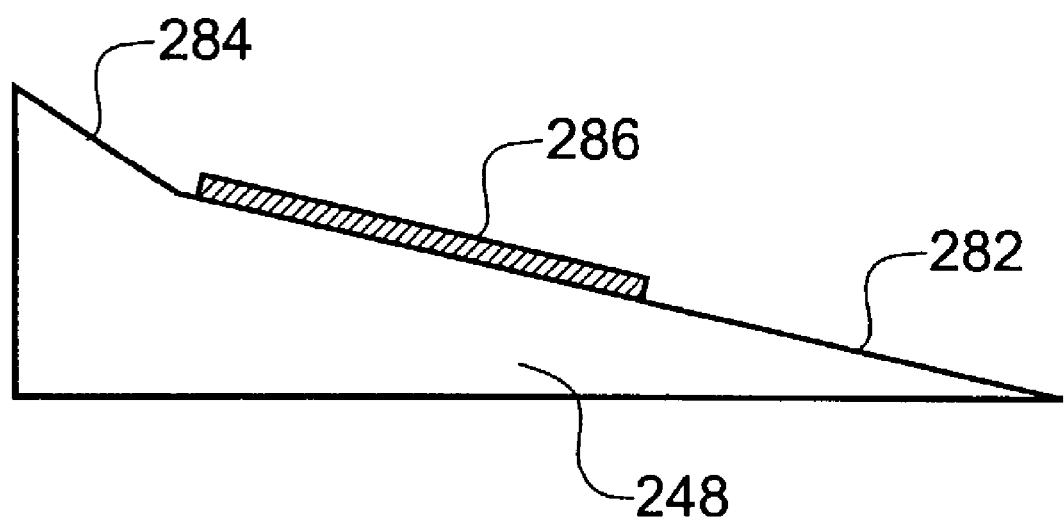
FIG. 23 shows a schematic cross-sectional view of the lid-handling assembly of FIG. 22.

FIG. 23 shows a simplified cross-section of one of the ramps 248. The sloping surface of the ramp 248 is divided into two portions, a lower ramp portion 282 and an upper ramp portion 284. The lower portion 282 has a much shallower incline or gradient than the upper portion 284. A rubber strip 286 is provided on the surface of the lower portion 282, to provide friction. As a lid 278 is removed, the rollers 250 and pushing dog 242 push the lid 278 up the ramps 248 until the front edge of the lid 278 is on the steeply inclined upper ramp portion 284. However, in order for a well plate 270 to be able to pick up its lid 278 on the return travel, it is necessary for the rear edge of the lid 278 to be lower than the height of the side wall of the well plate. To ensure that this happens, the upper portion 284 of the ramp 248 has a steep incline and a low friction surface, so that the lid can slide down the ramp 248 under gravity, until the front edge hits the rubber strip 286. Friction provided by the rubber strip 286 prevents the lid 278 from sliding right off the ramp 248, and retains the lid 278 in the correct position to be picked up by the returning well plate 270.

Therefore, the well plate stacker apparatus is able to deliver and retrieve well plates for arraying, and remove and correctly replace the lids without having to bring the moving plates to a standstill. Thus a large number of plates can be handled automatically and quickly. The apparatus as described can be modified by the provision of more delivery lanes, so that more than three well plates can be delivered at one time. Also, the delivery lanes can be operated independently, to provide flexibility for the user.

Additionally, a lid handling assembly of the type described for use with well plates, and featuring rollers to lift a non-overhanging lid, is also suitable for use with containers having overhanging lids if desired. Clearly, however, the rollers increase the complexity of the assembly, so that the use of a ramps-only configuration is to be preferred for handling overhanging lids.

Similarly, features of either the container feeder apparatus or the well plate stacker apparatus may be combined as desired, because there are features performing similar functions in each apparatus. For example, well plates may be loaded onto an elevator and conveyed using a conveying device with two clamping jaws as described for Q-trays, if the jaws are suitable sized. Alternatively, well plates are the same size and shape as omni trays, so that well plates could be held in omni tray holders and handled by the container feeder apparatus.

Third Embodiment

It is common in arraying techniques for colonies to be picked from Q-trays, omni trays or petri dishes, and transferred to well plates. Therefore, the first and second embodiments may be combined in a single arraying apparatus which is loaded with colony-containing containers and with empty well plates, and which then removes the lids and delivers the containers as required to an arraying surface where a pin array transfers samples from the containers to the well plates, and retrieves the containers after use, replacing the lids in the process.

Figure 24:
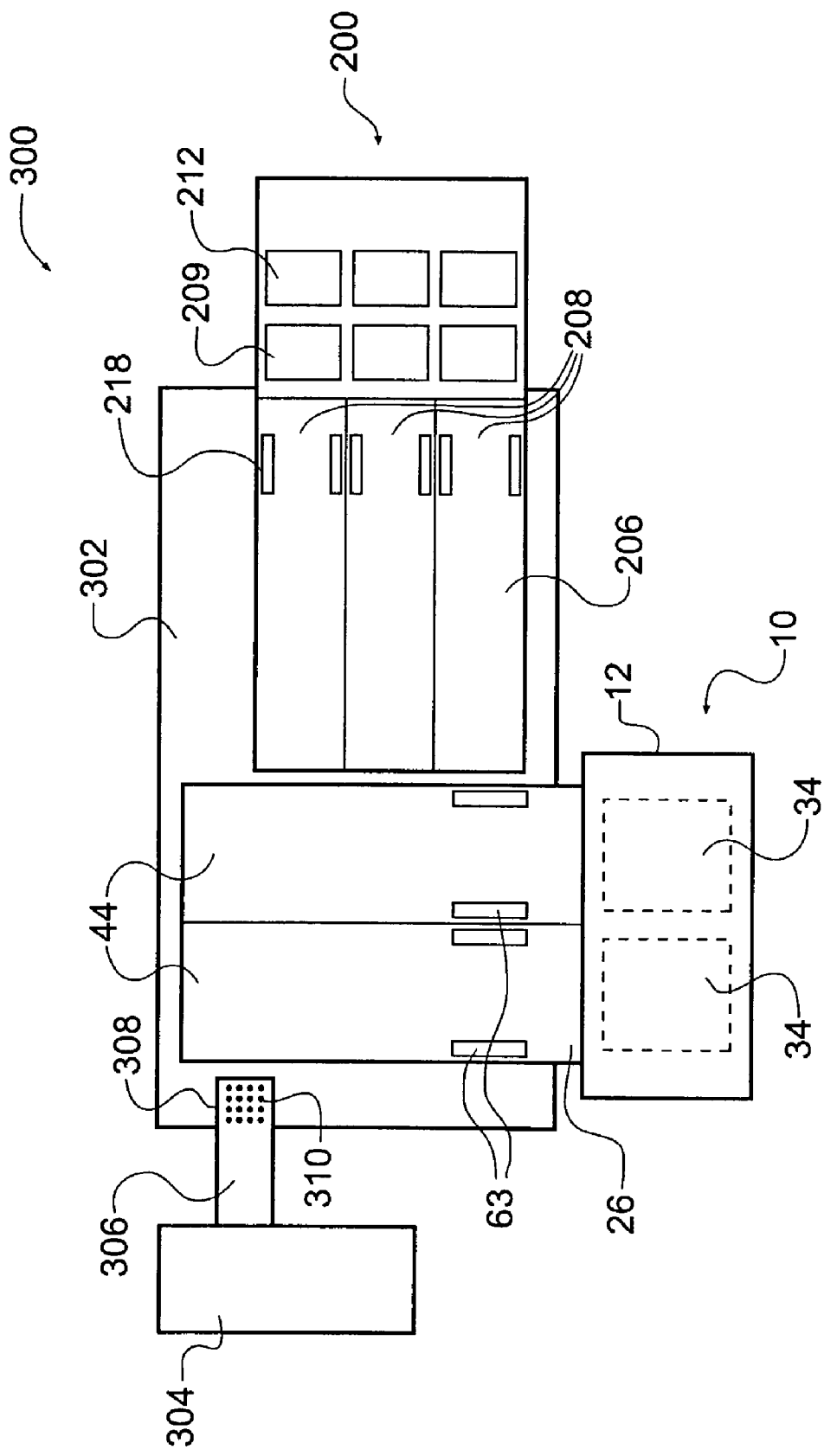
FIG. 24 shows a simplified plan view of an arraying apparatus comprising a well plate stacker apparatus according to the invention and a container feeder apparatus according to the invention.

FIG. 24 shows a simplified schematic block diagram of an embodiment of such an arraying apparatus, viewed from above.

The arraying apparatus 300 has an arraying surface 302, around which are positioned a container feeder apparatus 10 and a well plate stacker apparatus 200. The container feeder apparatus has a housing 12 containing two elevator stacks 34, and a conveyor assembly 26 having two conveyors 44 each provided with a lid handling assembly 63. The conveyor assembly 26 extends across the arraying surface 302 so that containers may be delivered from the elevator stacks 34 to the arraying surface 302. The well plate stacker apparatus 200 has a delivery bed 206 with three delivery lanes 208 each having a lid handling assembly 218. Each delivery lane has a corresponding feed port 209 and a stacking port 212. The delivery bed 206 extends across the arraying surface 302 so that well plates may be delivered from cassettes in the feed ports 209 to the arraying surface 302.

The arraying apparatus 300 also has an arraying assembly 304, which has a motorised drive system controlled by a computer, for operating an arraying arm 306 which extends above the arraying surface 302. The arm 306 terminates in a pin head 308 which holds a plurality of pins 310 arranged in a matrix, which can be dipped down into containers and plates on the arraying surface 302. The arraying arm 306 is moveable over the arraying surface 302 to an extent such that every pin 310 can reach every well in each of the three well plates delivered to the arraying surface 302 at any time, and every part of each of the containers delivered to the arraying surface 302 at any time. Hence samples can be transferred from any of the containers to any of the well plate wells. The pin head 308 also houses a camera (not shown) operable to photograph colonies in a container before arraying begins. The computer processes the photograph to calculate spatial co-ordinates of the position of the colonies on the arraying surface 302; these co-ordinates are then used to direct the arraying arm 306 so that the pins 310 accurately pick the colonies. The computer may also be used to control the well plate stacker apparatus 200 and the container feeder apparatus 10; alternatively, separate computers may be provided for this.

A pin head can also be used for gridding. In addition, a liquid handling head having an array of pipette tips could also be used. Therefore, the arraying apparatus can be considered in more general terms as providing a work surface over which a head carrying pins or pipettes can be moved, to transfer biological material between different container types.

The well plate stacker apparatus 200 and the container feeder apparatus 10 are operated in the manner described above. In other words, the conveyor assembly 26 of the container feeder apparatus 10 conveys containers from a first pick-up position within the housing 12 and delivers them, via a first lid handling assembly 63 to a first spraying position on the arraying surface 302. The delivery lanes 208 of the well plate stacker apparatus 200 convey well plates from a second pick-up position, in the feed ports 209, via a second lid handling assembly 218, so a second arraying position on the arraying surface 302. Once colony picking and arraying for these containers and well plates has been completed, the conveyor assembly 26 returns the containers to the first pick-up position via the first lid handling apparatus 63, and the delivery lanes 208 convey the well plates to a return position in the stacker ports 212, via the second lid handling assembly 218. This is repeated as necessary until as many containers as desired have been presented for arraying.

Arraying assemblies operable in the above-described manner are known. However, by combining this type of assembly with a well plate stacker apparatus and a container feeder apparatus according to the present invention, the arraying process can be speeded up significantly, allowing larger volumes of samples to be processed in less time than is possible with prior art configurations.

Further Embodiments

First Alternative Lid Handling Assembly

Figure 25:
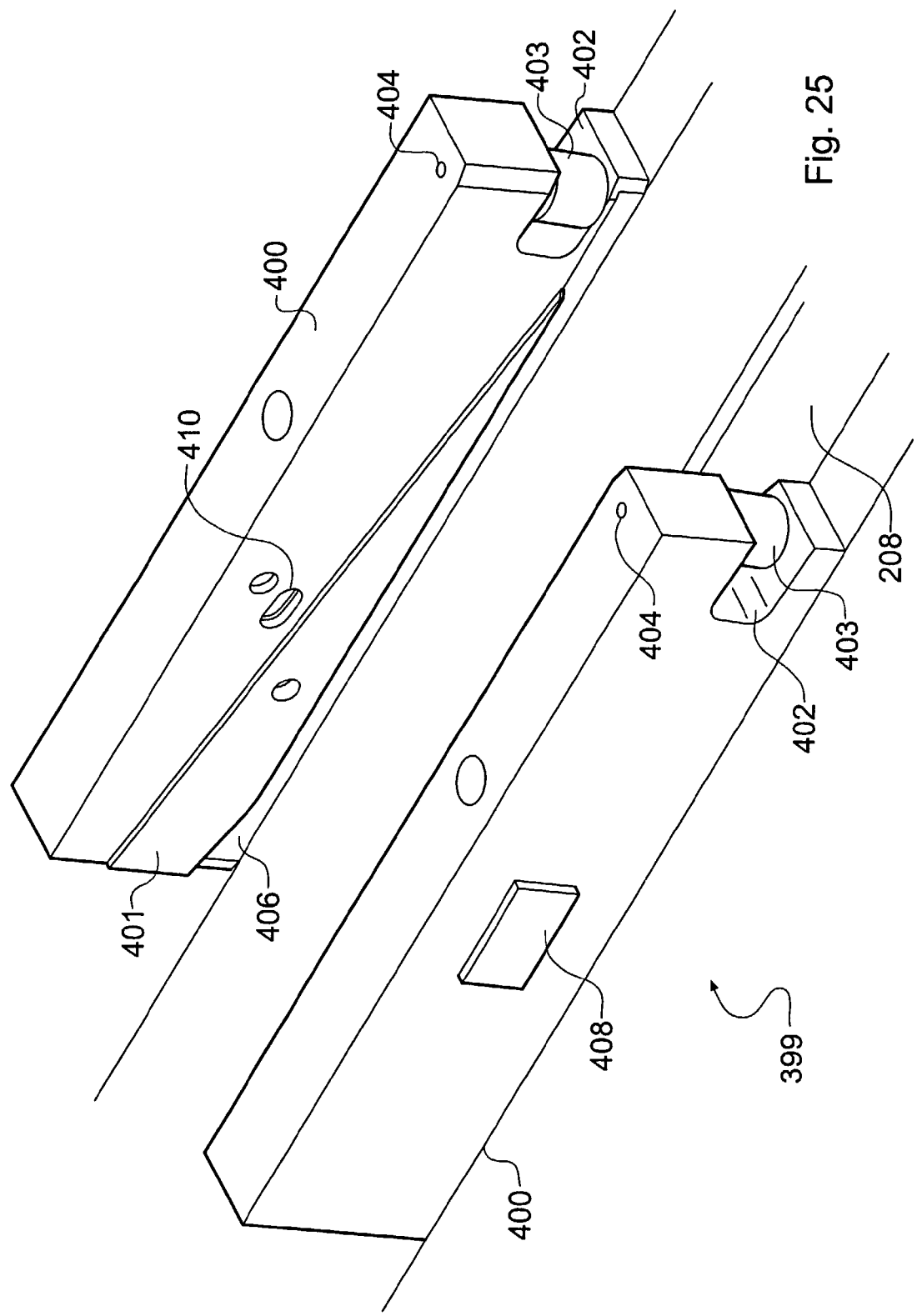
FIG. 25 shows a perspective view of a further embodiment of a lid handling assembly.

FIG. 25 shows a perspective view of an alternative embodiment of a lid handling assembly 399. Like the lid handling assembly 218 of the second embodiment, this lid handling assembly 399 uses rollers to assist lifting a container lid onto a pair of ramps.

The lid handling assembly 399 comprises a pair of elongate mounting blocks 400, arranged longitudinally one on either side of a delivery lane 208 such as those discussed previously. The sides of the mounting blocks 400 which face each other are each provided with an inclined ramp 401. The ramps 401 slope upwards in the longitudinal direction of the delivery lane 208, and protrude slightly into the delivery lane 208. The lower end of each ramp 401 is located a small distance behind one end of the respective mounting blocks 400. The ramps 401 have a bottom edge which is spaced above the surface of the delivery lane 208 so as to leave a clearance gap 406.

Each mounting block 400 is further provided with a recess 402 at its end adjacent to the lower ramp end, and longitudinally spaced apart therefrom. In each recess 402 there is mounted a roller 403, the rollers 403 being each mounted on an axle 404 on which the rollers can freely rotate. The axles 404 and rollers 403 are mounted such that the axis of rotation of the rollers is inclined at a small angle to the vertical. For example, an angle in the range 1° to 10° or 1° to 5° could be used, such as 4°. Also, the rollers protrude slightly over the delivery lane. The axles 404 are fixed to the mounting blocks 400 so that the rollers can rotate but cannot move laterally.

The lid handling assembly 399 works in a similar fashion to that described in relation to the second embodiment (see FIG. 22 and accompanying text), in that the rollers 403 act to lift a lid off a container passing between them, and feed the lid onto the ramps 401 as the container passes between the ramps 401. However, the construction and operation of the lid handling assembly 399 are simplified by the use of rollers having fixed axles. The rollers 403 are positioned such that they protrude into the path of an oncoming container only far enough to contact the lid of the container with sufficient friction to lift it. Because there is no biasing of the rollers 403 towards the lid (other than by the resilience of the rubberised roller faces), this contact is not sufficient to grip the lid between the rollers 403, and the lid is merely directed upwardly by the rollers 403. Hence there is no requirement for any kind of biasing release mechanism to separate the rollers 403 so as to drop the lid onto the ramps 401. Similarly, on the return journey, the friction between the lid and the rollers is easily overcome by the pulling or pushing force of the conveying device used to convey the container along the delivery lane, so that the lid is pulled back onto the container.

The size of the clearance gap 406 can be altered so as to accommodate larger or smaller containers and/or conveying devices. The ramps 401 need to be an appropriate distance above the delivery lane 208 for the lifting provided by the rollers 403 to be sufficient to deliver the lid onto the ramps 401, otherwise the lid will merely collide with the ends of the ramps 401 and not be removed from its container. The clearance gap 406 can be altered, for example, by the use of one or more spacer plates (not shown) beneath the mounting blocks 400, or by providing a number of alternative interchangeable mounting blocks 400 for different types of well plates. Unfortunately, there is no standardization of the outer dimensions of well plates so different pairs of blocks need to be provided for different proprietary well plate types. However, the mounting block pairs are easily mounted and demounted to allow relatively easy changeover between different well plate types.

Also shown in FIG. 25 is a lid detection system comprising an optoelectronic transducer 408 mounted on one of the mounting blocks 400, and an optical source 410, such as an LED, mounted on the other mounting block 400. Each of these components is mounted at a height less than the depth of a lid above the respective ramp 401. The transducer 408 is arranged to detect light emitted by the optical source 410 and deliver an electronic signal in response. The electronic signal from the transducer 408 can be fed to a computer or control circuit used to control the apparatus of which the lid handling assembly 399 forms a part. The presence of a lid on the ramps 401 will interrupt the light emitted by the optical source 410 and hence the transducer 408 will not detect anything. This arrangement thus detects the presence or absence of a lid on the ramps 401, and allows problems to be indicated. For example, the apparatus can be halted, or an alarm given, if a lid fails to be properly deployed onto the ramps 401 or returned to its container.

This optoelectronic system is an alternative to a microswitch-based system.

This lid handling assembly 399 can be used with containers having overhanging or non-overhanging lids, including well plates, Q-trays, omni-trays and petri dishes.

Second Alternative Lid Handling Assembly

Figure 26:
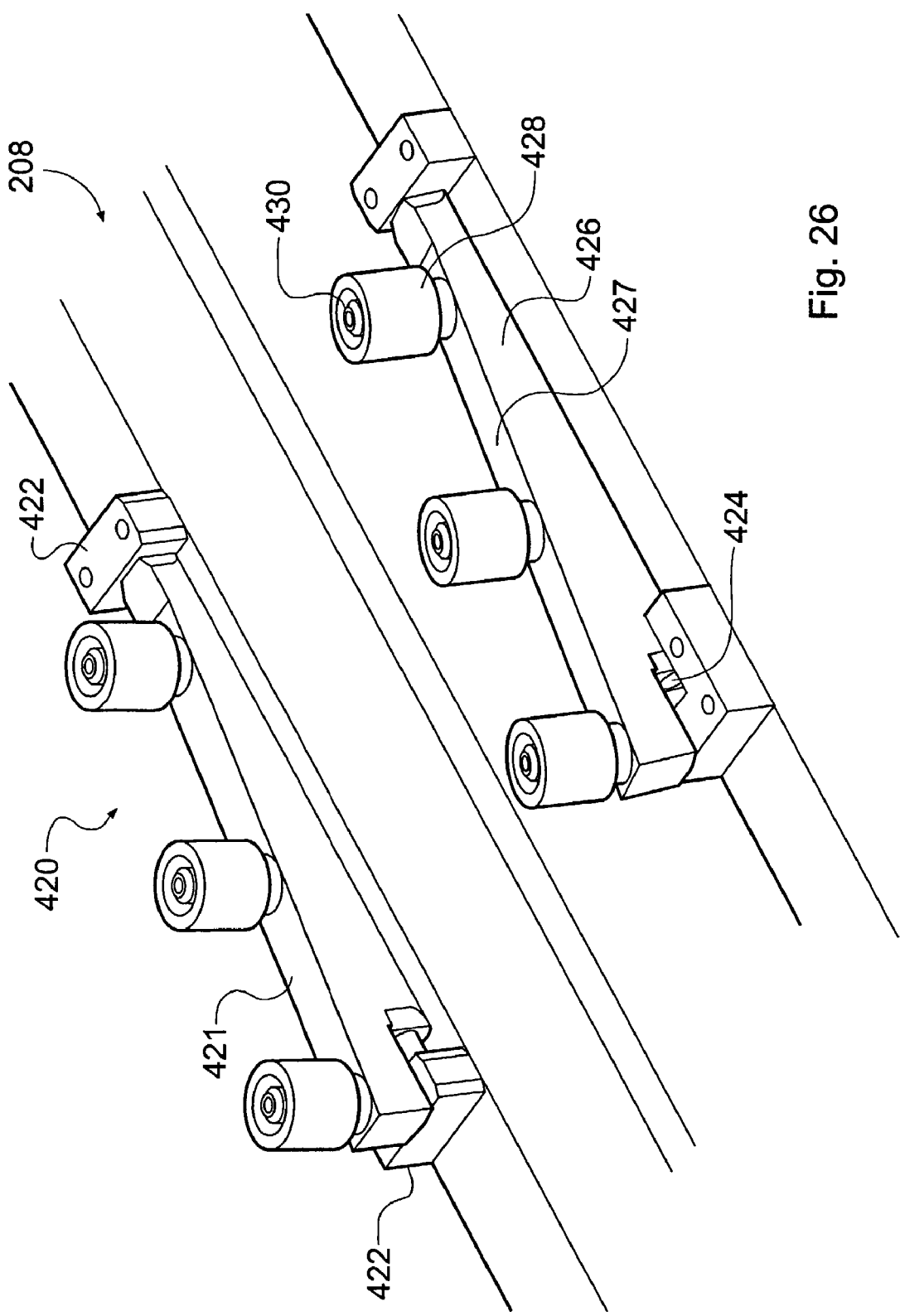
FIG. 26 shows a perspective view of a still further embodiment of a lid handling assembly.

FIG. 26 shows a perspective view of a further alternative embodiment of a lid handling assembly 420 which relies solely on rollers and has no ramps. Mounted on each side of a delivery lane 208 of the type described above are roller assemblies 421. Each roller assembly 421 comprises a pair of mounts 422 fastened adjacent to the delivery lane 208, with a roller arm axle 424 extending between the mounts 422 in a longitudinal direction with respect to the delivery lane 208. The roller arm axle 424 has mounted upon it a roller arm 426. The roller arm 426 is substantially elongate in shape and has an inclined upper surface 427. The roller arm 426 is rotatable about the roller arm axle 424, but is provided with a biasing mechanism (not shown), which biases the roller arm 426 such that the upper surface 427 is rotated slightly towards the delivery lane 208 and the opposite roller assembly 421. The biassing mechanism may comprise a suitable spring or springs, such as a compression spring acting between the arm 426 and the block 422.

The upper surface 427 of each roller arm 426 has a three roller axles 430 extending substantially perpendicularly therefrom and disposed along the length of the roller arm 426. A freely-rotatable roller 428 is mounted on each roller axle 430. The incline of the upper surface 427 means that the rollers 428 rotate about parallel axes which are inclined at a few degrees to the vertical. The rollers 428 are arranged on each roller arm 426 so that pairs of rollers are located on opposite sides of the delivery lane 208. As before, the rollers 428 may suitably each comprise a plurality of ball races stacked one upon the other, and surrounded by a tubular sleeve of a rubber material having a high coefficient of friction, such as santoprene. The biasing of the roller arms 426 is arranged such that the spacing between each pair of rollers 428 is slightly less than the width of a lid of a container to be handled by the lid handling assembly 420. Also, the lowest roller pair is arranged to be at substantially the same height above the delivery 208 lane as a lid on a container being conveyed along the delivery lane 208.

Operation of the lid handling assembly 420 is as follows. A container having a lid, which may or may not be of the overhanging type, is conveyed along the delivery lane by any convenient method, such as the conveying devices already described, and approaches the lid handling assembly 420 from the lower end of the roller arms 428. As the container and lid reaches the lid handling assembly 420, the lid abuts the lowest pair of rollers. The pressure of the lid against the rollers 428 forces the roller arms 426 to rotate away from each other until the lid and container can pass between the rollers 428, although the biasing of the roller arms 426 causes the rollers 428 to grip the lid. The rollers 428 rotate against the moving lid, and the inclined axis of rotation of the rollers 428 causes the rollers 428 to begin lifting the lid as the container moves forwards.

Similar gripping and lifting of the lid then occurs at the second and third pairs of rollers, until the lid has been completely removed from the container. The container is further conveyed along the delivery lane, and the lid remains gripped between the rollers because of the biasing of the roller arms 426, and hence suspended above the delivery lane 208.

When the container returns in the opposite direction, it engages with the rear wall of the suspended lid, and drags the lid down and out from between the rollers 428 until the lid falls onto the container. The roller arms 426 are then free to rotate back to their biased positions, ready for the next container.

A larger or smaller number of rollers than the three pairs shown in FIG. 26 may alternatively be provided, depending on the size of the rollers and of the lid to be handled. It is expected that most conveniently two, three, four or five roller pairs would be provided. However, a single roller pair may be used for handling a relatively small lid, if the biassing of the roller arms and the friction of the rollers provides an adequate grip on the lid.

A number of the subsidiary features of the various lid handling assemblies described herein can be included as desired in other embodiments. For example, the lid detection system shown in FIG. 25 can usefully be combined with any of the embodiments, as can appropriately modified versions of the spring loaded arms and guide arms shown in FIG. 13. Also, any of the various ramp and/or roller arrangements can be provided with a sufficient length to remove two or more lids at one time, as illustrated in FIGS. 10 and 13.

Alternative Well Plate Release Mechanism

FIGS. 27(*a*) to 27(*f*) show schematic diagrams of a release mechanism which provides an alternative embodiment to the escapement mechanism shown in FIG. 21, for releasing a well plate from a cassette placed in a feed port, and locating the well plate in the correct position for it to be conveyed. In this embodiment, the escapement mechanism is replaced by a gripper mechanism and a piston mechanism which operate in conjunction.

FIG. 27(*a*) shows a plurality of well plates 270 which are stacked directly one upon the other. The well plates 270 are held within a cassette of the type shown in FIG. 15 and the cassette itself is mounted in a feed port 209 of a well plate stacker apparatus such as that described in the second embodiment. The cassette and the feed port are not shown for the sake of clarity. The lower three well plates 270 are gripped from two sides by a pair of grippers 430. The grippers 430 support the stack of well plates retained within the cassette so that the well plate stack is suspended above a delivery bed 206 of the well plate stacker apparatus. The delivery bed 206 has four holes 431 (only two of which are shown in FIG. 27) passing through it, the through holes being arranged directly below the stack of well plates 270 so that each hole aligns with a corner of the well plate above. Arranged below the delivery beds 206 is a piston mechanism (not shown in these schematic Figures). The piston mechanism comprises a support device having four vertical support rods 432 which pass through the four holes 431 in the delivery bed 206. The lower ends of the support rods 432 are mounted on a horizontal rod support plate 434 below the delivery bed 206. An abutment plate 436, the purpose of which will be explained in due course, is rotatably mounted on the underside of the rod support plate 434. The support rods 432, the rod support plate 434 and the abutment plate 436 are all mounted on a piston assembly, which is not shown. The purpose of the piston assembly is to raise and lower the support rods 432, and the rod support plate 434.

In FIG. 27(*a*), the piston mechanism 433 is shown in a fully retracted, bottom position, in which the upper ends of the support rods 432 do not protrude above the surface of the delivery bed 206. To deliver a well plate from the cassette the piston mechanism 433 is operated such that the support rods 432 are pushed upwards through the delivery bed 206 until they reach a support, top position in which they abut the lowest well plate 270*a* held by the grippers 430. This is shown in FIG. 27(*b*). Then, the grippers 430 are moved horizontally outwards so that they cease to grip the stack of well plates 270, which remain supported on the support rods 432, as is shown in FIG. 27(*c*).

The support rods are then lowered to an intermediate position by a distance 'd' equivalent to the height of a single well plate, carrying the stack with them, as shown in FIG. 27(*d*). The lowest well plate 270*a* in the well plate stack is thus now located just below the level of the grippers 430.

Figure 27A:
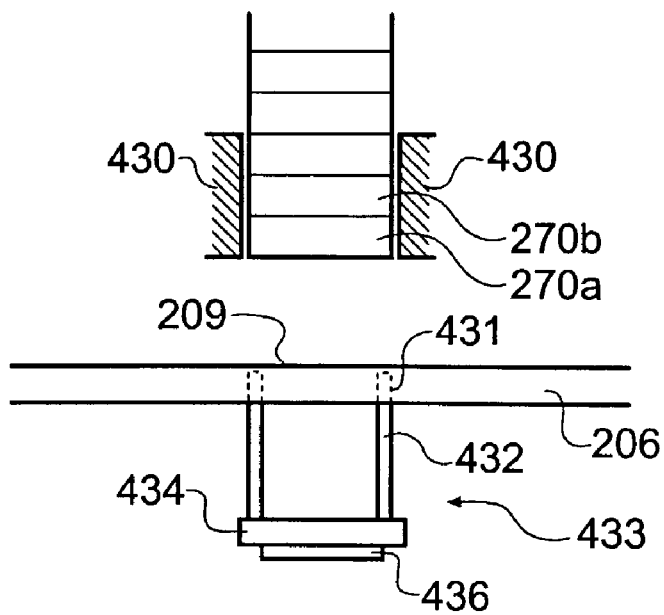
FIGS. 27(a) to 27(f) show schematic representations of a further embodiment of a well plate release mechanism in various positions.
Figure 27B:
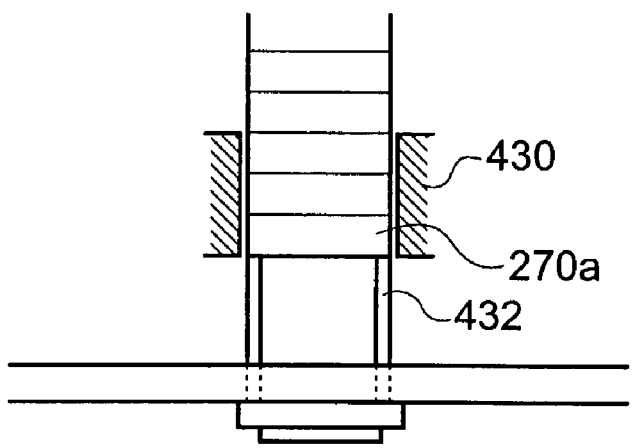
Figure 27C:
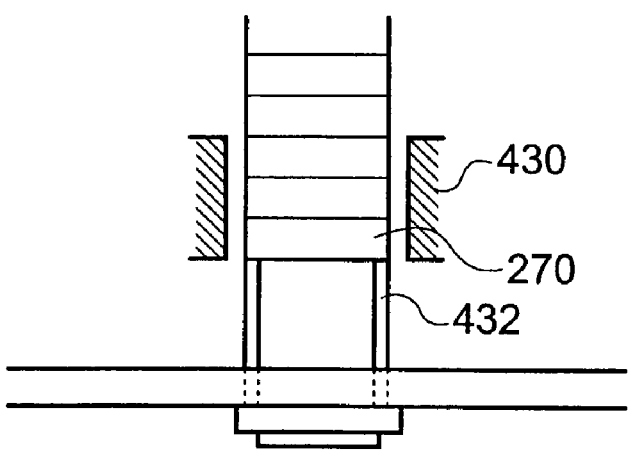
Figure 27D:
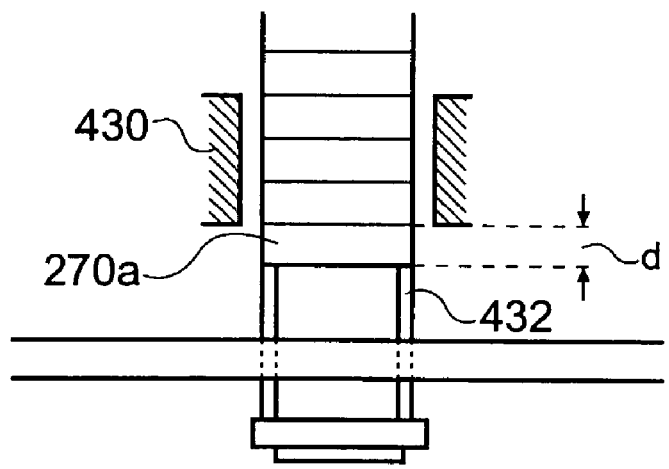
Figure 27E:
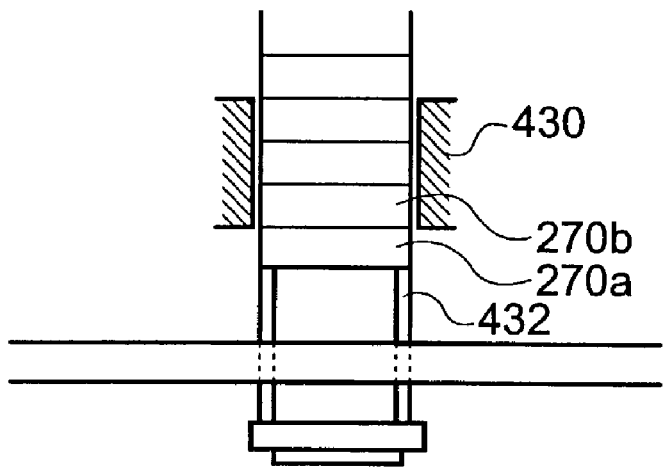
Figure 27F:
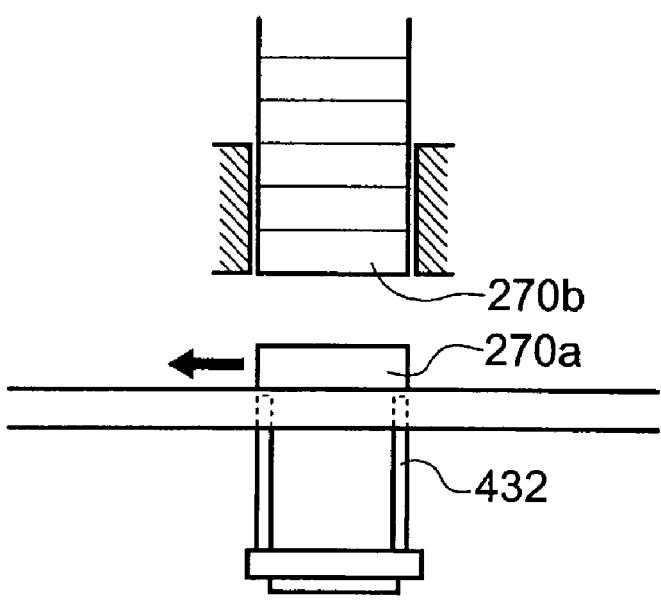

FIG. 27(e) shows the next position in the release sequence, in which the grippers are moved horizontally inwards so as to grip the well plate stack again. However, because the stack has already been lowered, the grippers 430 do not come into contact with the lowest well plate 270a. The piston mechanism 433 then lowers the support rods 432 back down the retracted position. The lowest well plate 270a is lowered also and comes to rest on the delivery bed 206. The lowest well plate 270a is thus now located in the correct position for conveying, and can be moved along the delivery bed 206 in an horizontal direction by a suitable conveying device, such as a dog or a carriage. After the lowest well place 270a has been moved, the gripper mechanism and piston mechanism are back in their original positions as shown in FIG. 27(a), with the exception that a different well plate 270b is now in the lowest position, arranged ready for subsequent release.

As is evident from FIG. 27, the piston mechanism may be deployed into any one of three vertical positions. These are the retracted, bottom position, in which the support rods are approximately at the level of the delivery bed 206, the support, top position in which the support rods abut the lower surface of a stack of well plates, and also extend substantially to the height of the grippers 430, and the intermediate position, in which the support rods 432 abut the stack of well plates, but support them at a height such that the lowest well plate is below the level of the grippers 430. Prior to loading a full cassette of well plates into feed port, it is necessary to position the support rods 432 into their support position. In this way, they will engage with and support the stack of well plates as the cassette is inserted. The grippers 430 can then move inwards to grip the stack of well plates, so that the release, locating and conveying of the plates may begin. A microswitch or similar may be provided in the feed port so that the support rods 432 are automatically deployed into the support position when a cassette is removed from the feed port, so that they are ready to receive a further stack of well plates when the next cassette is inserted.

This embodiment means that the release mechanism can be readily adapted to handle well plates or other containers of differing thicknesses. Well plates conventionally come in two thicknesses, thin and thick. A thin well plate has a thickness of approximately 20 cm and a thick well plate has a thickness of approximately 30 cm. All that is required is that the intermediate position of the support rods 432 be such that the distance 'd' shown in FIG. 27(d) corresponds to the thickness of the lowest well plate or other container 270a.

The present embodiment is further advantageous in that the grippers 430 are configured to grip the stack of well plates by coming into contact with a plurality of well plates at the bottom of the stack, including the lowest well plate. This distributes the pressures exerted on the well plate stack, and helps to prevent bowing of the well plates, which can occur if more localized gripping is used, in particular with the hinged arrangement of the second embodiment (see FIGS. 21(a) to 21(c)).

Gripper Mechanism

As is evident from FIG. 27, the grippers 430 take the form of a pair of opposing plates with substantially parallel vertical surfaces. The vertical surfaces may be provided with a high friction resilient coating, such as rubber, to provide better grip on the well plates. The grippers operate by being moved towards and away from the well plate stack in a horizontal direction. Therefore, they may be driven by any mechanism suitable to provide this motion. For example, pistons or motor-driven worm drives may be employed. However, in many instances it is desirable to keep the size of the gripper mechanism to a minimum, so that adjacent delivery lanes of a stacker apparatus may be more closely spaced. One way of achieving this is to provide a gripper mechanism which utilizes levers to provide the horizontal motion.

FIG. 28 is a perspective view of a feed port 209 of a well plate stacker apparatus incorporating the gripper mechanism. Certain parts of the apparatus are not drawn in order to allow the important parts of the gripper mechanism to be seen. The substantially horizontal delivery bed 206 may be seen. A well plate cassette 216 is arranged in the feed port 209, no well plates are shown. A gripper 430 is shown, having a substantially flat vertical face which faces towards the position where a stack of well plates would be contained within the cassette inserted in the feed port 290. The opposite gripper 430 is obscured by its mounting components. Each gripper 430 is attached by four screws 440 to a mounting plate 442. Each mounting plate 442 is disposed within an aperture 444 in a vertically mounted support plate 446. The mounting plate 442 is attached to the support plate 446 by upper and lower pivoting arms 448, 450 which are arranged such that the gripper 430 on the mounting plate 442 can be moved backwards and forwards in a horizontal direction while the face of the gripper 430 is kept substantially vertical. Movement of the mounting plate 442 and gripper 403 is provided by a system of levers 452. The lever system 452 comprises an upper lever 452a, which is pivotally connected at one end to the mounting plate 442, a lower lever 452b which is arranged below the delivery bed 206 and connected at one end to a drive mechanism, and intermediate levers connecting the upper lever 452a to the lower lever 452b and passing through a suitably sized opening 454 in the delivery bed 206. The drive mechanism (not shown), which is a single hydraulic piston located symmetrically below the delivery bed 206, operates to move both the lower levers 452b upwards, and this motion is transferred via the lever system 452 and the pivot arms 448, 450 to give horizontal movement of the grippers 430 towards each other. The arrangement depicted in FIG. 28 shows the two lower levers 452b associated with the two grippers 430 connected to a single drive mechanism. The arrangement is simple and convenient, but alternatively separate drive mechanisms may be used to drive the individual grippers. This may be suitable if it is desired to provide independent motion of the grippers. Any drive mechanism capable of providing appropriate motion between two positions may be used.

Also evident in FIG. 28 are support posts 451 which bolt the hydraulic piston assembly 464 to the underside of the delivery bed 206.

Figure 29A:
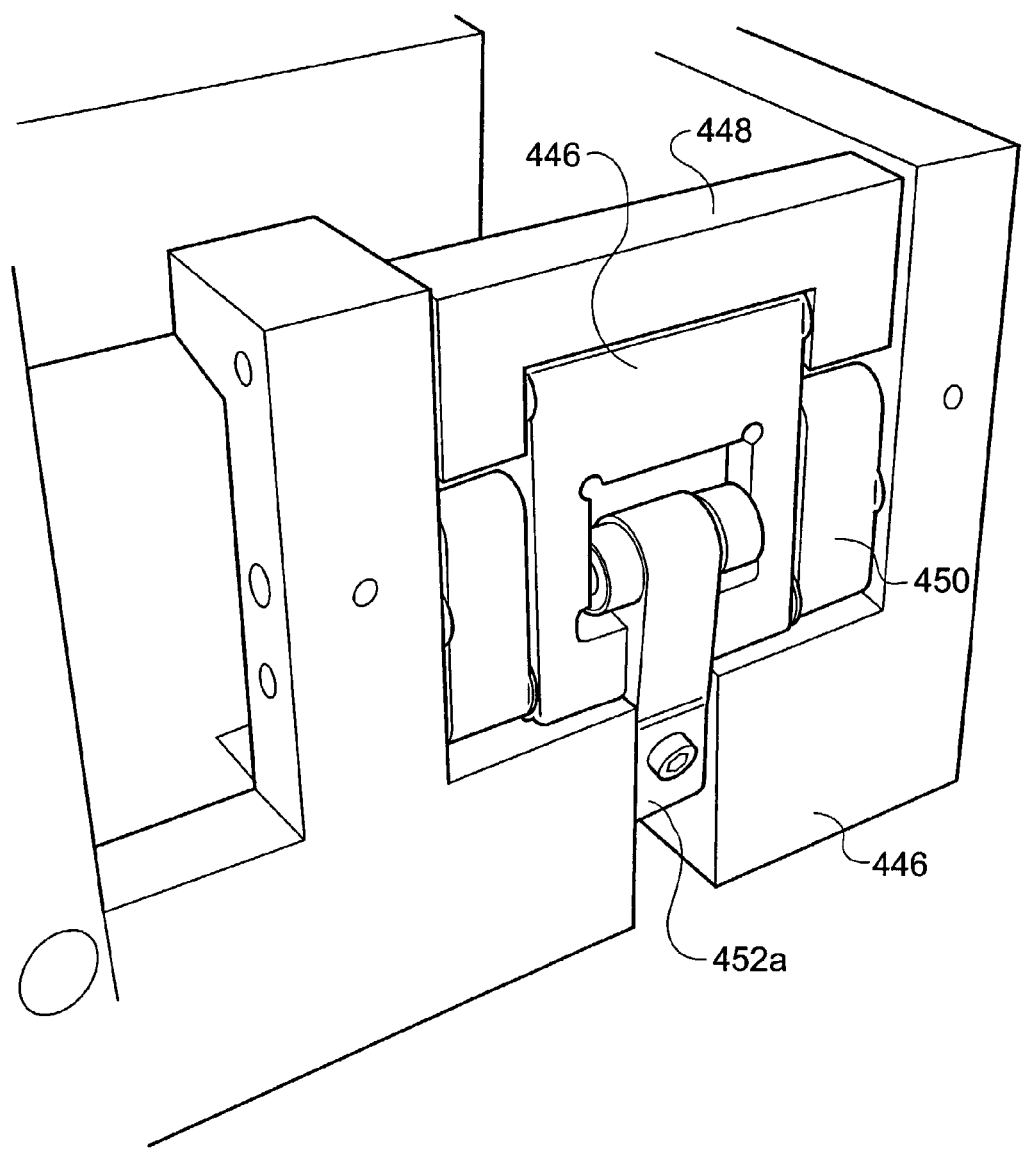
FIGS. 29(a) and 29(b) show perspective views of a gripper mechanism of the well plate mechanism of FIG. 27.
Figure 29B:
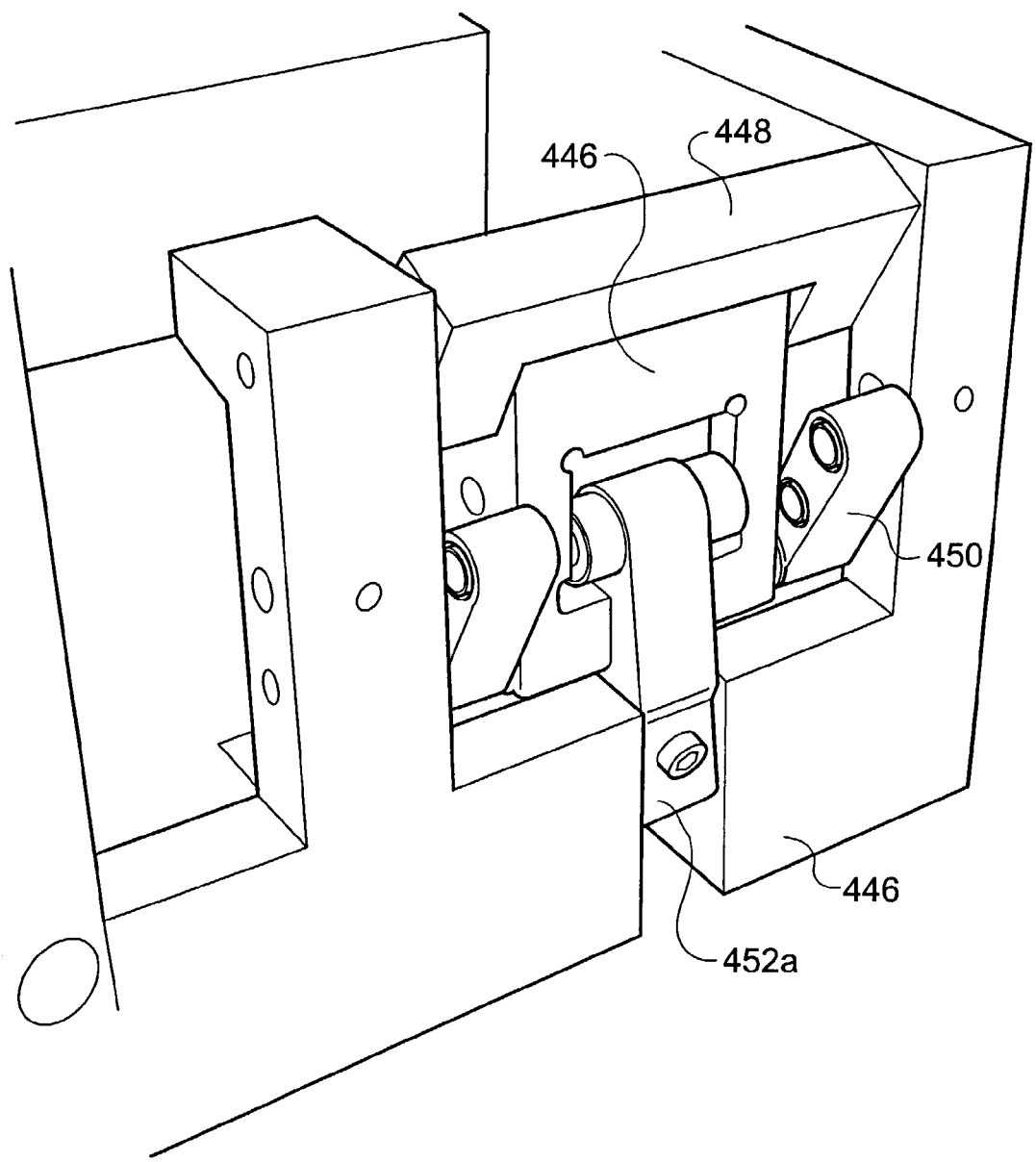

FIG. 29a is a perspective rear view of a single gripper mechanism, shown in a retracted position, in which the associated gripper is positioned away from a well plate stack (as in FIG. 27(c), for example). FIG. 29b is a perspective view of the same gripper mechanism, but this time arranged such that the associated gripper 430 is in an advanced position, so as to grip any well plate present in the feed port 290 (as in FIG. 27(a), for example).

Other arrangements of lever and pivots may be used to provide the necessary motion of the grippers.

Piston Mechanism

As mentioned previously, the support rods 432, the rod support plate 434 and the abutment plate 436 of the piston mechanism are moved vertically by a piston assembly.

Figure 30C:
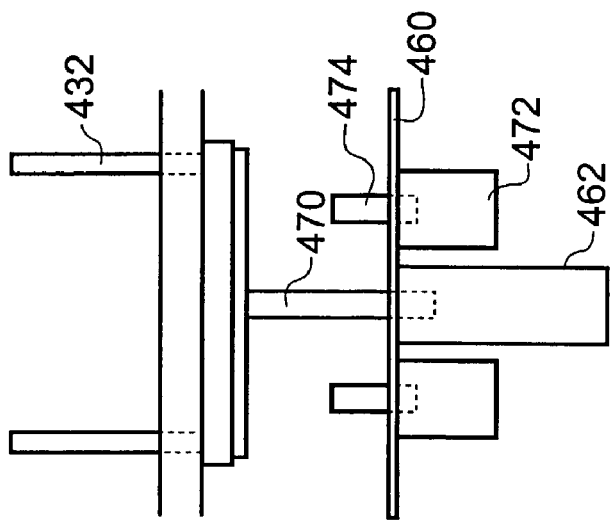
FIGS. 30(a) to 30(c) shows schematic representations of a piston mechanism of the well plate release mechanism of FIG. 27.
Figure 30B:
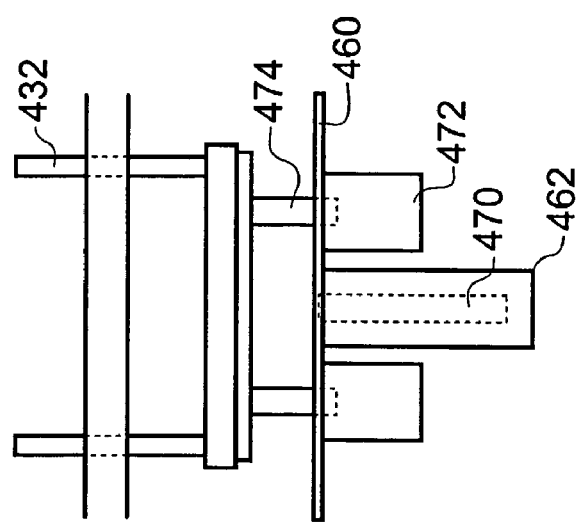
Figure 30A:
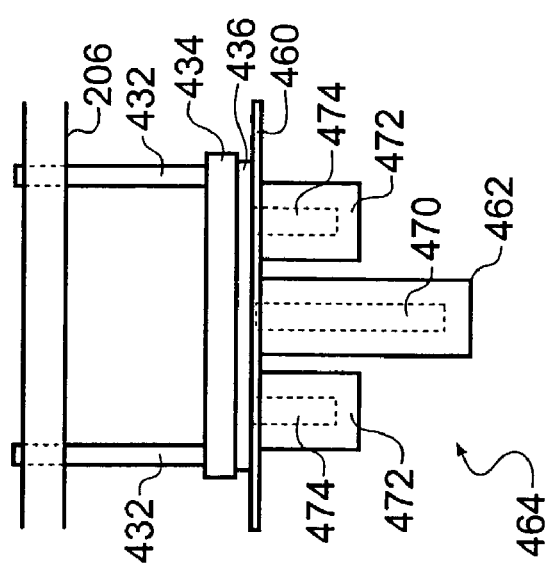

FIG. 30 shows a series of schematic diagrams of the piston assembly 464. The piston assembly 464 comprises a horizontal piston support plate 460, which is bolted to the underside of the delivery bed 206 by the four support posts 451 that can be seen in FIG. 28 but which are not shown in FIGS. 30(a) to 30(c). The piston support plate 460 supports on its underside three pistons. A main piston 462 is located approximately centrally on the piston support plate, and is flanked by two subsidiary pistons 472 arranged one on each side of the main piston 462. The subsidiary pistons 472 have a shorter stroke than the main piston 462. The main piston 462 has a main piston rod 470 which is vertically moveable through an aperture in the piston support plate 460. Similarly, the subsidiary pistons 472 each have a subsidiary piston rod 474 which is also vertically moveable through an aperture in the piston support plate 460. The pistons are each hydraulic two position pistons.

FIG. 30(a) shows the support rods 432 in their retracted position, in which they do not protrude much above the delivery bed 206. In this position, the abutment plate 436 rests on the piston support plate 460 and three piston rods are fully retracted within their respective pistons.

FIG. 30(b) shows the support rods 432 in the intermediate position. This is provided by extension of the subsidiary piston rods 474, which abut the abutment plate 436, and hence support the support rods 432 in the intermediate position. The length of the subsidiary piston rods 474 is such that the support rods 432 protrude only partly through the delivery bed 206. As illustrated in FIG. 30(b), in the intermediate position, the main piston rod 470 is fully retracted within the main piston 462.

FIG. 30(c) shows the support rods 432 in the support position, in which they protrude by the maximum possible amount through the support bed 206, so as to support a stack of well plates so that the lowest well plate is between the grippers 430 of the release mechanism. The support position is achieved by moving the main piston rod 470 into its extended position, in which it abuts the abutment plate 436 and pushes the rod support plate 432 up against the underside of the delivery bed 206. The arrangement in FIG. 30(c) shows the subsidiary piston rods 474 extended from the subsidiary pistons 472. However, they may also be retracted when the support rods are in the support position, since they have no effect in this position.

Thus, the support rods may be moved directly between the retracted position (FIG. 30(a)) and the support position (FIG. 30(c)) by extension and retraction of the main piston rod 470. The subsidiary pistons 472 are used to provide the intermediate position. The operation of the support rods as described with reference to FIG. 27 requires that the intermediate position occur after the support position. To achieve this, the main piston rod 470 is extended to place the support rods 432 in the support position, and then the subsidiary piston rods 474 are fully extended to the position shown in FIG. 30(c). Then, the main piston rod 470 is retracted to lower the support rods 432. During the lowering, the abutment plate 436 comes into contact with the extended subsidiary piston rods 474 so that the lowering of the support rods 432 is stopped, and the support rods 432 are held in the intermediate position. The main piston rod 472 continues retracting until the situation illustrated in FIG. 30(b) is reached. If it is desired to position the support rods in the intermediate position from the retracted position, it is merely necessary extend the main piston rods 474 which will push the support rods 432 upwards.

Pneumatic or hydraulic pistons may be used for the subsidiary pistons 472 and the main piston 462, as preferred. The pistons may be controlled by a computer or other control device, which may also be used to operate other parts of the well plate stacker apparatus.

The purpose of the abutment plate 436 is to provide height adjustment of the intermediate position, so that the piston mechanism and gripper mechanism can accommodate well plates and containers of varying thickness. Referring to FIG. 27(d), it can be seen that the distance 'd' by which the well plate stack is lowered to release the bottom well plate is determined by the well plate thickness. To provide the capability of handling both thick and thin well plates, the apparatus must allow for lowering by $d_{thick}$ and $d_{thin}$ as desired, where $d_{thin} < d_{thick}$.

Figure 31A:
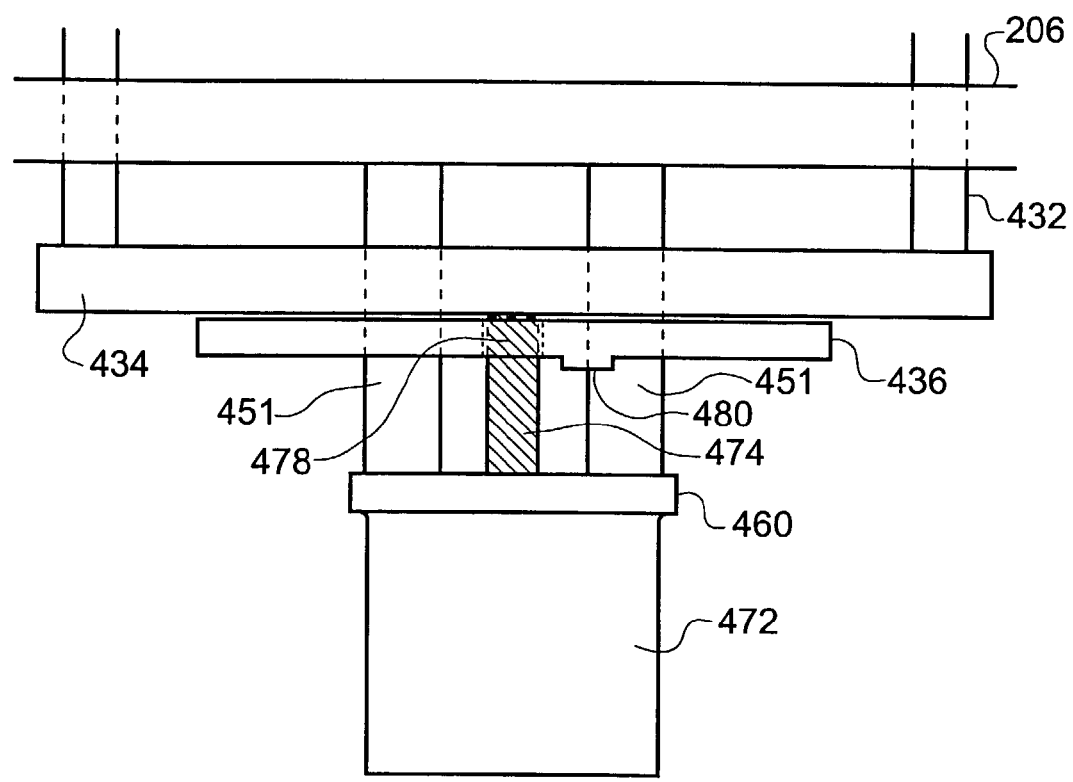
FIGS. 31(a) and 31(b) show further schematic views of the piston mechanism of FIG. 30.

FIG. 31(a) shows a schematic side view of the piston mechanism in a direction perpendicular to the views shown in FIG. 30. Consequently, only one subsidiary piston 474 is visible (the main piston 462 is not shown for the sake of clarity). As before, the delivery bed 206 can be seen, with the support rods 432 extending through it, mounted on the rod support plate 434. The abutment plate 436 is shown on the underside of the rod support plate 434 with the subsidiary piston 470 and its associated subsidiary piston rod 474 positioned below by the piston support rods 476 which extend vertically through the abutment plate 436 and the rod support plate 434.

The abutment plate is rotatable about a substantially central vertical axis. The lower side of the abutment plate 436 is provided with a pair of holes 478 arranged on opposite sides of its width and also a pair of protrusions 480 similarly arranged on opposite sides of the width. Conveniently, a hole 478 and a protrusion 480 are positioned angularly adjacent to one another with their centers equidistant from the rotation axis of the rotatable abutment plate 436. The pair of holes and similarly the pair of protrusions are each located such that when the abutment plate is suitably positioned, one or other pair coincides with the subsidiary piston rods 474 when these are in their extended position. Rotation of the abutment plate is conveniently performed by a suitably-located movable needle which abuts the abutment plate and whose position is controllable by a pneumatic feed line. However, other movement methods may be alternatively used. Actuation of the needle 482 is controlled by the apparatus control system to allow switching between different well plate thicknesses.

In the arrangement depicted in FIG. 31(a), the abutment plate is rotated so that the subsidiary piston rods 474 coincide with the holes 478 in the abutment plate 436. Therefore, when the support rods are lowered into their intermediate position, the subsidiary piston rods 474 enter the holes 478 in the abutment plate 436 so that the support rods are lowered more than they would be in the absence of the holes. This is used to release a "thick" well plate from the stack.

Figure 31B:
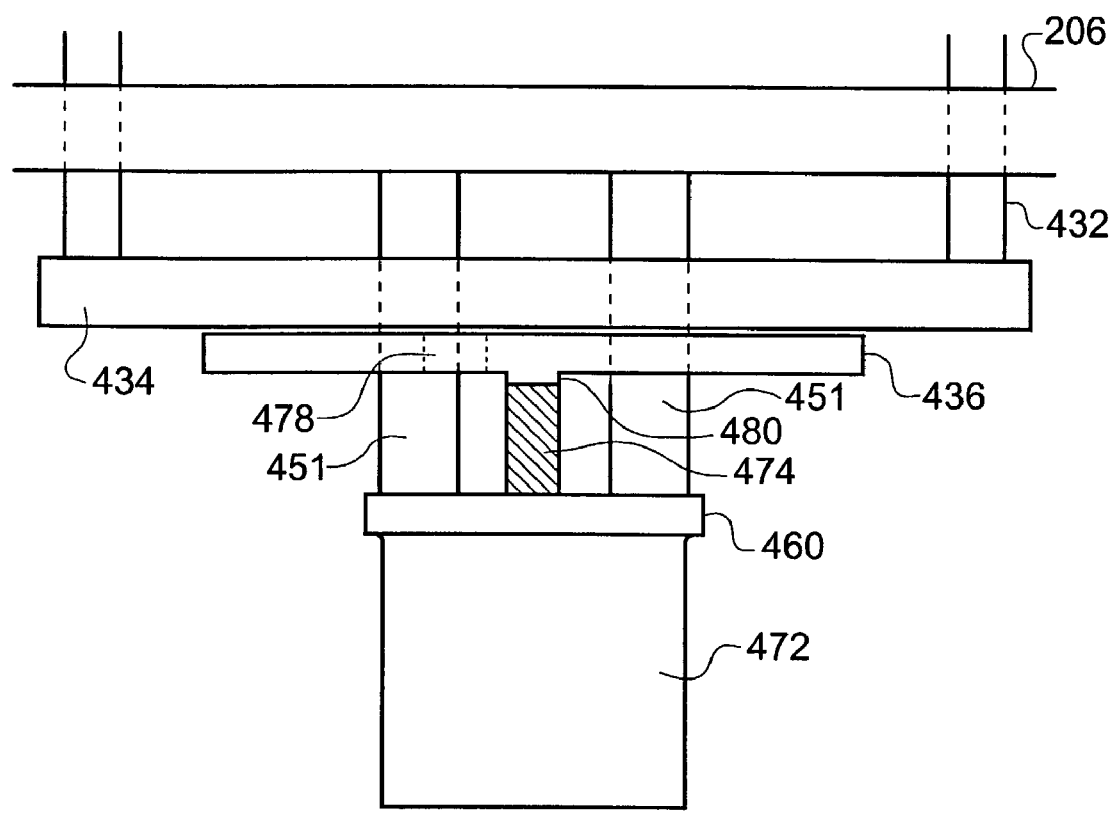

To accommodate a "thin" well plate, the abutment plate is rotated until the protrusions 480 align with the subsidiary piston rods 474. In this case, when the support rods are lowered, the protrusions align with and abut the subsidiary piston rods 474 and the downward motion of the support rods 432 is arrested at a higher level than when the depression 478 are aligned with the subsidiary piston rods 474. This is depicted in FIG. 31(b).

If desired, a number of holes and protrusions of varying sizes may be provided on the abutment plate, to give more than two distances 'd' shown in FIG. 27(d). However, in practice, well plates typically are available in only two thickness, so that the abutment plate shown in FIG. 31a is sufficient. It will also be understood that the same functionality can be provided with two differing protrusions, two holes of different depths, or by any other variable height abutment mechanism. One alternative that has been built and tested uses a rotatable cam to provide different height abutments.

Figure 32A:
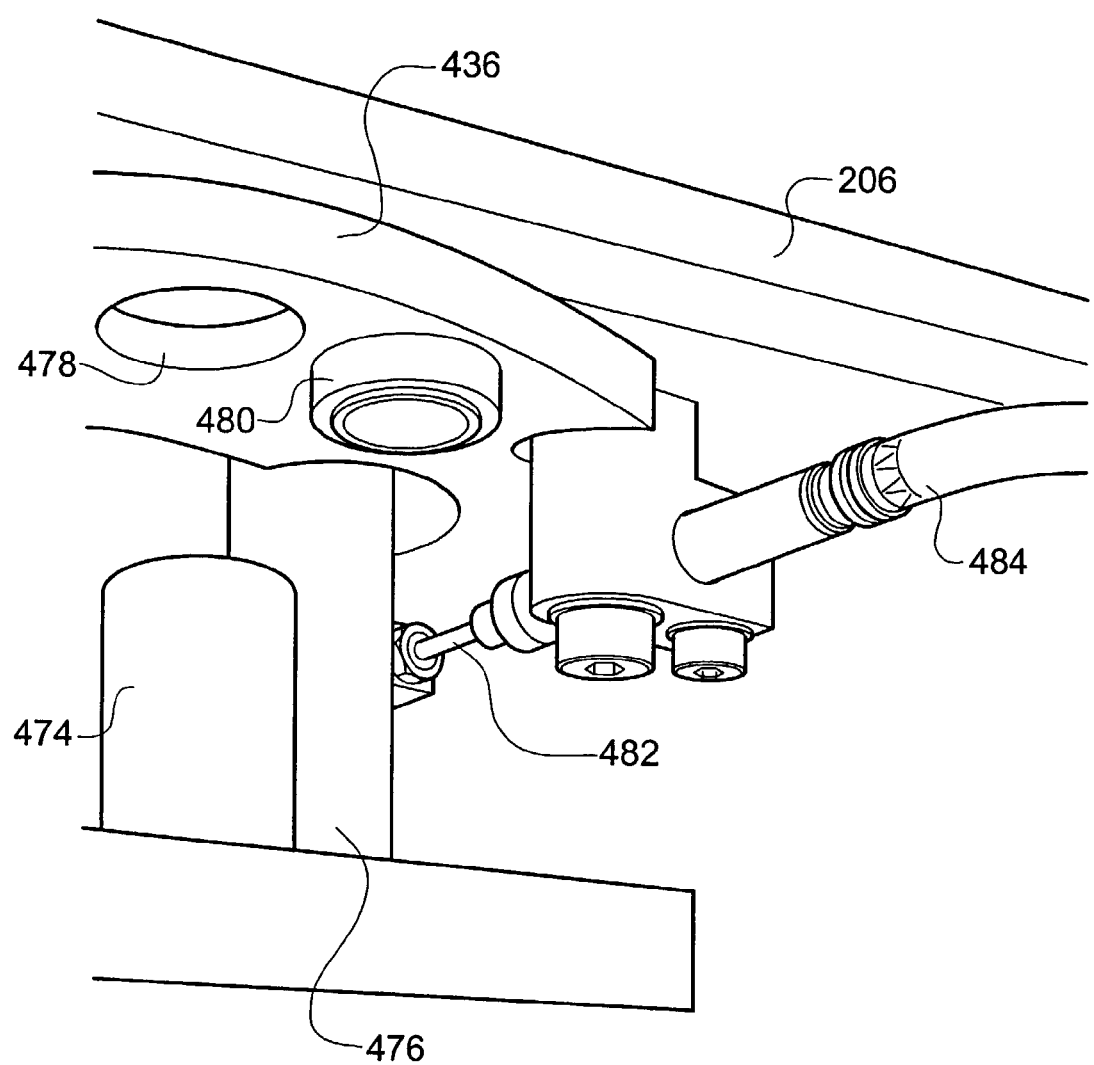
FIGS. 32(a) and 32(b) show perspective views of the piston mechanism of FIG. 30.

FIG. 32(a) is a perspective view of part of the abutment plate 436 in the position shown in FIG. 30(c) and with the abutment plate 436 rotated in the position shown in FIG. 31(a) for thick well plates. The abutment plate 436 may be suitably made from metal or a plastics material. A hole 478 and its adjacent protrusion 480 are visible, with the hole 478 aligned with the subsidiary piston rod 474, to provide handling of thick well plates. Note, however, that the subsidiary piston rod 474 is not fully extended to enter the depression 478, as would be the case if the support rods 432 were in the intermediate position. The needle 482 and pneumatic feed line 484 are also shown. The needle is in an extended position, to push the abutment plate 436 around.

Figure 32B:
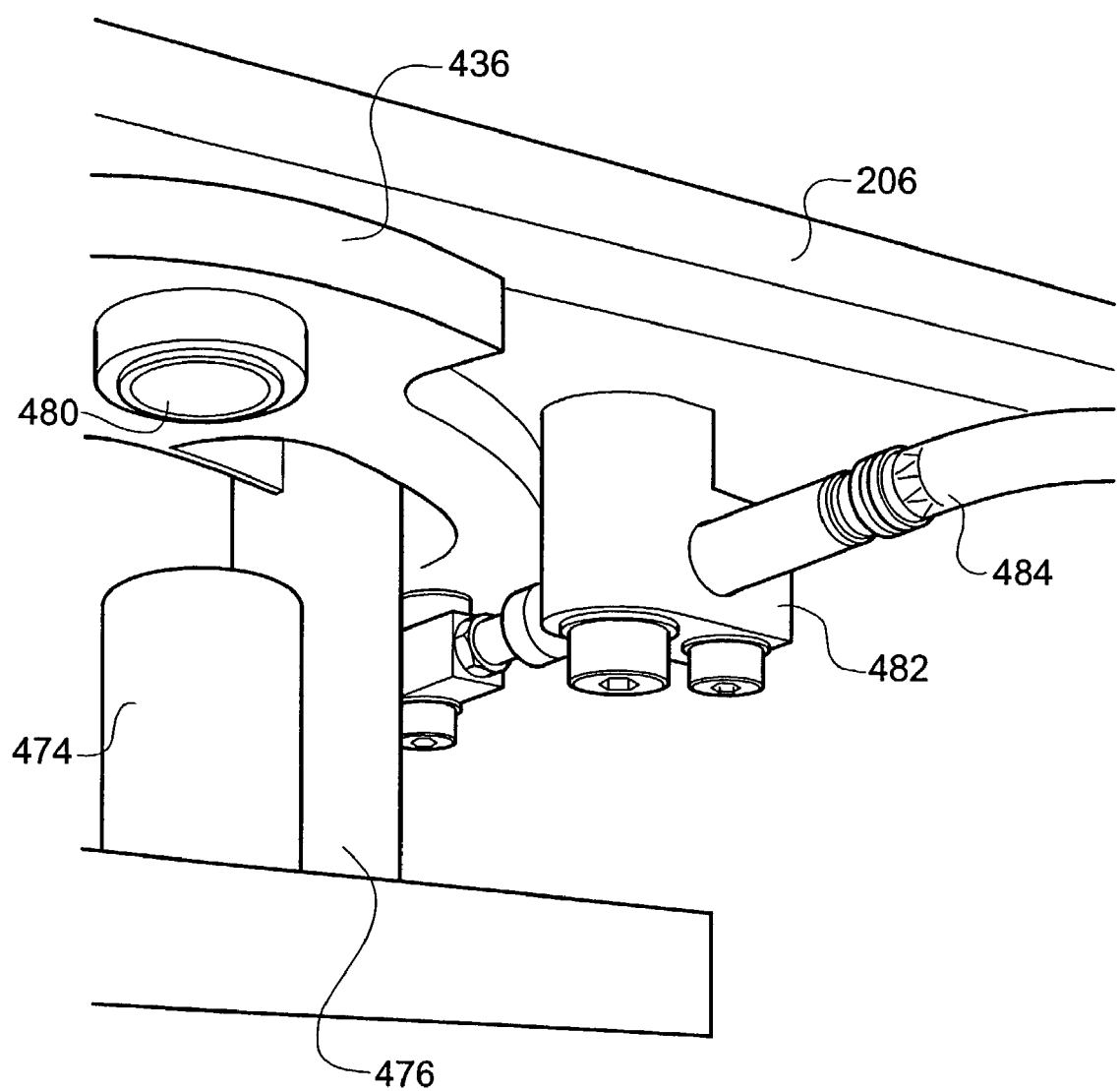

FIG. 32(b) is a similar perspective view of the abutment plate to that shown in FIG. 32(a). However, in this case the abutment plate 436 has been rotated, by retraction of the needle 482, so that the protrusion 480 is aligned with the subsidiary piston rod 474, to accommodate thin well plates. A piston support rod 476 may also be seen in FIGS. 32(a) and 32(b).

Figure 33:
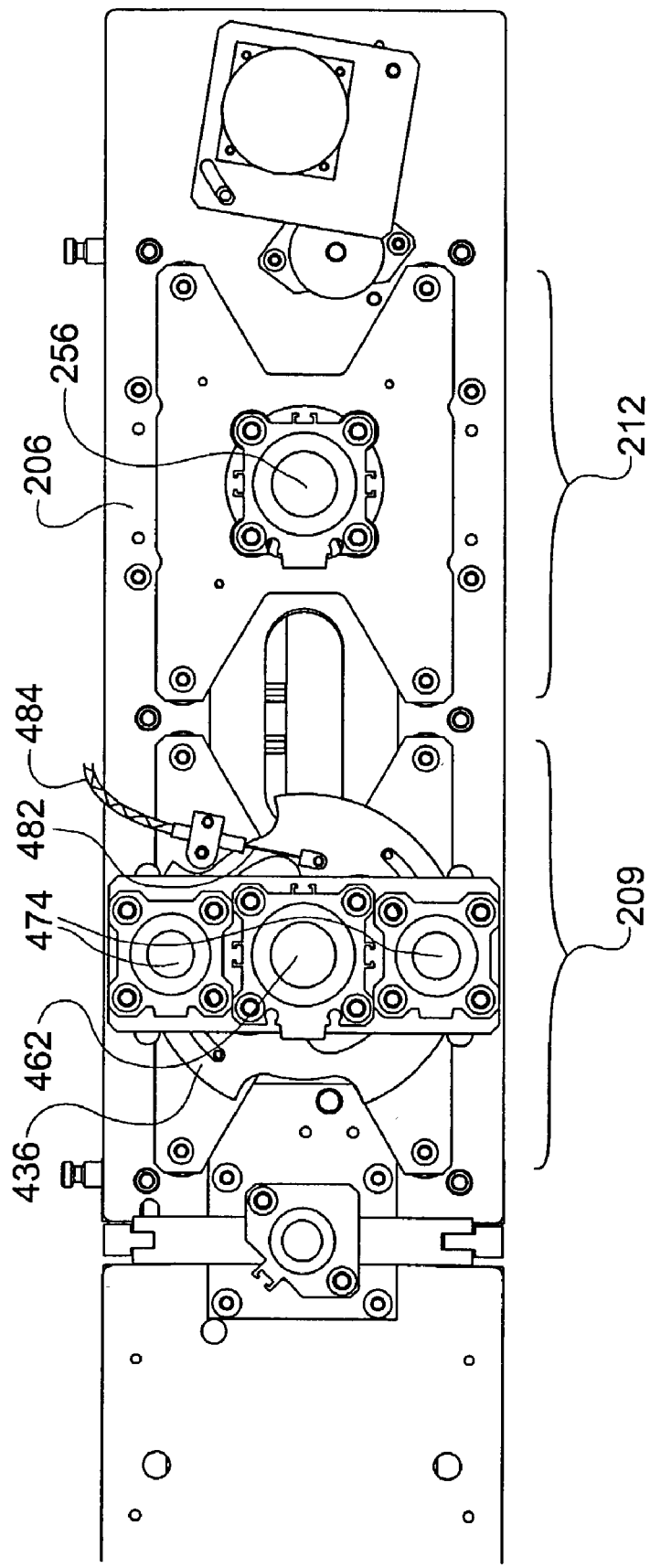
FIG. 33 shows a plan view of part of the underside of a well plate stacker apparatus comprising the lid handling assembly of FIG. 25 and the well plate release mechanism of FIG. 27.

FIG. 33 is a view from below showing the underside of part of a well plate stacker apparatus incorporating the piston mechanism. The apparatus has a delivery bed 206 configured to provide a single well plate delivery lane. A feed port 209 is provided, together with a stacking port 212 which returns well plates after conveying samples to a cassette by means of a single vertically movable piston 256, as described with reference to FIG. 19. Beneath the feed port 209 are located the main piston 462 and the two subsidiary pistons 472, arranged one of each side of the main piston 462. Between the pistons and the delivery bed 206 is the rotatable adjustment plates 436. The needle 482 and its pneumatic feed line 484 may also be seen; the needle is in the extended position shown in FIG. 32(a).

Figure 34:
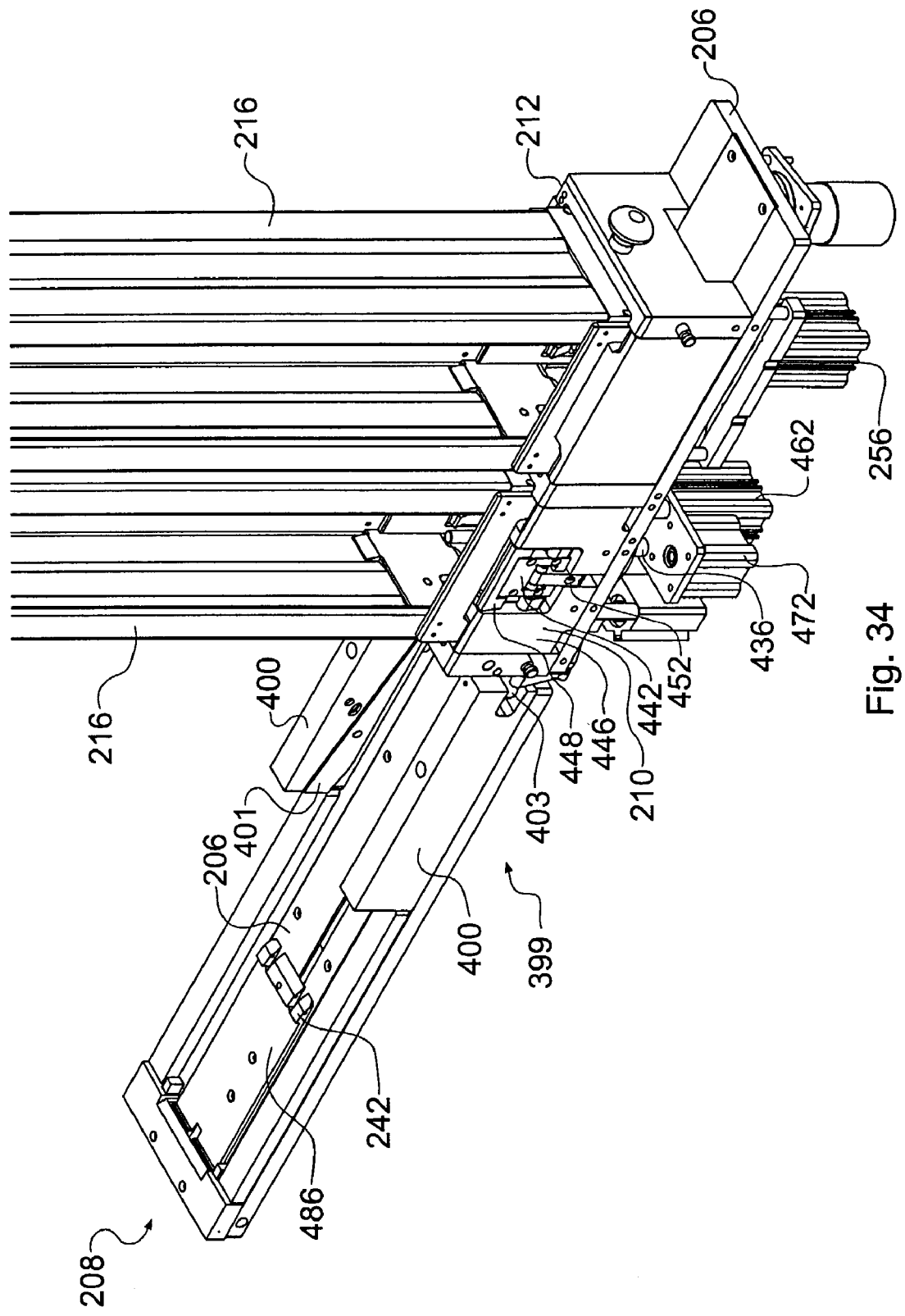
FIG. 34 shows a perspective view of the well plate stacker apparatus of FIG. 33.

FIG. 34 is a perspective view of the apparatus shown in FIG. 33, which also illustrates the gripper mechanism, and the lid handling apparatus featuring ramps with fixed rollers.

The apparatus has a delivery bed 206 having a single delivery lane 208, with a corresponding single feed port 209 and a single stacking port 212. Each of the ports is shown with a cassette 216 inserted therein, although neither cassette contains any well plates.

The lid handling assembly 399 includes the pair of ramps 401 and rollers 403 mounted on a pair of mounting blocks 400 positioned one on each side of the delivery lane 208.

One side of the gripper mechanism can be seen, comprising the support plate 446, the mounting plate 442, the upper and lower pivot arms 448, 450, and the upper lever 452. One of the subsidiary pistons 472 and the main piston 462 are visible mounted below the delivery bed 206, as is part of the abutment plate 436.

The apparatus further comprises a carriage 486 operable to convey a well plate along the delivery lane 208. The carriage may be driven by any suitable mechanism, such as a belt drive, or a worm drive, the former being preferred since it can slip when the carriage is arrested. When a well plate is released from the cassette 216, the carriage 486 is situated below the cassette 216, in the feed port 209, so that the well plate is lowered onto the carriage 486 by the support rods. This is the reason why the support rods protrude slightly above the delivery bed in the retracted position; it is only necessary to lower them enough for the well plate to come to rest on the carriage. The carriage provides an alternative to the pushing dog and pick-up catch of the second embodiment.

A particular advantage of the well-plate cassette described herein, together with the delivery system in the form of either the escapement mechanism or the gripper/piston mechanism is that the plates can be stacked in the cassettes directly one upon the other for handling. Not only does this reduce space and hence allow more compact apparatus to be provided, but it also makes the loading and unloading of cassettes before and after handling rapid and simple. It is much quicker for an operator to load or unload a stack of plates into or out of a cassette than it is to arrange individual plates on separate shelves of an elevator device or similar and remove them afterwards, i.e. the stack system described herein is much easier to load and unload than the conventional "hotel" systems. Hence, these aspects of the present invention permit arraying to be performed more quickly than is possible with prior art devices.

What is claimed is:

1. Apparatus for handling biological sample containers each having a lid, the apparatus comprising:
   (a) a conveyor assembly operable to convey containers between a first position and a second position; and
   (b) a lid handling assembly operable to remove lids from containers being conveyed through the lid handling assembly from the first position to the second position, and to replace the lids onto containers being conveyed through the lid handling assembly from the second position to the first position, wherein:
      (i) lid removal and replacement being effected by mechanical interaction between the lids and the lid handling assembly as the containers are conveyed through the lid handling assembly, and
      (ii) the lid handling assembly comprises a pair of rotatable rollers arranged such that the conveyor assembly conveys a container between the pair of rollers from the first position to the second position and from the second position to the first position, each roller having an axis of rotation inclined with respect to a perpendicular to a plane in which the containers are conveyed, the rollers operable to grip the lid of a container being conveyed between the rollers from the first position to the second position and feed the lid in a forwardly and upwardly direction.

2. Apparatus according to claim 1, in which the lid handling assembly further comprises a pair of ramps arranged such that the conveyor assembly conveys a container between the pair of ramps from the first position to the second position and from the second position to the first position, the ramps sloping upward from lower ramp ends facing towards the first position and arranged such that they pass under side walls of the lid of a container being conveyed between the pair of ramps from the first position to the second position, wherein the rotatable rollers are located in front of each lower ramp end, the rollers being operable to direct the lid over the lower ramp ends.

3. Apparatus according to claim 2, in which the rollers are biased towards one another to provide enhanced engagement of the rollers with the lid.

4. Apparatus according to claim 2, in which the pair of ramps is arranged such that a lid removed from its container sits on the ramps at a height at which a lowest part of the lid engages with a container being conveyed between the ramps from the second position to the first position so that the container pulls the lid down the ramp until the lid falls onto the container.

5. Apparatus according to claim 2, in which the ramps have a length sufficient to accommodate the lids of at least two containers and the conveying apparatus is operable to convey at least two containers from the first position to the second position between the pair of ramps before conveying either container from the second position to the first position.

6. Apparatus according to claim 2, in which the lid handling assembly further comprises one or more retainers operable to retain a lid or lids on the pair of ramps until the lid or lids is replaced on a container.

7. Apparatus according to claim 6, in which the one or more retainers comprises a movable abutment on at least one of the ramps of the pair of ramps which inhibits a lid or lids on the pair of ramps from sliding down the ramps.

8. Apparatus according to claim 6, in which the one or more retainers comprise a spring-loaded hinged arm arranged above the pair of ramps and biased to push downwardly on a lid held on the ramps.

9. Apparatus according to claim 2, in which each ramp has a portion having a steeper gradient than a subsequent portion, to provide rapid initial lifting of a lid.

10. Apparatus according to claim 2, in which each ramp has a portion having a shallower gradient than a subsequent portion, to encourage a lid to slide down the ramps under gravity.

11. Apparatus according to claim 1, in which each roller is pivotably mounted and biased towards the opposite roller, to enhance the grip of the pair of rollers upon the lid.

12. Apparatus according to claim 1, and further comprising one or more additional pairs of rollers arranged parallel to and rearwardly and upwardly from the first-mentioned pair of rollers such that a gripped lid can be fed from roller pair to roller pair as the container is conveyed between the rollers.

13. Apparatus according to claim 1, in which the lid-handling assembly is removably mounted on the conveyor assembly.

14. Apparatus according to claim 1, in which the lid handling assembly is configured to handle biological sample containers having the form of Q-trays.

15. Apparatus according to claim 1, in which the lid handling assembly is configured to handle biological sample containers having the form of omni-trays.

16. Apparatus according to claim 1, in which the lid handling assembly is configured to handle biological sample containers having the form of petri dishes.

17. Apparatus according to claim 1, in which the lid handling assembly is configured to handle biological sample containers having the form of well plates.

18. Apparatus according to claim 1, and further comprising one or more additional conveyor assemblies and lid handling assemblies, and operable to convey, remove lids from, and replace lids onto, a plurality of containers simultaneously.

19. Apparatus according to claim 1, and further comprising a storage assembly operable to store a plurality of containers, to supply any of the stored containers to the first position for the container to be conveyed to the second position, and to remove the container from the first position after it has been conveyed from the second position to the first position.

20. Apparatus according to claim 1, in which the conveyor is further operable to convey containers from the first position to a third position after the containers have been conveyed from the second position to the first position.

21. Apparatus according to claim 20, and further comprising a release mechanism operable to release a single container from a stack of containers stored in a first storage cassette removably mounted on the apparatus and to locate the single container at the first position.

22. Apparatus according to claim 21, in which the release mechanism comprises an escapement mechanism comprising a pair of escapement members arranged one on each side of the first position and pivotable movable about horizontal axes between one position in which the escapement members supports the stack of containers from beneath, a further position in which the escapement members grip the penultimate container in the stack and supports the lowest container in the stack from beneath, and a yet further position in which the escapement members grip the penultimate container while letting the lowest container fall into the first position.

23. Apparatus according to claim 21, in which the release mechanism comprises:
(a) a pair of grippers operable to support the stack of containers by gripping at least the lowest container in the stack from two opposite sides; and
(b) a vertically movable support device arranged below the stack of containers and which is movable between a retracted position located substantially at the same height as the first position,
(c) a support position in which the support device support the stack from below by contacting the lowest container supported by the pair of grippers, and
(d) an intermediate position separated from the support position by a distance corresponding to the thickness of a single container.

24. Apparatus according to claim 23, in which the intermediate position can be adjusted so that the release mechanism can release and locate containers of different thicknesses.

25. Apparatus according to claim 23, and further comprising a piston assembly operable to move the support device between the retracted position, the intermediate position and the support position, the piston assembly comprising a main piston operable to move the support device between the retracted position and the support position, and at least one subsidiary piston operable to locate the support device in the intermediate position.

26. Apparatus according to claim 25, and further comprising an adjustable abutment having portions of different thickness and operable to determine the movement of the subsidiary piston so as to alter the intermediate position in which the subsidiary piston locates the support device.

27. Apparatus according to claim 23, in which the grippers comprise a pair of opposed vertical plates operable to move towards and away from each other in a horizontal direction.

28. Apparatus according to claim 20, and further comprising a lifting device operable to transfer a container from the third position into a second storage cassette removably mounted on the apparatus.

29. Apparatus according to claim 20, in which the lid handling assembly is configured to handle for biological sample containers having the form of well plates.

30. Apparatus according to claim 20, and further comprising one or more additional conveyor assemblies and lid handling assemblies, and operable to convey, remove lids from, and replace lids onto a plurality of containers simultaneously.

31. An apparatus for working with biological material, comprising:
(a) a work surface;
(b) a first container handling apparatus, for handling biological sample containers containing biological material, comprising:
  (i) a storage assembly operable to store containers, deliver containers to a first pick-up position, and remove containers from the first pick-up position;
  (ii) a first conveyor assembly operable to convey containers between the first pick-up position and a first working position on the work surface; and
  (iii) a first lid-handling assembly operable to remove lids from containers as they are conveyed through the first lid handling assembly from the first pick-up position to a first arraying position and to replace the lids onto the containers as they are conveyed through the first lid handling assembly from the first arraying position to the first pick-up position, wherein lid removal and replacement is effected by mechanical interaction between the lids and the first lid handling assembly as the containers are conveyed through the first lid handling assembly;
(c) a second container handling apparatus, for handling well plates, comprising:
  (i) a well plate release mechanism operable to release well plates from a first storage cassette containing a stack of well plates and to deliver them to a second pick-up position;
  (ii) a second conveyor assembly operable to convey well plates from the second pick-up position to a second working position on the work surface and from the second working position to a return position;
  (iii) a second lid-handling assembly operable to remove lids from well-plates as they are conveyed through the second lid handling assembly from the second pick-up position to the second working position and to replace the lids onto the well-plates as they are conveyed through the second lid handling assembly from the second working position to the return position, wherein lid removal and replacement are effected by mechanical interaction between the lids and the second lid handling assembly as the containers are conveyed through the second lid handling assembly; and
  (iv) a well plate loading mechanism operable to transfer well plates from the return position into a second storage cassette; and
  (v) a head carrying a plurality of pins or pipettes operable to move over the work surface, pick up material from containers in the first working position and deposit the material in well plates in the second working position.

32. A method of handling biological sample containers each having a lid, the method comprising:
(a) conveying a container with a lid from a first position through a lid handling assembly;
(b) arranging a first mechanical interaction between the lid and the lid handling assembly as the container is conveyed through the lid handling assembly which removes the lid from the container;
(c) conveying the container without its lid to a second position;
(d) conveying the container without its lid from the second position through the lid handling assembly;
(e) arranging a second mechanical interaction between the lid and the lid handling assembly as the container is conveyed through the lid handling assembly which replaces the lid onto the container; and
(f) conveying the container with its lid back to the first position, wherein the first mechanical interaction is effected by conveying the container between at least one pair of rotatable rollers having parallel axes of rotation inclined with respect to a plane in which the containers are conveyed, each roller being biased towards the opposite roller, and arranged to grip the lid as the container is conveyed through the lid handling assembly and feed the lid in a forwardly and upwardly direction.

33. A method according to claim 32, in which the first mechanical interaction further is effected by conveying the container between a pair of ramps having lower ramp ends which face towards the first position and are arranged to pass under side walls of the lid of the container as the container is conveyed through the lid handling assembly, wherein at least one pair of rotatable rollers is located in front of lower ends of the pair of ramps, and arranged to engage the lid as the container is conveyed through the lid handling assembly and to direct the lid onto the ramps.

* * * * *